(12) United States Patent
Park et al.

(10) Patent No.: US 11,634,760 B2
(45) Date of Patent: Apr. 25, 2023

(54) METHOD FOR AMPLIFYING TARGET NUCLEIC ACID AND COMPOSITION FOR AMPLIFYING TARGET NUCLEIC ACID

(71) Applicant: PANAGENE INC., Daejeon (KR)

(72) Inventors: Jaejin Park, Seoul (KR); Minseo Kim, Gimhae-si (KR)

(73) Assignee: PANAGENE INC., Daejeon (KR)

( * ) Notice: Subject to any disclaimer, the term of this patent is extended or adjusted under 35 U.S.C. 154(b) by 117 days.

(21) Appl. No.: 16/768,356

(22) PCT Filed: Nov. 28, 2018

(86) PCT No.: PCT/KR2018/014776
§ 371 (c)(1),
(2) Date: May 29, 2020

(87) PCT Pub. No.: WO2019/107893
PCT Pub. Date: Jun. 6, 2019

(65) Prior Publication Data
US 2021/0002696 A1    Jan. 7, 2021

(30) Foreign Application Priority Data
Nov. 29, 2017  (KR) .......................... 10-2017-0161453

(51) Int. Cl.
*C12Q 1/686*  (2018.01)
*C12Q 1/6848*  (2018.01)

(52) U.S. Cl.
CPC ........... *C12Q 1/686* (2013.01); *C12Q 1/6848* (2013.01); *C12Q 2525/107* (2013.01);
(Continued)

(58) Field of Classification Search
CPC ................ C12Q 1/686; C12Q 1/6848; C12Q 2525/107; C12Q 2525/113;
(Continued)

(56) References Cited

U.S. PATENT DOCUMENTS 5,679,512 A   10/1997  Laney et al.
6,723,507 B1 *  4/2004  Lee ..................... C12Q 1/6851
                                                                435/6.15
(Continued)

FOREIGN PATENT DOCUMENTS

EP   1255865 B1   4/2007
EP   2414547 B1   3/2014
(Continued)

OTHER PUBLICATIONS

Nagai, "Genetic heterogeneity of the epidermal growth factor receptor in non-small cell lung cancer cell lines revealed by a rapid and sensitive detection system, the peptide nucleic acid-locked nucleic acid PCR clamp", Cancer Res Aug. 15, 2005 (65) (16) 7276-7282; DOI: 10.1158/0008-5472.CAN-05-0331.
(Continued)

*Primary Examiner* — Angela M. Bertagna
(74) *Attorney, Agent, or Firm* — Optima Law Group, APC; Thomas E. Jurgensen

(57) ABSTRACT

The present invention relates to a method for detecting a target nucleic acid, which induces any surrogate target to be amplified in the presence of the target nucleic acid and is useful for molecular diagnosis, prenatal diagnosis, early diagnosis, cancer diagnosis, genetic related diagnosis, genetic trait diagnosis, diagnosis of infectious bacteria, identification of drug-resistant bacteria, forensic medicine, species identification of organisms, and the like.

21 Claims, 45 Drawing Sheets
Specification includes a Sequence Listing.

(52) U.S. Cl.
CPC .. *C12Q 2525/113* (2013.01); *C12Q 2525/179* (2013.01); *C12Q 2525/186* (2013.01); *C12Q 2525/197* (2013.01); *C12Q 2525/204* (2013.01); *C12Q 2563/107* (2013.01); *C12Q 2563/173* (2013.01); *C12Q 2565/101* (2013.01); *C12Q 2565/1015* (2013.01)

(58) Field of Classification Search
CPC ........ C12Q 2525/179; C12Q 2525/186; C12Q 2525/197; C12Q 2525/204; C12Q 2563/107; C12Q 2563/173; C12Q 2565/101; C12Q 2565/1015; C12Q 2531/113
See application file for complete search history.

(56) References Cited

U.S. PATENT DOCUMENTS

| | | | |
|---|---|---|---|
| 2002/0182598 A1* | 12/2002 | Zhang | C12Q 1/6834 435/6.1 |
| 2007/0059700 A1 | 3/2007 | Tao et al. | |
| 2014/0329245 A1 | 11/2014 | Spier et al. | |

FOREIGN PATENT DOCUMENTS

| | | |
|---|---|---|
| JP | 2010-514420 A | 5/2010 |
| KR | 10-2014-0094113 A | 7/2014 |
| KR | 10-1770363 B1 | 8/2017 |
| WO | 2008080029 A2 | 7/2008 |
| WO | 2015068957 A1 | 5/2015 |

OTHER PUBLICATIONS

English Translation of Patent Publication No. JP 2010-514420 A.
Higuchi, R., et al., "Simultaneous Amplification and Detection of Specific DNA Sequences", Nature, Apr. 1992, pp. 413-417, vol. 10, Nature Publishing Group.
Higuchi, R., et al., "Kinetic PCR Analysis: Real-time Monitoring of DNA Amplification Reactions", Nature, Sep. 1993, pp. 1026-1030, vol. 11, Nature Publishing Group.
Mcdowell, D. G., et al., "Localised sequence regions possessing high melting temperatures prevent the amplification of a DNA mimic in competitive PCR", Nucleic Acids Research, 1998, pp. 3340-3347, vol. 26, No. 14, Oxford University Press.
Rajasekharan, S. K., et al., "Ras and Ras mutations in cancer", Central European Journal of Biology, 1993, pp. 609-624, *Versita* Sp. z o.o. DOI: 10.2478/s11535-013-0158-5.
Zhang, H., et al., "ErbB receptors: from oncogenes to targeted cancer therapies", The Journal of Clinical Investigation, Aug. 2007, pp. 2051-2058, vol. 117, No. 8, The American Society for Clinical Investigation.2058. https://doi.org/10.1172/JCI32278.
English Translation of Patent Application No. KR 10-2014-0094113 A.
Spencer, S., Tamminen, M., Preheim, S. et al. Massively parallel sequencing of single cells by epicPCR links functional genes with phylogenetic markers. ISME J 10, 427-436 (2016). https://doi.org/10.1038/ismej.2015.124.

* cited by examiner (a) Fusion amplicon according to the present invention (b) Conventional polymerase chain reaction product (a)

(b)

(c)

(d)

(e)

Amount of target nucleic acid $10^4$ copies/reaction

Amplification curve

Melting curve

Amount of target nucleic acid 0 copies/reaction

Amplification curve

Melting curve

Amount of target nucleic acid $10^4$ copies/reaction

Amplification curve

Melting curve

Amount of target nucleic acid $10^3$ copies/reaction

Amplification curve

Melting curve

Amount of target nucleic acid $10^2$ copies/reaction

Amplification curve

Melting curve

Amount of target nucleic acid $10^1$ copies/reaction

Amplification curve

Melting curve

Amount of target nucleic acid

0 copies/reaction

Amplification curve

Melting curve

Amount of target nucleic acid - $10^2$ copies/reaction
Type of surrogate target - Surrogate target 1

Amplification curve

Melting curve

Amount of target nucleic acid - 0 copies/reaction
Type of surrogate target - Surrogate target 1

Amplification curve

Melting curve

Amount of target nucleic acid - $10^2$ copies/reaction
Type of surrogate target - Surrogate target 2

Amplification curve

Melting curve

**Amount of target nucleic acid - 0 copies/reaction
Type of surrogate target - Surrogate target 2**

Amplification curve

Melting curve

Amount of target nucleic acid - $10^2$ copies/reaction
Type of surrogate target - Surrogate target 3

Amplification curve

Melting curve

Amount of target nucleic acid - 0 copies/reaction
Type of surrogate target - Surrogate target 3

Amplification curve

Melting curve

Amount of target nucleic acid - $10^2$ copies/reaction
Type of surrogate target - Surrogate target 2+3

Amplification curve

Melting curve

**Amount of target nucleic acid - 0 copies/reaction
Type of surrogate target - Surrogate target 2+3**

Amplification curve

Melting curve

Detection of target nucleic acid through fusion amplicon 1

Detection of target nucleic acid through fusion amplicon 2

― HRAS target nucleic acid was added
⋯ NTC (target nucleic acid was not added)

Target nucleic acid amplification method of the present invention (adjustment of sensitivity by adjustment of amount of surrogate target)

Conventional target nucleic acid amplification method (adjustment of sensitivity by adjustment of amount of primers)

Target nucleic acid amplification method of the present invention

Amount of EGFR target $10^6$ copies

Amount of HRAS target $10^5$ copies

Amount of EGFR target $10^6$ copies

Amount of HRAS target $10^4$ copies

Target nucleic acid amplification method of the present invention
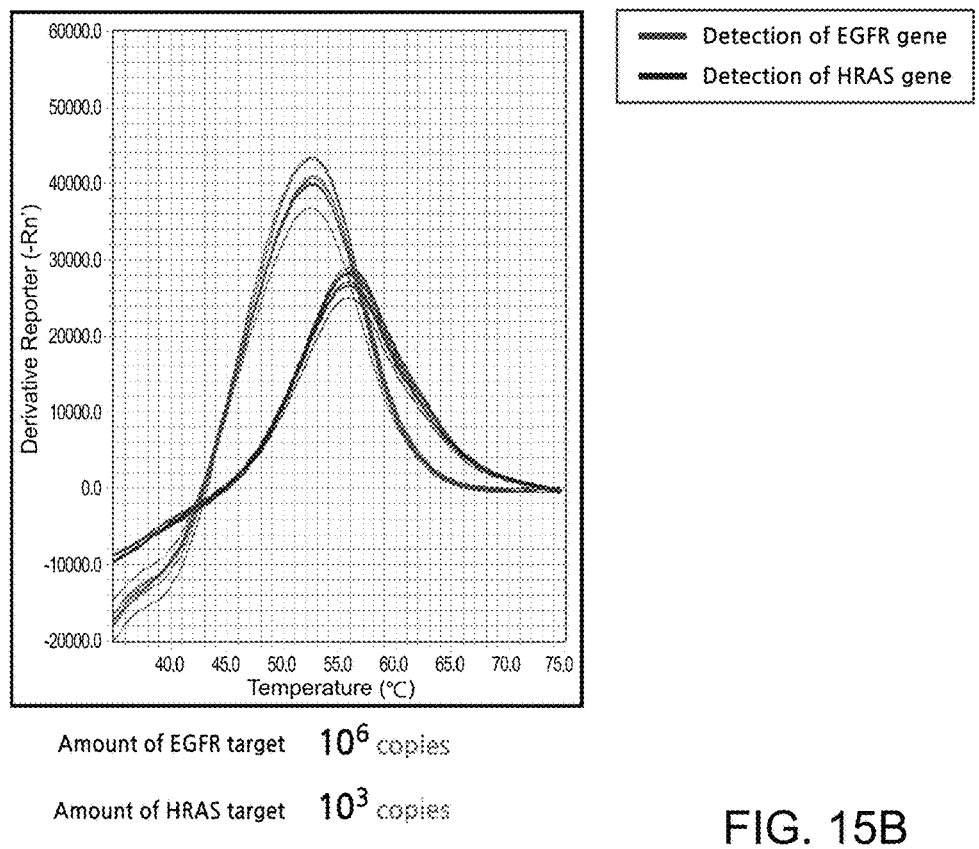
Amount of EGFR target　　$10^6$ copies
Amount of HRAS target　　$10^3$ copies
FIG. 15B
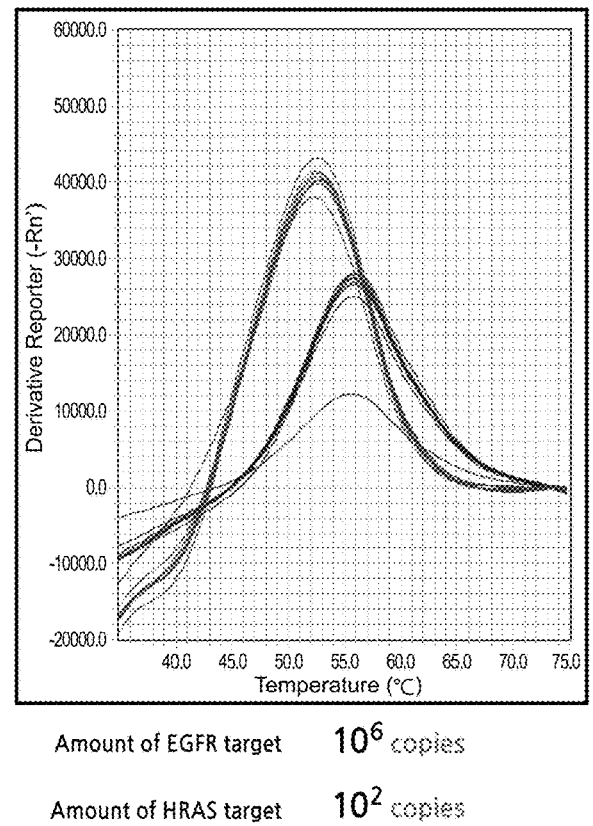
Amount of EGFR target　　$10^6$ copies
Amount of HRAS target　　$10^2$ copies Target nucleic acid amplification method of the present invention
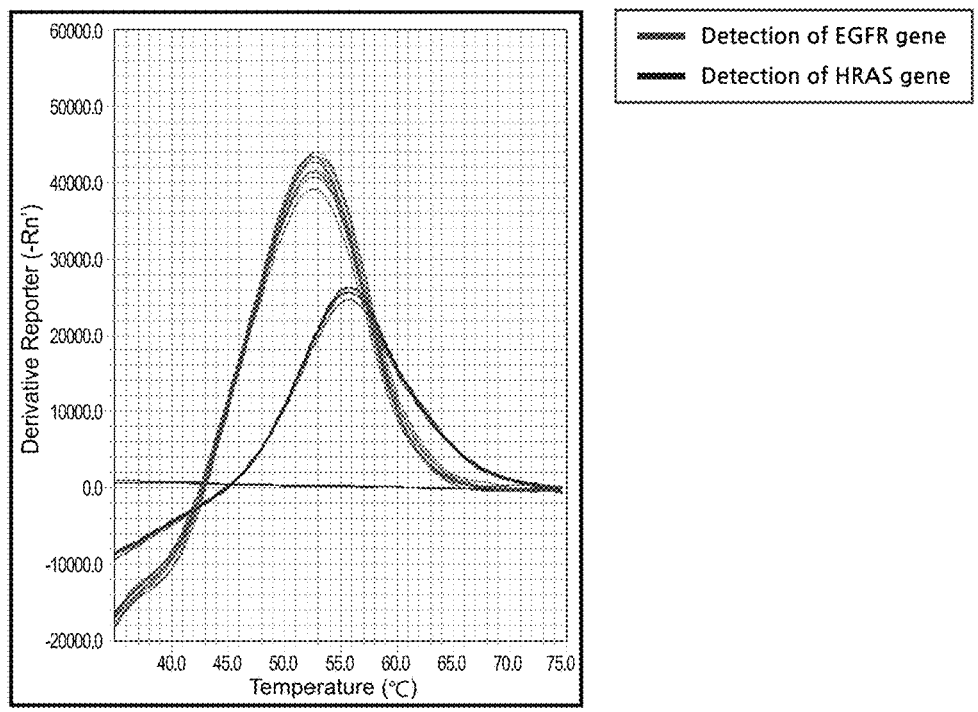
Amount of EGFR target     $10^6$ copies
Amount of HRAS target     $10^1$ copies
FIG. 15C
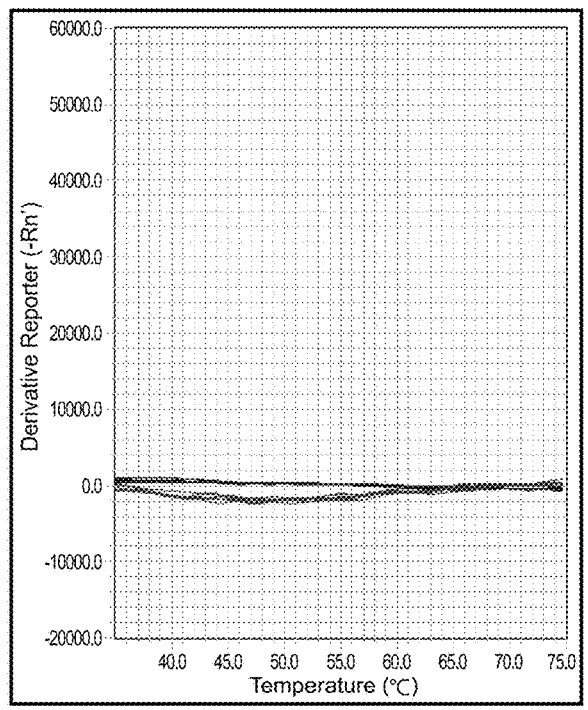
Amount of EGFR target     NTC
Amount of HRAS target     NTC

Conventional target nucleic acid amplification method
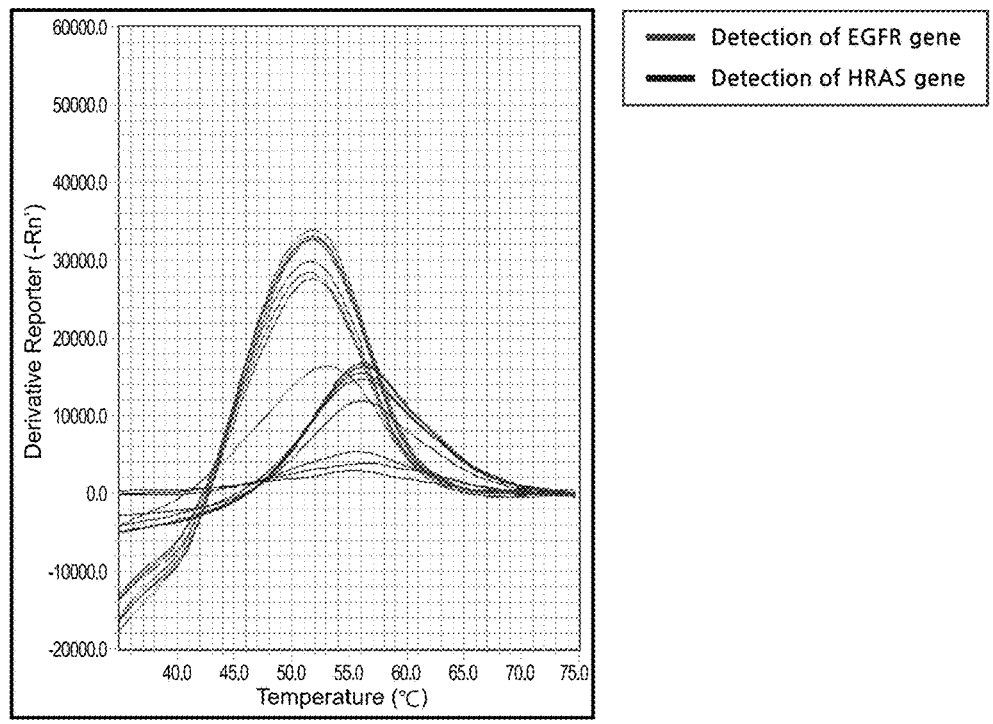
Amount of EGFR target $10^6$ copies
Amount of HRAS target $10^5$ copies
FIG. 15D
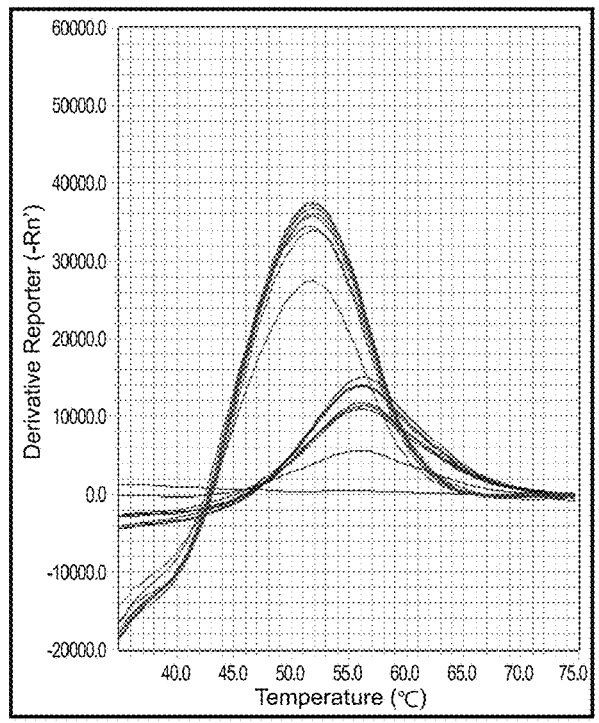
Amount of EGFR target $10^6$ copies
Amount of HRAS target $10^4$ copies

Conventional target nucleic acid amplification method
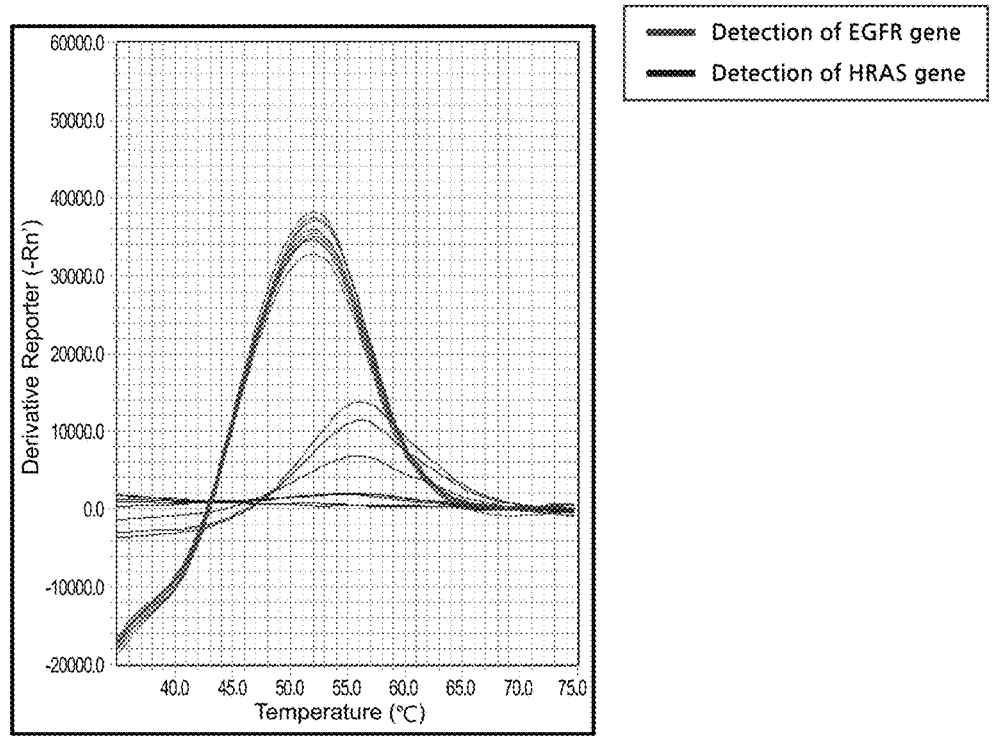
Amount of EGFR target    $10^6$ copies
Amount of HRAS target    $10^3$ copies
FIG. 15E
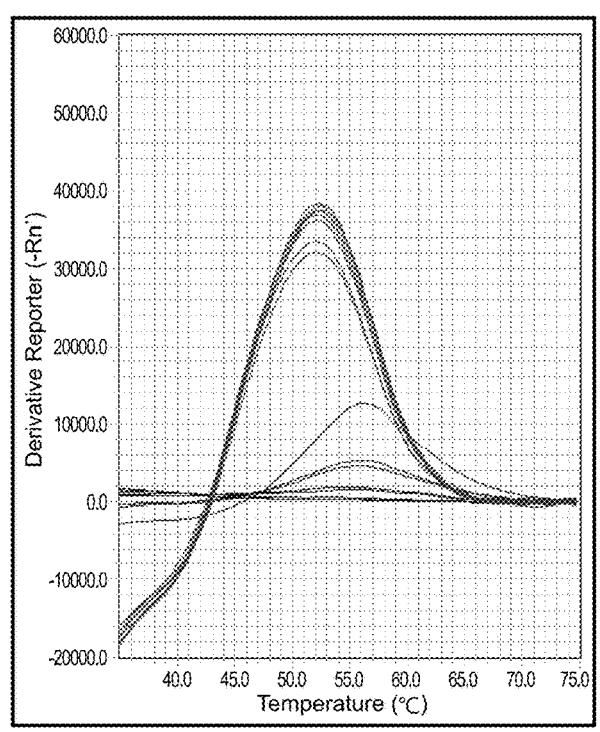
Amount of EGFR target    $10^6$ copies
Amount of HRAS target    $10^2$ copies

Conventional target nucleic acid amplification method
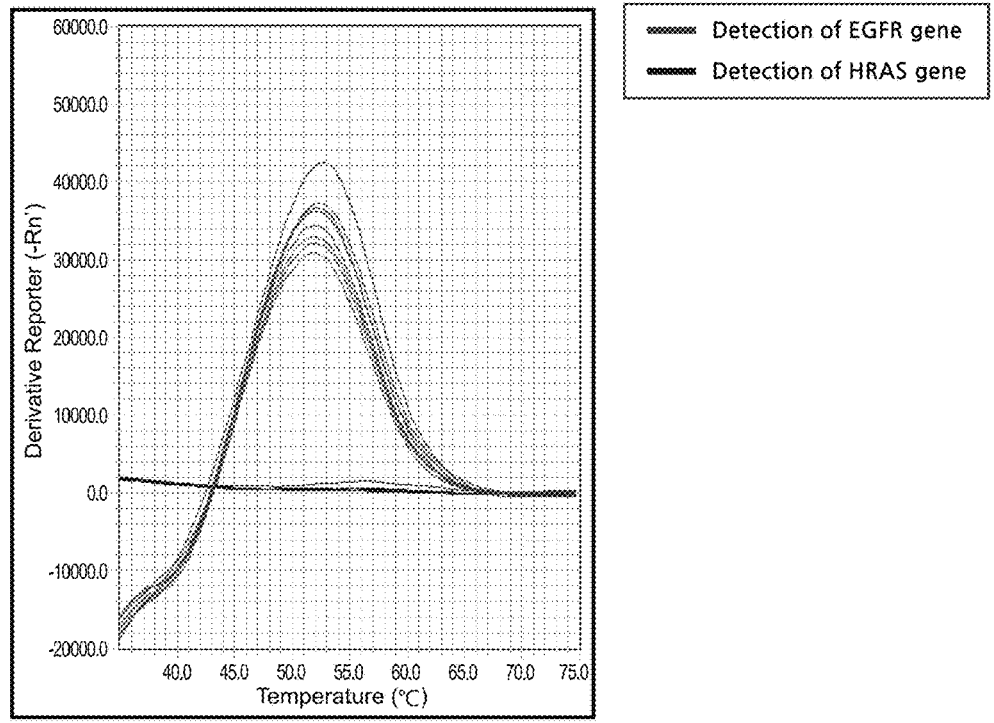
Amount of EGFR target     $10^6$ copies
Amount of HRAS target     $10^1$ copies
FIG. 15F
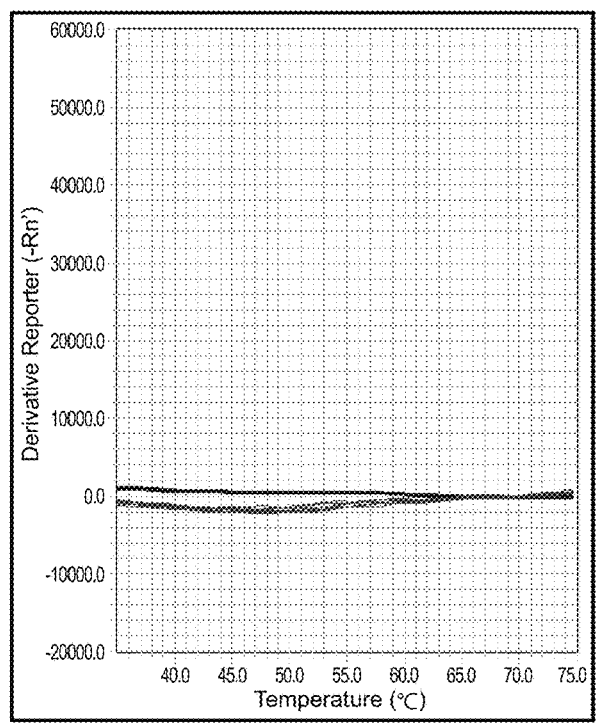
Amount of EGFR target     NTC
Amount of HRAS target     NTC

Target nucleic acid amplification method of the present invention
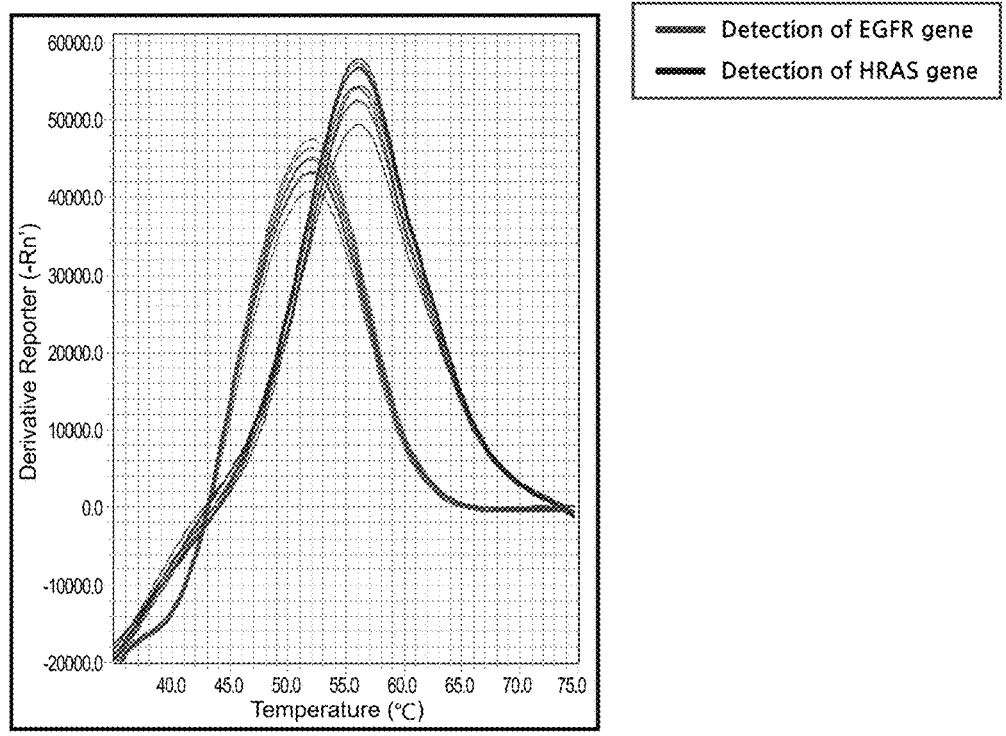
Amount of EGFR target $10^5$ copies
Amount of HRAS target $10^6$ copies
FIG. 15G
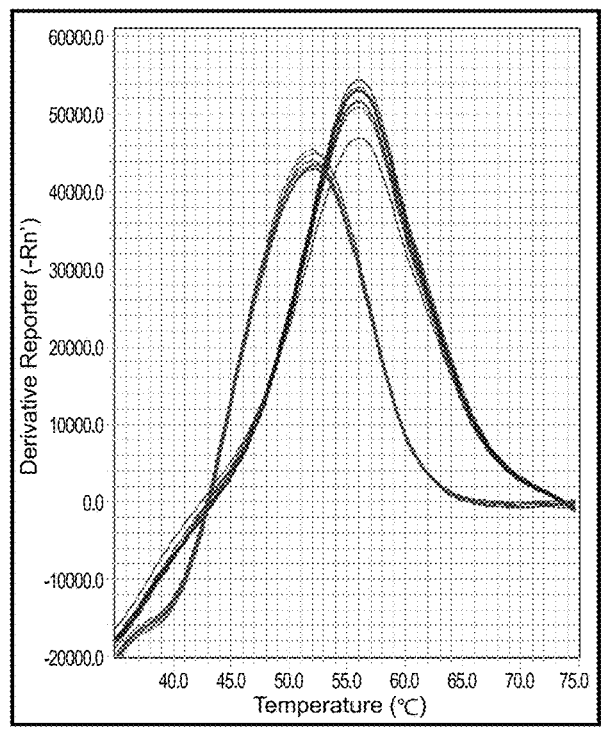
Amount of EGFR target $10^4$ copies
Amount of HRAS target $10^6$ copies

Target nucleic acid amplification method of the present invention
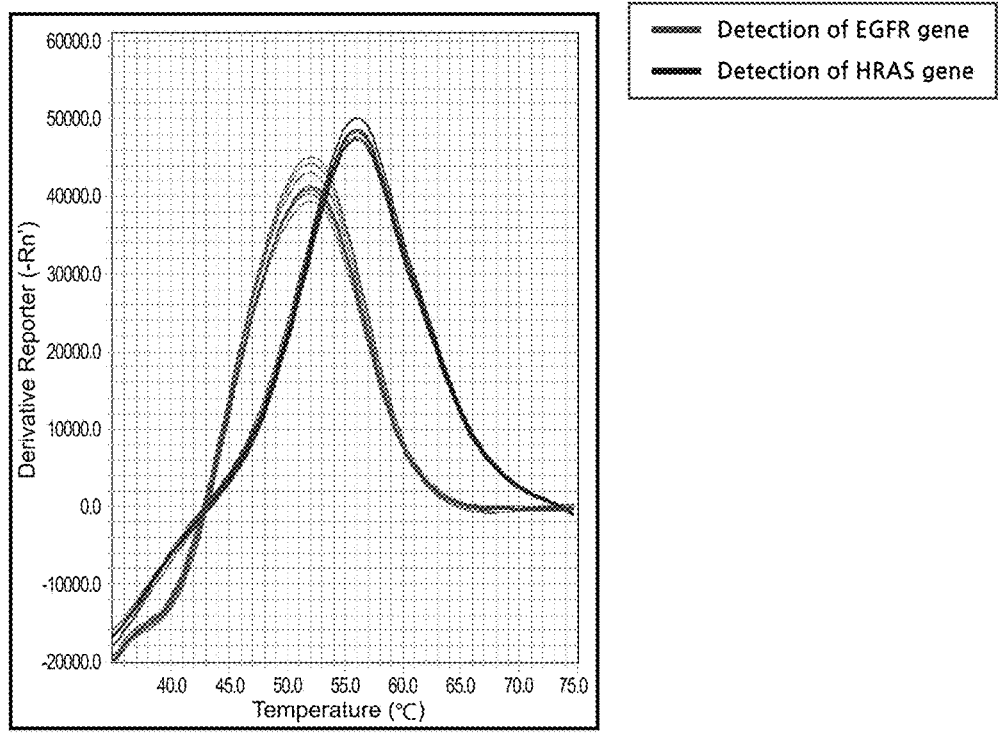
Amount of EGFR target  $10^3$ copies
Amount of HRAS target  $10^6$ copies
FIG. 15H
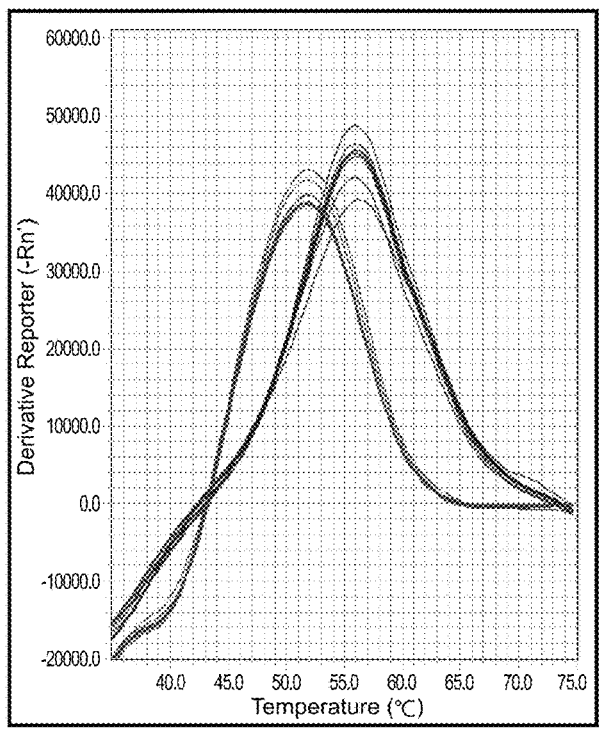
Amount of EGFR target  $10^2$ copies
Amount of HRAS target  $10^6$ copies

Target nucleic acid amplification method of the present invention
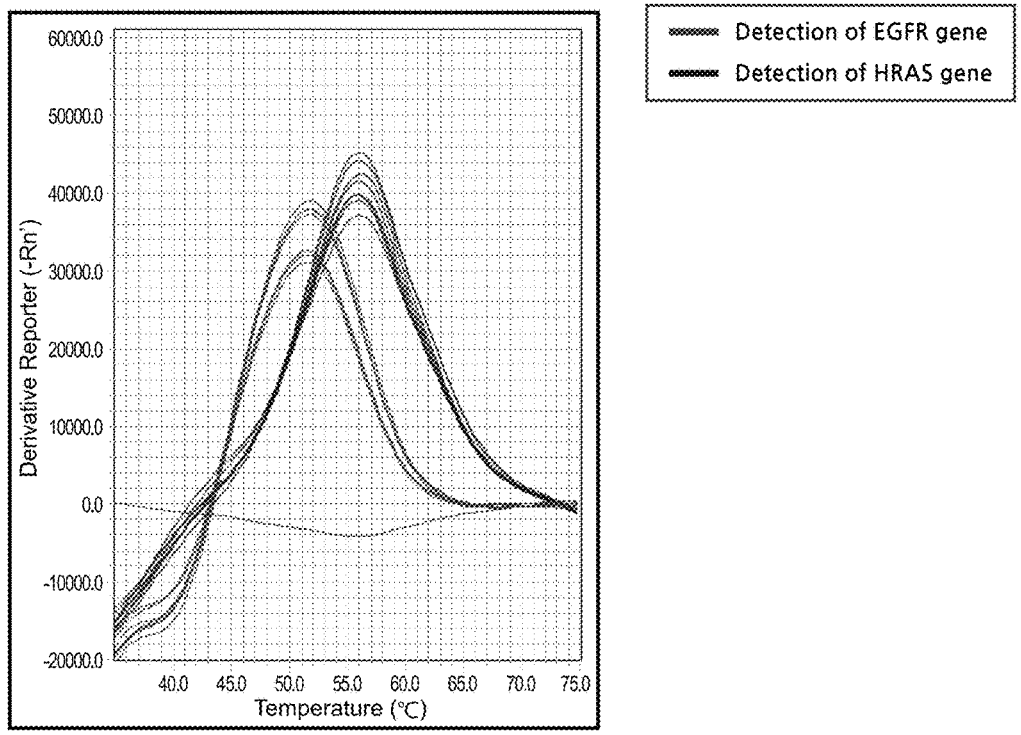
Amount of EGFR target $10^1$ copies
Amount of HRAS target $10^6$ copies
FIG. 15I
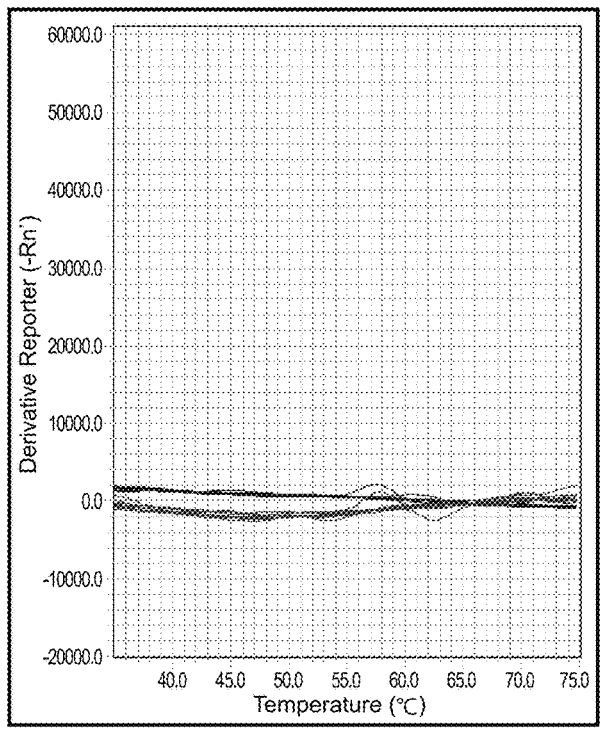
Amount of EGFR target NTC
Amount of HRAS target NTC

Conventional target nucleic acid amplification method
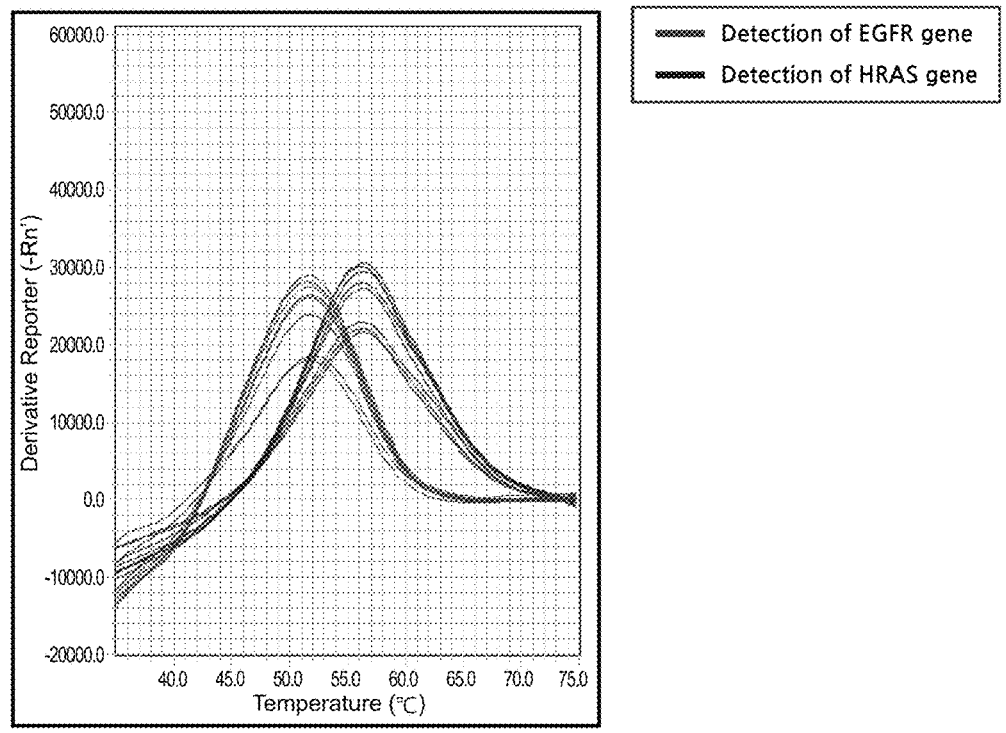
Amount of EGFR target $10^5$ copies
Amount of HRAS target $10^6$ copies
FIG. 15J
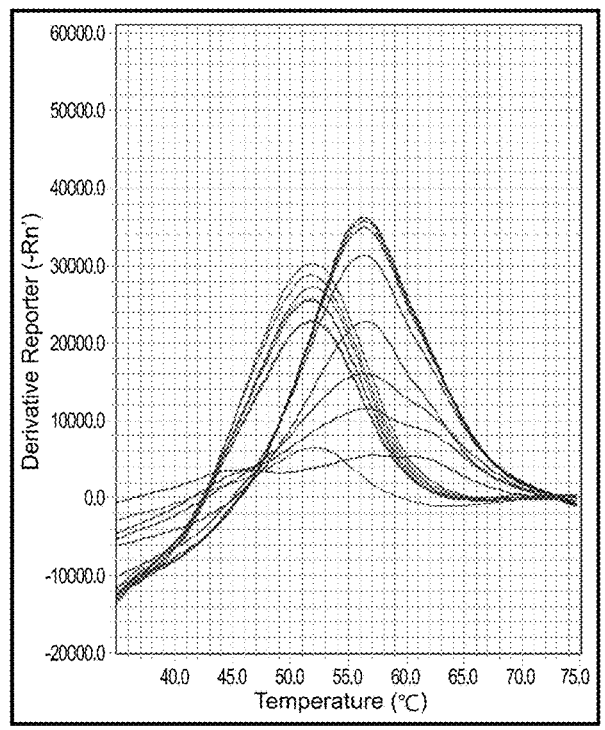
Amount of EGFR target $10^4$ copies
Amount of HRAS target $10^6$ copies

Conventional target nucleic acid amplification method
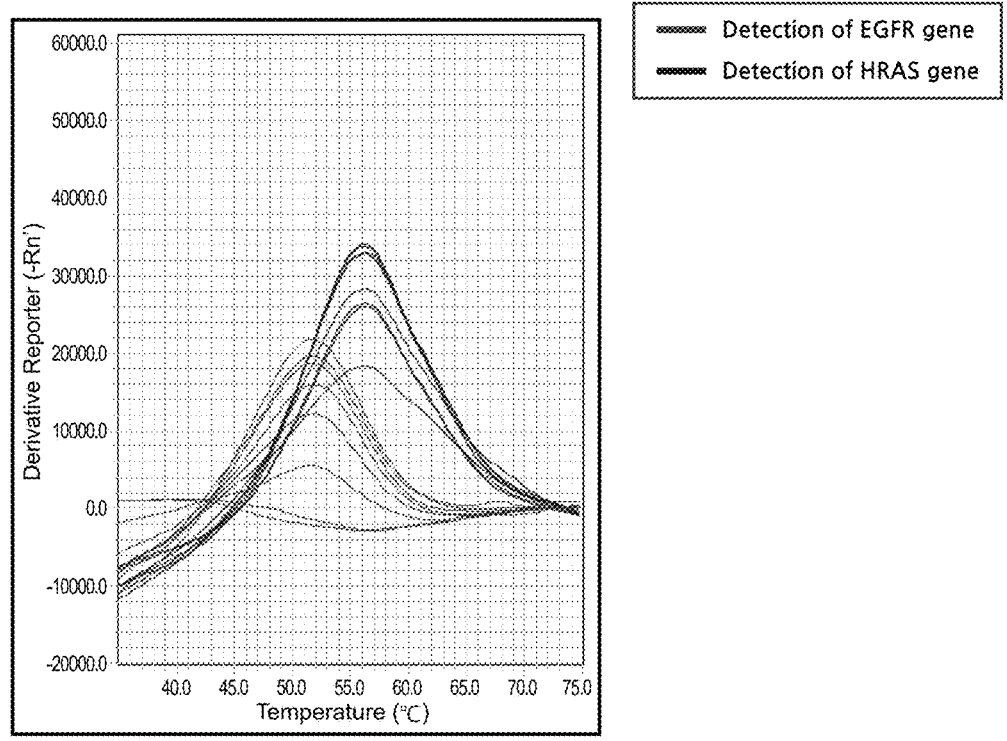
Amount of EGFR target  $10^3$ copies
Amount of HRAS target  $10^6$ copies
FIG. 15K
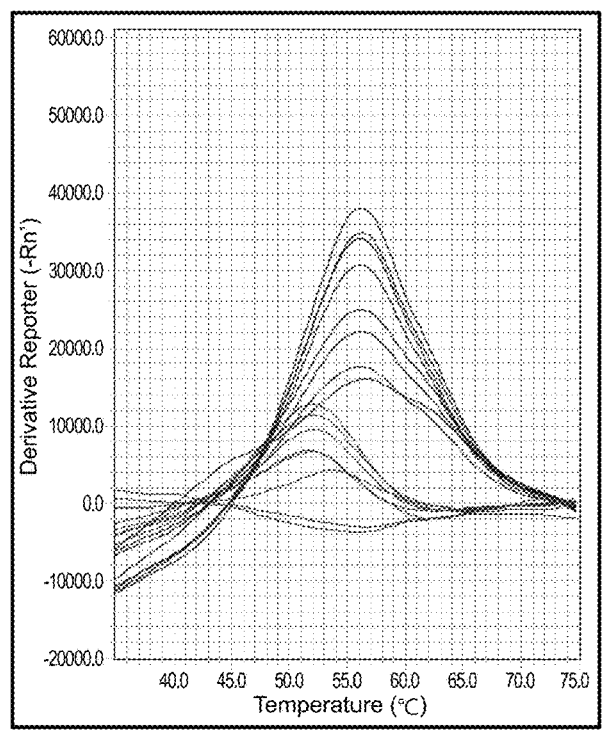
Amount of EGFR target  $10^2$ copies
Amount of HRAS target  $10^6$ copies

Conventional target nucleic acid amplification method
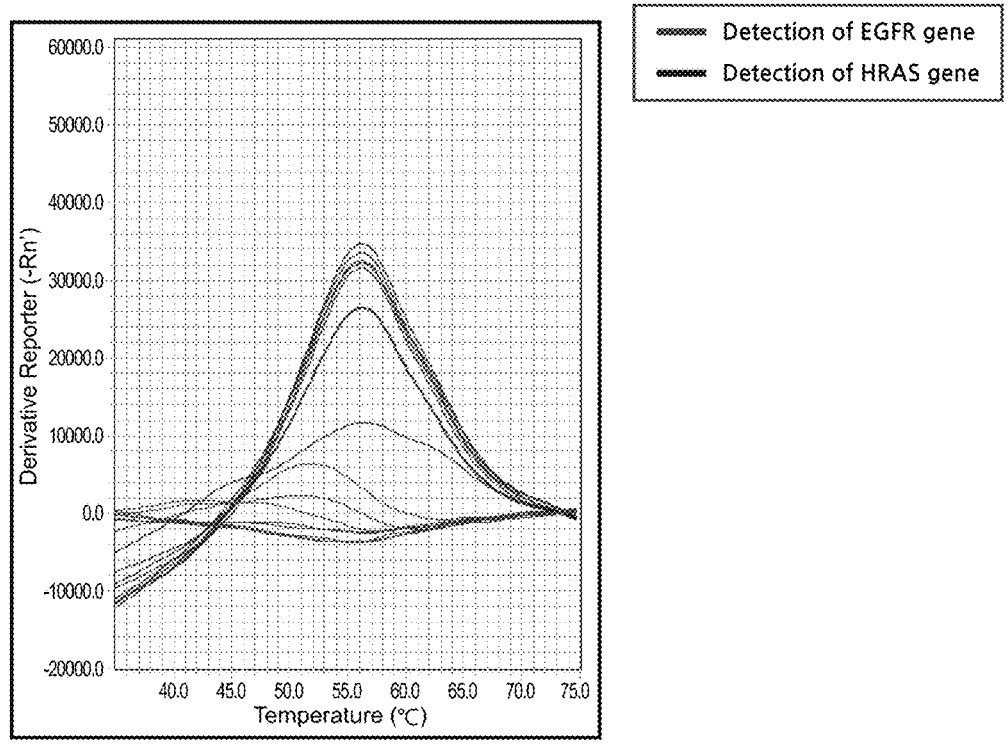
Amount of EGFR target    $10^1$ copies
Amount of HRAS target    $10^6$ copies
FIG. 15L
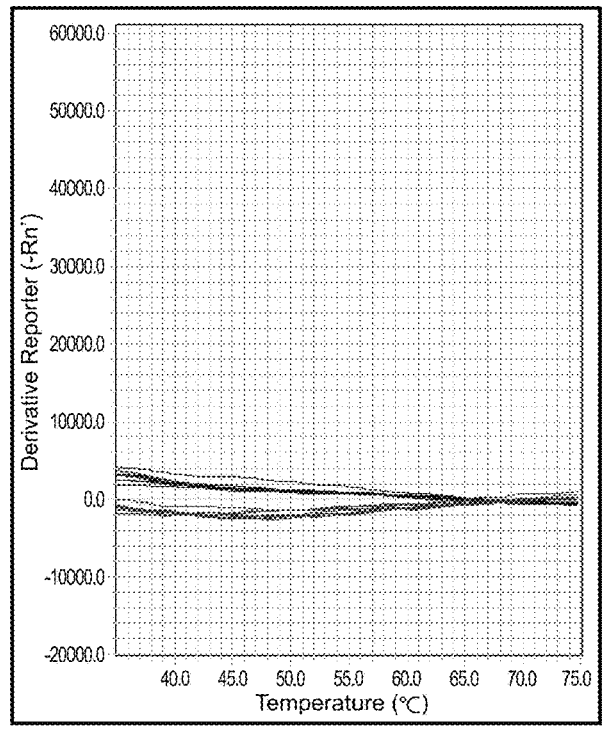
Amount of EGFR target    NTC
Amount of HRAS target    NTC

SEQUENCE LISTING

```
<160> NUMBER OF SEQ ID NOS: 23

<210> SEQ ID NO 1
<211> LENGTH: 17
<212> TYPE: DNA
<213> ORGANISM: Artificial Sequence
<220> FEATURE:
<223> OTHER INFORMATION: Target Specific Primer 1

<400> SEQUENCE: 1
gccgcctgct gggcatc                                                    17

<210> SEQ ID NO 2
<211> LENGTH: 19
<212> TYPE: DNA
<213> ORGANISM: Artificial Sequence
<220> FEATURE:
<223> OTHER INFORMATION: Target Specific Primer 2

<400> SEQUENCE: 2
acctccaccg tgcagctca                                                  19

<210> SEQ ID NO 3
<211> LENGTH: 17
<212> TYPE: DNA
<213> ORGANISM: Artificial Sequence
<220> FEATURE:
<223> OTHER INFORMATION: Target specific Primer 3
```

<400> SEQUENCE: 3
agcgcactct tgcccac                                                17

<210> SEQ ID NO 4
<211> LENGTH: 17
<212> TYPE: DNA
<213> ORGANISM: Artificial Sequence
<220> FEATURE:
<223> OTHER INFORMATION: Target specific primer 4

<400> SEQUENCE: 4
gccgcctgct gggcatc                                                17

<210> SEQ ID NO 5
<211> LENGTH: 18
<212> TYPE: DNA
<213> ORGANISM: Artificial Sequence
<220> FEATURE:
<223> OTHER INFORMATION: Target Specific Primer 5

<400> SEQUENCE: 5
ggtcagcgca ctcttgcc                                               18

<210> SEQ ID NO 6
<211> LENGTH: 20
<212> TYPE: DNA
<213> ORGANISM: Artificial Sequence
<220> FEATURE:
<223> OTHER INFORMATION: Amplification Primer 1

<400> SEQUENCE: 6
catcaggagc agttacgaag                                             20

<210> SEQ ID NO 7
<211> LENGTH: 19
<212> TYPE: DNA
<213> ORGANISM: Artificial Sequence
<220> FEATURE:
<223> OTHER INFORMATION: Amplification Primer 2

<400> SEQUENCE: 7
aaccttagca cgaatagcg                                              19

<210> SEQ ID NO 8
<211> LENGTH: 19
<212> TYPE: DNA
<213> ORGANISM: Artificial Sequence
<220> FEATURE:
<223> OTHER INFORMATION: Amplification Primer 3

<400> SEQUENCE: 8
gctgttgctt ccgctattc                                              19

<210> SEQ ID NO 9
<211> LENGTH: 56
<212> TYPE: DNA
<213> ORGANISM: Artificial Sequence
<220> FEATURE:
<223> OTHER INFORMATION: Surrogate target 1

<400> SEQUENCE: 9 tttttctgg actatgtccg ggaacacagg cttcgtaact gctcctgatg aaaaaa      56

<210> SEQ ID NO 10
<211> LENGTH: 50

-continued

```
<212> TYPE: DNA
<213> ORGANISM: Artificial Sequence
<220> FEATURE:
<223> OTHER INFORMATION: Surrogate target 2

<400> SEQUENCE: 10
ctggactatg tccgggaaca caggcttcgt aactgctcct gatgaaaaaa            50

<210> SEQ ID NO 11
<211> LENGTH: 44
<212> TYPE: DNA
<213> ORGANISM: Artificial Sequence
<220> FEATURE:
<223> OTHER INFORMATION: Surrogate target 3

<400> SEQUENCE: 11
catcaggagc agttacgaag cctgtgttcc cggacatagt ccag                  44

<210> SEQ ID NO 12
<211> LENGTH: 56
<212> TYPE: DNA
<213> ORGANISM: Artificial Sequence
<220> FEATURE:
<223> OTHER INFORMATION: Surrogate target 4

<400> SEQUENCE: 12 tttttatat tccgtcatcg ctcctcagga ccgctattcg tgctaaggtt aaaaaa      56

<210> SEQ ID NO 13
<211> LENGTH: 50
<212> TYPE: DNA
<213> ORGANISM: Artificial Sequence
<220> FEATURE:
<223> OTHER INFORMATION: Surrogate target 5

<400> SEQUENCE: 13
catcaggagc agttacgaag aataatgatg tgaggagcga tgacggaata            50

<210> SEQ ID NO 14
<211> LENGTH: 60
<212> TYPE: DNA
<213> ORGANISM: Artificial Sequence
<220> FEATURE:
<223> OTHER INFORMATION: Surrogate target 6

<400> SEQUENCE: 14
catcaggagc agttacgaag aataatgatg aataatgatg tgaggagcga tgacggaata  60

<210> SEQ ID NO 15
<211> LENGTH: 52
<212> TYPE: DNA
<213> ORGANISM: Artificial Sequence
<220> FEATURE:
<223> OTHER INFORMATION: Surrogate target 7

<400> SEQUENCE: 15 tttttcagc tcatgcccctt cggctaggaa tagcggaagc aacagcaaaa aa         52

<210> SEQ ID NO 16
<211> LENGTH: 48
<212> TYPE: DNA
<213> ORGANISM: Artificial Sequence
<220> FEATURE:
<223> OTHER INFORMATION: Surrogate target 8

<400> SEQUENCE: 16
```

```
atattccgtc atcgctcctc ggcttcgtaa ctgctcctga tgaaaaaa                    48

<210> SEQ ID NO 17
<211> LENGTH: 42
<212> TYPE: DNA
<213> ORGANISM: Artificial Sequence
<220> FEATURE:
<223> OTHER INFORMATION: Surrogate target 9

<400> SEQUENCE: 17
catcaggagc agttacgaag ccgaggagcg atgacggaat at                          42

<210> SEQ ID NO 18
<211> LENGTH: 21
<212> TYPE: DNA
<213> ORGANISM: Artificial Sequence
<220> FEATURE:
<223> OTHER INFORMATION: Assistant primer 1

<400> SEQUENCE: 18
gctatcccag gagcgcagac c                                                 21

<210> SEQ ID NO 19
<211> LENGTH: 22
<212> TYPE: DNA
<213> ORGANISM: Artificial Sequence
<220> FEATURE:
<223> OTHER INFORMATION: Assistant primer 2

<400> SEQUENCE: 19
tgtgggtttg cccttcagat gg                                                22

<210> SEQ ID NO 20
<211> LENGTH: 10
<212> TYPE: DNA
<213> ORGANISM: Artificial Sequence
<220> FEATURE:
<223> OTHER INFORMATION: Probe 1

<400> SEQUENCE: 20
cacaggcttc                                                              10

<210> SEQ ID NO 21
<211> LENGTH: 12
<212> TYPE: DNA
<213> ORGANISM: Artificial Sequence
<220> FEATURE:
<223> OTHER INFORMATION: Probe 2

<400> SEQUENCE: 21
ctcatcatgc ag                                                           12

<210> SEQ ID NO 22
<211> LENGTH: 20
<212> TYPE: DNA
<213> ORGANISM: Artificial Sequence
<220> FEATURE:
<223> OTHER INFORMATION: Control Primer 2

<400> SEQUENCE: 22
tgaggagcga tgacggaata                                                   20

<210> SEQ ID NO 23
<211> LENGTH: 18
<212> TYPE: DNA
<213> ORGANISM: Artificial Sequence
```

```
<220> FEATURE:
<223> OTHER INFORMATION: Control Primer 3

<400> SEQUENCE: 23
cctgtaggag gaccccgg                                                    18
```

METHOD FOR AMPLIFYING TARGET NUCLEIC ACID AND COMPOSITION FOR AMPLIFYING TARGET NUCLEIC ACID

CROSS-REFERENCE TO RELATED APPLICATIONS

This is a U.S. national application filed under 35 U.S.C. 371 which is based on international application no. PCT/KR2018/014776 filed Nov. 28, 2018, which claims priority to KR application no. 10-2017-0161453 filed Nov. 29, 2017 and are incorporated herein by reference.

SEQUENCE LISTING

The instant application contains a Sequence Listing which was originally submitted electronically on May 29, 2020, and a subsequent Corrected Sequence Listing submitted on Jul. 1, 2020. Both of these Sequence Listings were deficient due to errors, accordingly, a Corrected Sequence Listing to overcome certain deficiencies in ASCII format and submitted electronically on Aug. 19, 2020 is hereby incorporated by reference in its entirety. Said Corrected ASCII copy, created Aug. 11, 2020, is named 1471-2001US-ST25-3 and is 4,693 bytes in size.

TECHNICAL FIELD

The present invention relates to a method for amplifying a target nucleic acid, which can minimize dependency on the nucleotide sequence of the target nucleic acid, and a method for amplifying a target nucleic acid, which can minimize changes in the amplification efficiency of the target nucleic acid in a process of increasing the detection sensitivity of the target nucleic acid. More specifically, the present invention relates to a method of implementing target nucleic acid amplification with high efficiency and sensitivity by inducing the production of a fusion amplicon between the target nucleic acid and any surrogate target when the target nucleic acid is present, and amplifying the fusion amplicon, a method of effectively adjusting the detection sensitivity of a target nucleic acid by controlling only the addition amount of the surrogate target in a process of producing the fusion amplicon between the target nucleic acid and any surrogate target, and a polymerase chain reaction (PCR) composition for implementing the methods.

BACKGROUND ART

Genetic information possessed by all living organisms on earth is the source of the characteristics of each individual, and is recorded in the sequence in which adenine (A), guanine (G), cytosine (C), thymine (T) and uracil (U) bases are arranged in nucleic acid (DNA or RNA). Thus, determining or identifying the sequence of these bases (nucleotide sequence) can be a process for identifying the characteristics of living organisms and understanding underlying metabolic mechanisms.

In recent years, molecular diagnostics have been widely used to determine the presence or characteristics of a living organism through a method of detecting or identifying a specific nucleotide sequence in the living organism. Typical examples of medically useful molecular diagnostics include detecting gene mutations related to human cancer or detecting pathogens that cause infectious diseases that can occur in humans, and other tests that detect harmful microorganisms in food are also part of molecular diagnostics.

Many of molecular diagnostic techniques for specifically identifying specific nucleotide sequences are performed using a polymerase chain reaction (PCR) with DNA polymerase. The polymerase chain reaction is performed using a composition comprising a pair of primers capable of specifically hybridizing with a target nucleic acid containing a specific nucleotide sequence region, and a thermostable DNA polymerase capable of developing the polymerase chain reaction using the target nucleic acid as a template and the primers as starting points, and a thermal cycler capable of applying a predetermined temperature to the composition in a stepwise and repeated manner. In addition, molecular diagnostics using the polymerase chain reaction use a nucleic acid-binding dye or a probe to detect a specific nucleotide sequence in a large amount of formed (amplified) target nucleic acid in real time, which is called real-time PCR (Higuchi, R. et al., Biotechnology 1992. 10:413-417, Higuchi, R. et al., Biotechnology 1993. 11:1026-1030).

Most of the molecular diagnostic methods so far have used a method of directly amplifying a target nucleic acid while identifying the presence or characteristics of the target nucleic acid through the polymerase chain reaction. One or more pairs of primers are used to amplify the target nucleic acid, and since the primers have to be complementary to the target nucleic acid, there are not many opportunities to arbitrarily adjust the nucleotide sequence. For this reason, the nucleotide sequence characteristics of the target nucleic acid directly affect the performance of molecular diagnostics. If the target nucleic acid has a high guanine (G)/cytosine (C) content, secondary structure formation and an excessively high melting temperature appear, which greatly reduce the amplification efficiency during the polymerase chain reaction. This has been pointed out as a major obstacle to the development of diagnostic products (McDowell, D. G. et al., Nucleic Acids Res. 1998. 26:3340-3347).

In addition, many molecular diagnostic methods to date have used probes capable of generating fluorescent signals while identifying the presence or characteristics of the target nucleic acid through real-time polymerase chain reaction. The probe also needs to have a nucleotide sequence complementary to the target nucleic acid, similar to the primer that amplifies the target nucleic acid, and for this reason, when the target nucleic acid is changed, the probe must also be changed, which is inefficient. If a polymerase chain reaction product is detected using a nucleic acid-binding dye rather than a target-specific probe, it is not necessary to change the nucleic acid-binding dye depending on the change of the target nucleic acid, but the nucleic acid-binding dye cannot distinguish the nucleotide sequence of the target nucleic acid, and hence there is a problem in that a limitation exists in target-specific detection.

In addition, the amplification efficiency of the target nucleic acid can be evaluated by the slope of the amplification curve obtained in the real-time polymerase chain reaction, and the detection sensitivity for the target nucleic acid can be expressed as a cycle threshold (Ct) value calculated from the amplification curve. However, in most molecular diagnostic methods to date, it is mainly necessary to adjust the nucleotide sequence or addition amount of the primer while optimizing the amplification efficiency or detection sensitivity of the target nucleic acid, and thus it is difficult to independently adjust the amplification efficiency and detection sensitivity. Thus, these diagnostic methods have a disadvantage in that it takes a lot of time and cost to optimize the amplification efficiency and detection sensitivity. That is, when the nucleotide sequence or addition amount of the primer changes, the amplification efficiency and the detection sensitivity also change, and for this reason, it is difficult to control the amplification efficiency in the process of increasing the detection sensitivity, and thus much trial and error is required.

Accordingly, the present inventors have made extensive efforts to develop a method of amplifying a target nucleic acid without being limited by the characteristics of the target nucleic acid, and a method of effectively increasing the sensitivity of target nucleic acid amplification while minimizing effects on the amplification efficiency of the nucleic acid. As a result, the present inventors have found that, when PCR is performed by a method of producing a fusion amplicon using a target-specific primer that hybridizes with the target nucleic acid, a surrogate target comprising a sequence that binds to the target nucleic acid and an arbitrary sequence, and an amplification primer capable of amplifying the surrogate target, dependence on the target nucleic acid can be minimized, and the target nucleic acid can also be amplified with high sensitivity and high efficiency, and when the amount of the surrogate target is adjusted, only the sensitivity of target nucleic acid amplification can be independently easily adjusted, thereby completing the present invention.

The above information disclosed in this Background section is only for enhancement of understanding of the background of the present invention. Therefore, it may not contain information that forms the conventional art that is already known in the art to which the present invention pertains.

SUMMARY OF THE INVENTION

It is an object of the present invention to provide a method for amplifying a target nucleic acid, which can minimize dependence on the target nucleic acid, and a method for amplifying a target nucleic acid, which can effectively adjust the sensitivity of target nucleic acid amplification while minimizing effects on the amplification efficiency of the nucleic acid.

Another object of the present invention is to provide a polymerase chain reaction (PCR) composition for amplifying a target nucleic acid, which can minimize dependence on the target nucleic acid and effectively adjust the sensitivity of target nucleic acid amplification.

To achieve the above objects, the present invention provides a method for amplifying a target nucleic acid, the method comprising steps of: (a) isolating a nucleic acid from a sample; (b) performing a polymerase chain reaction (PCR) by adding i) at least one target-specific primer capable of hybridizing with the target nucleic acid, ii) at least one surrogate target comprising a sequence that binds to a target nucleic acid region to which the target-specific primer does not bind and an arbitrary sequence that does not bind to the target nucleic acid, and iii) at least one amplification primer capable of amplifying the surrogate target; and (c) determining the presence or absence of a fusion amplicon.

The present invention also provides a polymerase chain reaction composition for amplifying a target nucleic acid, the composition comprising: i) at least one target-specific primer capable of hybridizing with the target nucleic acid; ii) at least one surrogate target comprising a sequence that binds to a target nucleic acid region to which the target-specific primer does not bind and an arbitrary sequence that does not bind to the target nucleic acid; and iii) at least one amplification primer capable of amplifying the surrogate targets.

BRIEF DESCRIPTION OF DRAWINGS

FIG. 1(a) shows the case in which a target-specific primer and a surrogate target bind to the same target nucleic acid strand, and FIG. 1(b) shows the case in which a target-specific primer and a surrogate target bind to different target nucleic acid strands.

FIG. 4(a) shows the hybridizing relationship between a target nucleic acid, a target-specific primer, a surrogate target, and an amplification primer; FIG. 4(b) shows that the opposite nucleic acid strand of the surrogate target is synthesized by the amplification primer; FIGS. 4(c) and 4(d) show that the opposite nucleic acid strand of the surrogate target synthesized in FIG. 4(b) is extended after binding to the target nucleic acid; FIGS. 4(e) and 4(f) show that the target-specific primer is extended after binding to the opposite strand of the extended surrogate target synthesized in FIG. 4(d); and FIG. 4(g) shows that another target-specific primer and another amplification primer bind to the opposite strand of the extended surrogate target and the extended strand of the target-specific primer, synthesized in FIGS. 4(d) and 4(f), and the synthesis process is repeatedly performed.

FIG. 5(a) shows the hybridizing relationship between a target nucleic acid, a target-specific primer, a surrogate target, and an amplification primer; FIG. 5(b) shows that the target-specific primer bound to the target nucleic acid and the amplification primer bound to the surrogate target are extended to synthesize new nucleic acid strands; FIG. 5(c) shows that the extended strand of the target specific primer and the extended strand of the amplification primer, synthesized in FIG. 5(b), are separated, and then hybridization therebetween occurs and fusion amplicon production starts; FIG. 5(d) shows a completely produced fusion amplicon; and FIG. 5(e) shows that another target-specific primer and another amplification primer bind to the fusion amplicon produced in FIG. 5(d), and the synthesis process is repeatedly performed.

FIG. 6(a) shows the hybridizing relationship between a target nucleic acid, a target-specific primer, a surrogate target, and an amplification primer; FIG. 6(b) shows that the target-specific primer bound to the target nucleic acid and the amplification primer bound to the surrogate target are extended to synthesize new nucleic acid strands; FIGS. 6(c) and 6(d) show that the extended strand of the amplification primer, synthesized in FIG. 6(b), is additionally extended after binding to another target nucleic acid; FIGS. 6(e) and 6(f) show that the target-specific primer is extended after binding to the extended strand of the amplification primer, additionally extended in FIG. 6(d); and FIG. 6(g) shows that another target-specific primer and another amplification primer bind to the extended strand of the amplification primer and the extended strand of the target-specific primer, synthesized in FIGS. 6(d) and 6(f), and the synthesis process is repeatedly performed.

FIG. 7(a) shows the hybridization relationship between a target nucleic acid, a target-specific primer, a surrogate target, and an amplification primer; FIG. 7(b) shows that the target-specific primer bound to the target nucleic acid and the surrogate target are extended to synthesize new strands; FIGS. 7(c) and 7(d) show that another target-specific primer is extended to binding to the extended strand of the surrogate target, synthesized in FIG. 7(b); and FIG. 7(e) shows that another target-specific primer and another amplification primer bind to the extended strand of the surrogate target and the extended strand of the target-specific primer, synthesized in FIGS. 7(b) and 7(d), and the synthesis process is repeatedly performed.

FIG. 15A-FIG. 15L show the results of multiple amplification and detection of the EGFR gene and the HRAS gene in the human genome in an Example of the present invention, and compares a target nucleic acid amplification method of the present invention with a conventional target nucleic acid amplification method under a condition in which the addition amount of an EGFR gene target is larger than that of an HRAS gene target (FIG. 15A-FIG. 15F), and under a condition in which the addition amount of the HRAS gene target is larger than that of the EGFR gene target (FIG. 15G-FIG. 15L).

DETAILED DESCRIPTION AND PREFERRED EMBODIMENTS OF THE INVENTION

Unless otherwise defined, all technical and scientific terms used in the present specification have the same meanings as commonly understood by those skilled in the art to which the present disclosure pertains. In general, the nomenclature used in the present specification is well known and commonly used in the art.

In the present invention, it was examined whether a target nucleic acid can be amplified in a state in which dependence on the target nucleic acid is minimized. That is, in an Example of the present invention, for the region around codon 790 of exon 20 of the human EGFR gene, a polymerase chain reaction (PCR) was performed by adding a target-specific primer capable of binding to the sense strand of the target nucleic acid, a surrogate target comprising a sequence complementary to the target nucleic acid sequence, which corresponds to the downstream region of the target-specific primer, and an arbitrary sequence, and an amplification primer capable of binding to the arbitrary sequence of the surrogate target.

Figure 9A:
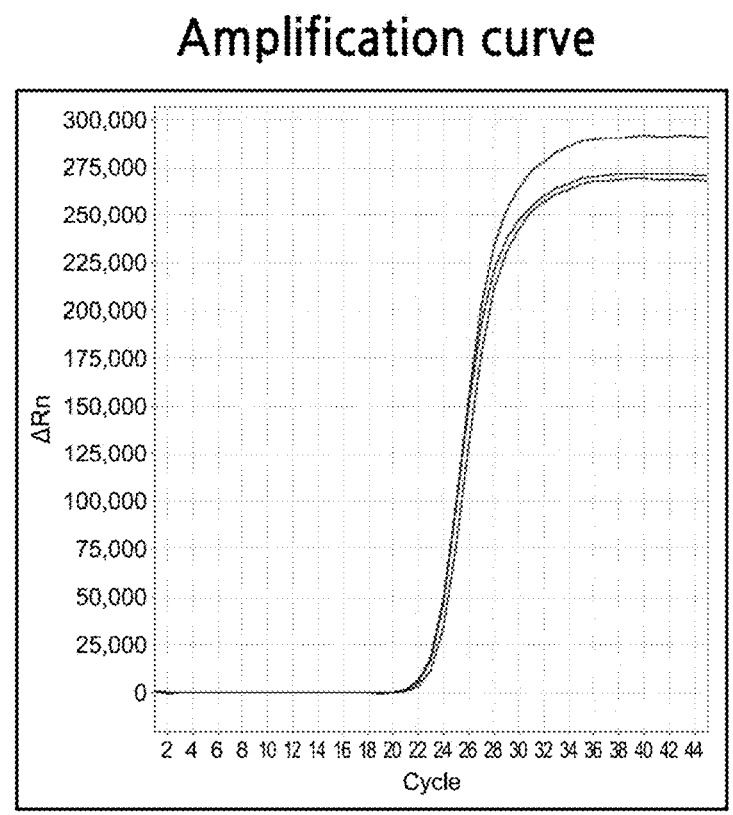
FIG. 9A and FIG. 9B show the results of amplifying and detecting the epidermal growth factor receptor (EGFR) gene in the human genome in an Example of the present invention.
Figure 9A:
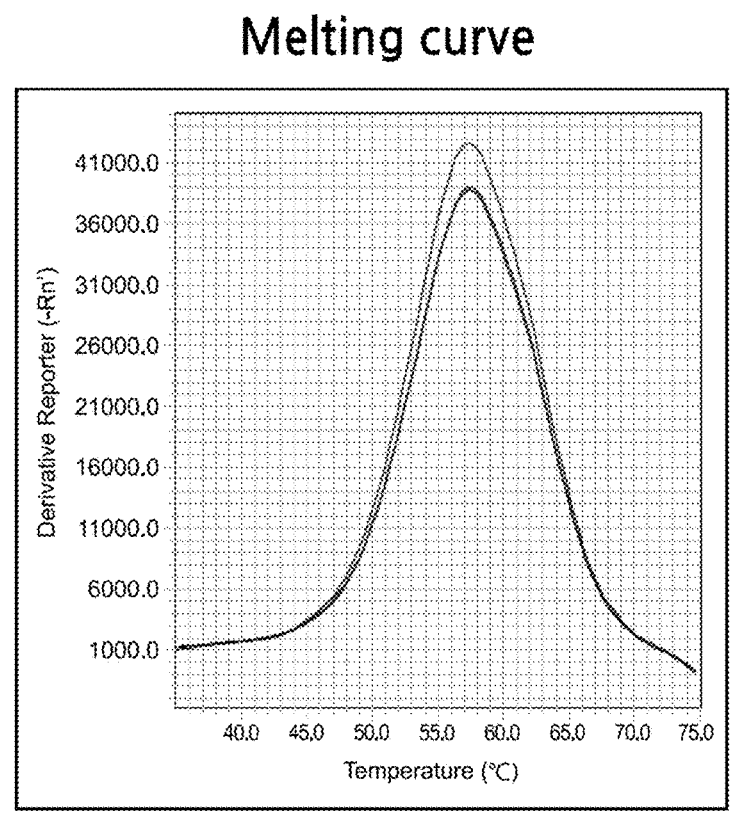
Figure 9B:
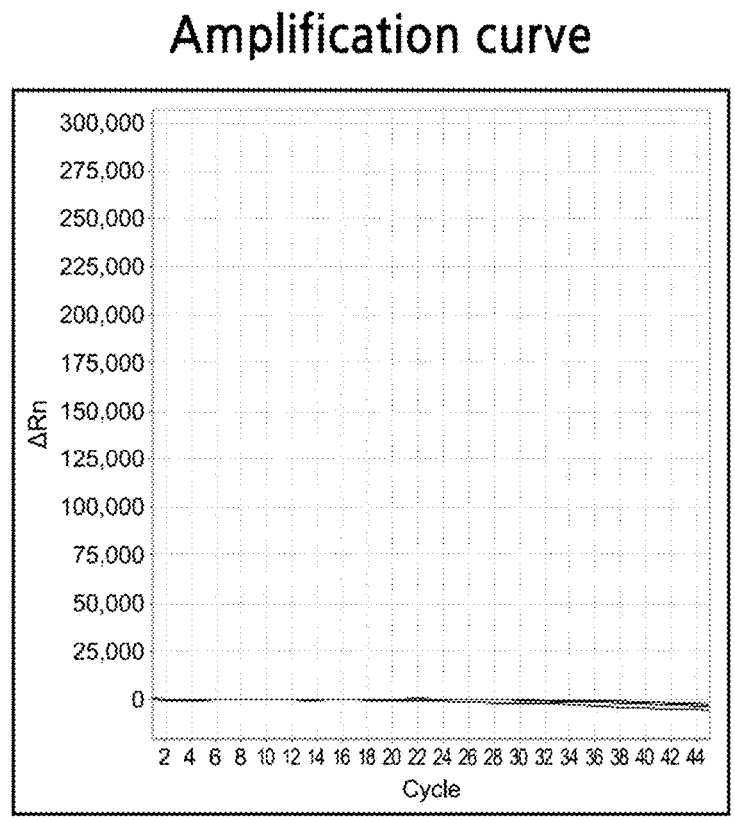
Figure 9B:
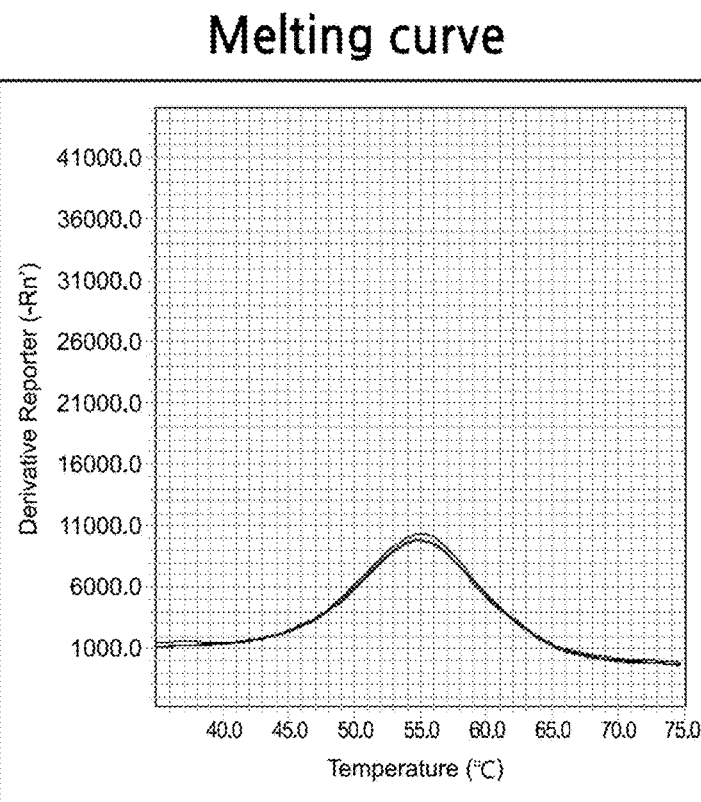
Figure 10A:
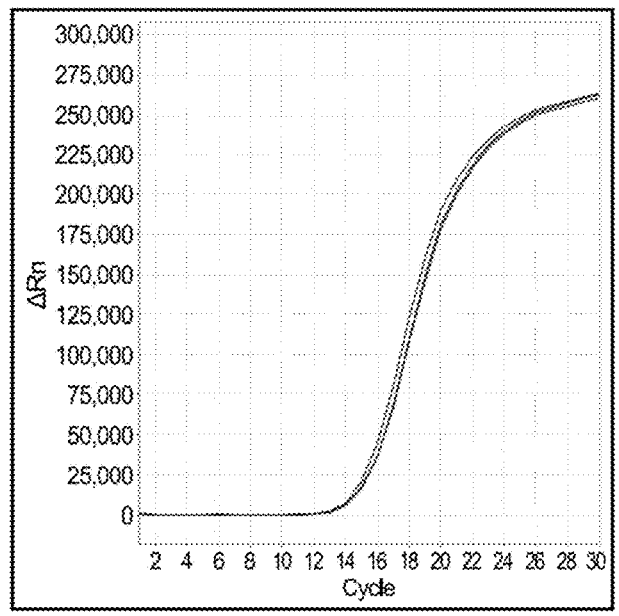
FIG. 10A-FIG. 10E show the results of amplifying and detecting the epidermal growth factor receptor (EGFR) gene in the human genome using an assistant primer in an Example of the present invention.
Figure 10A:
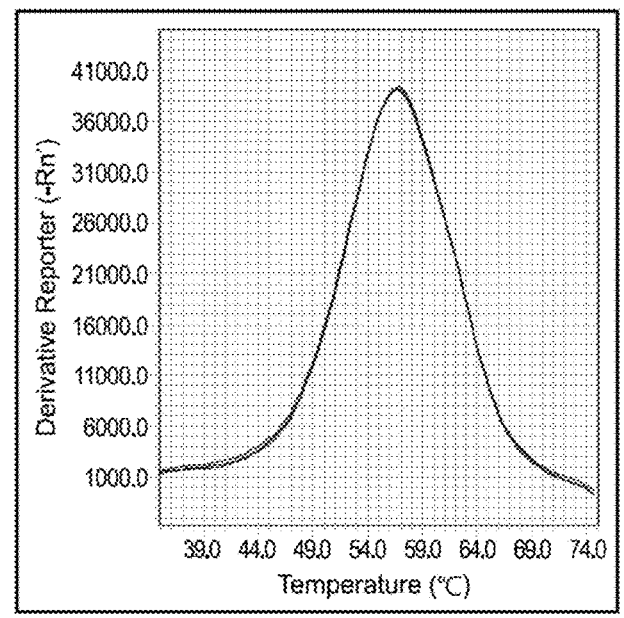
Figure 10B:
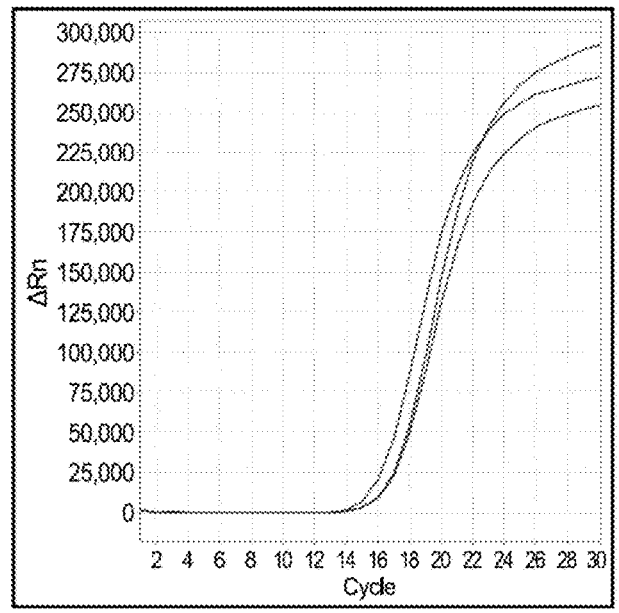
Figure 10B:
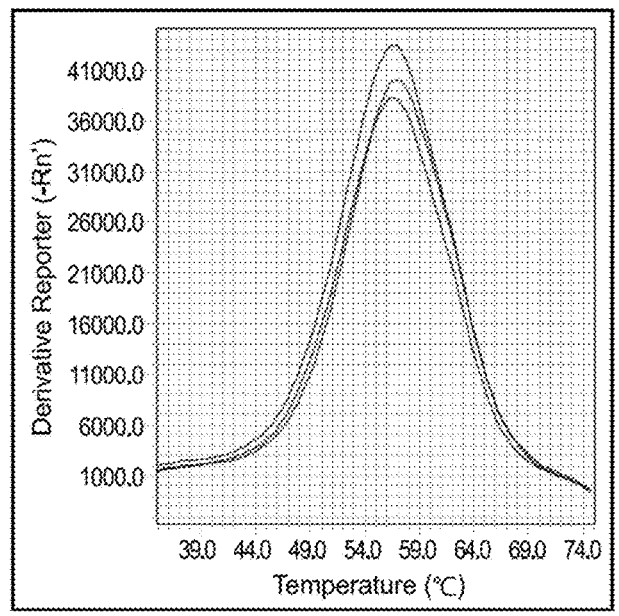
Figure 10C:
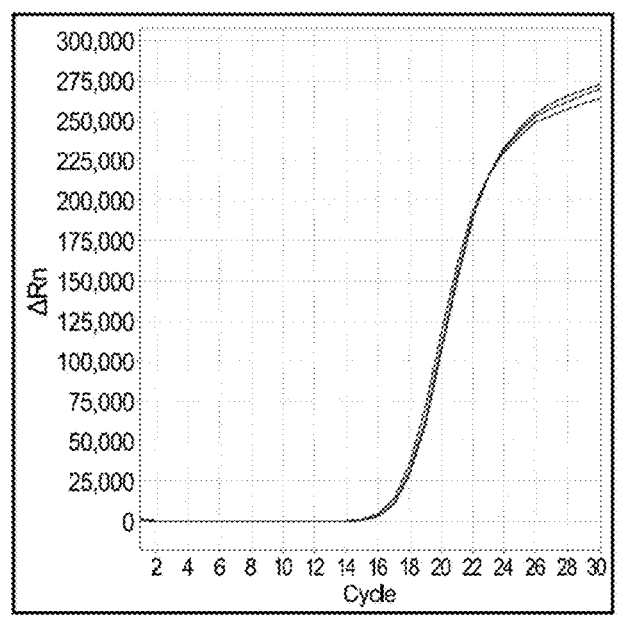
Figure 10C:
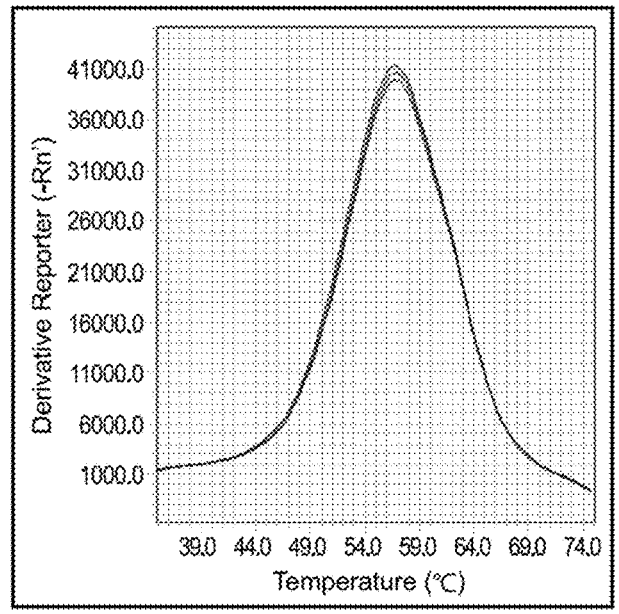
Figure 10D:
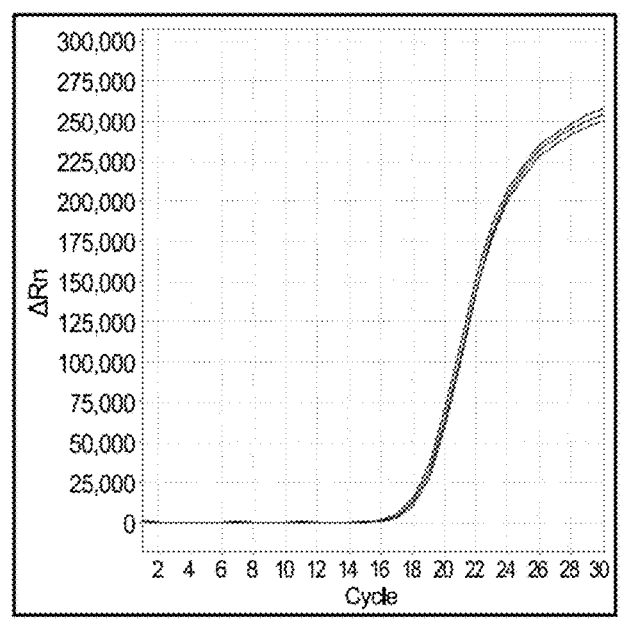
Figure 10D:
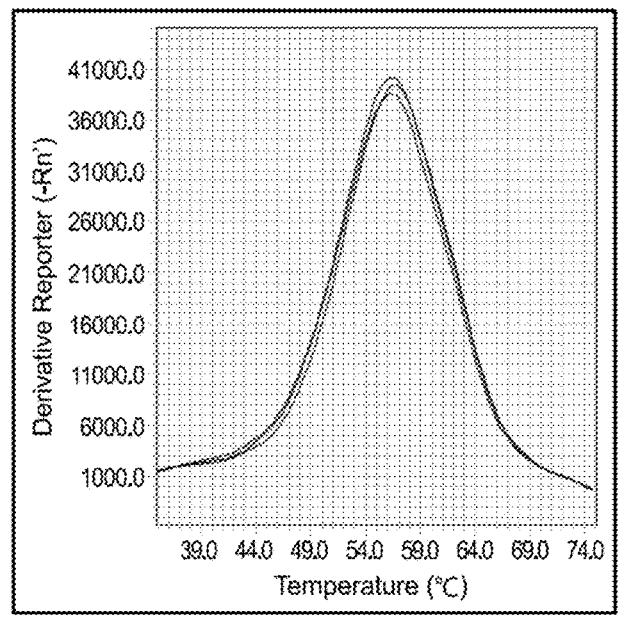
Figure 10E:
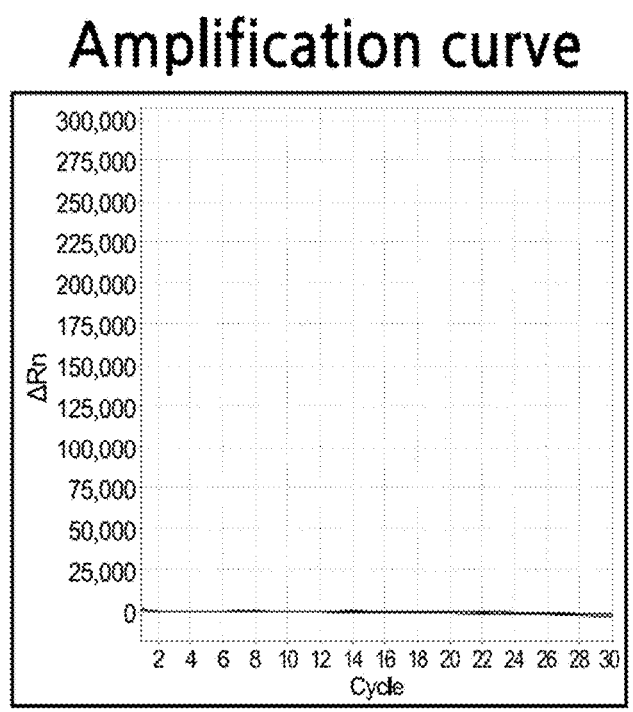
Figure 10E:
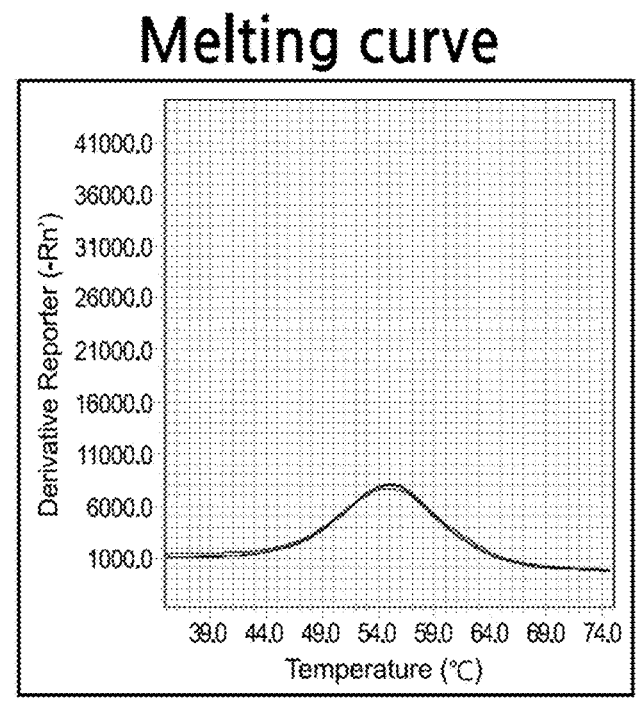
Figure 11A:
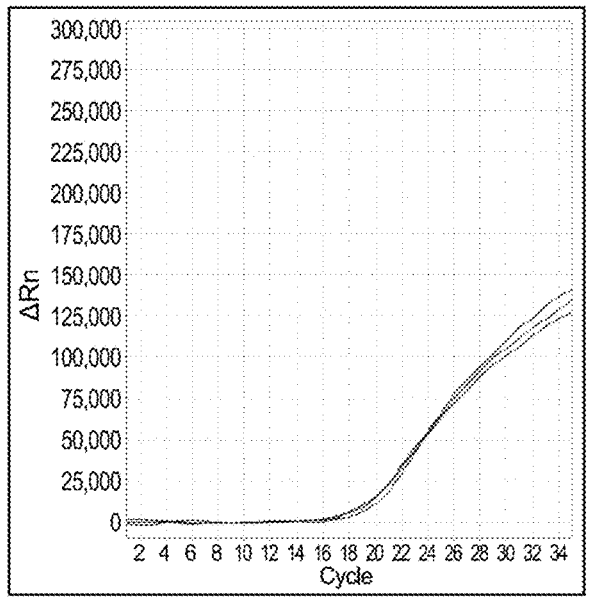
FIG. 11A-FIG. 11H show the results of amplifying and detecting the epidermal growth factor receptor (EGFR) gene in the human genome using various types of surrogate targets in an Example of the present invention.
Figure 11A:
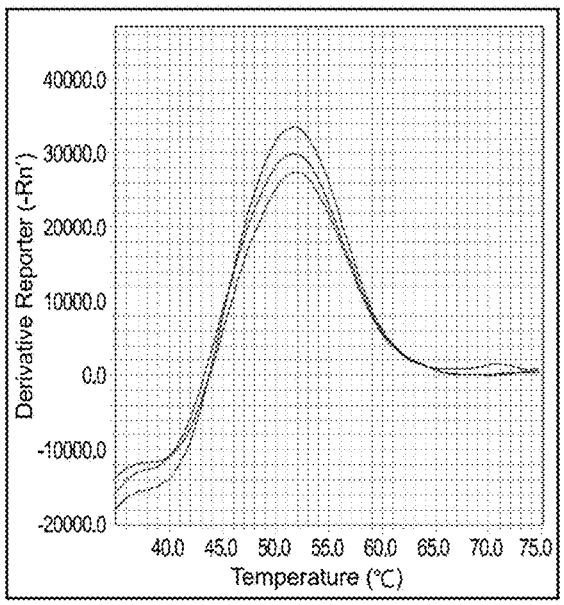
Figure 11B:
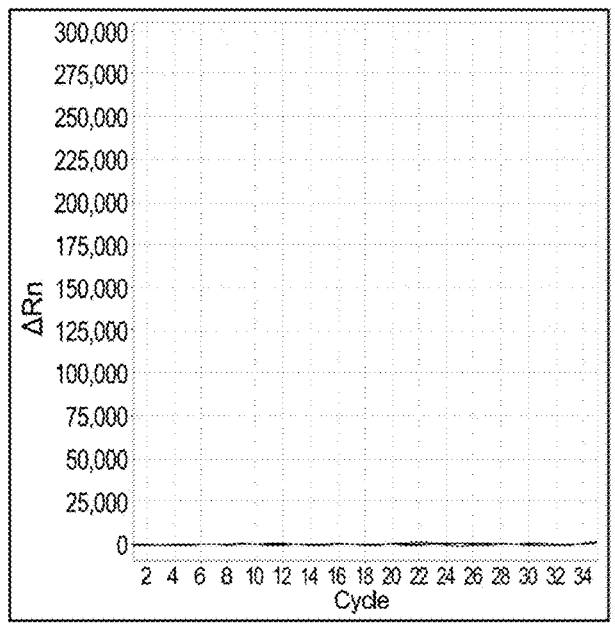
Figure 11B:
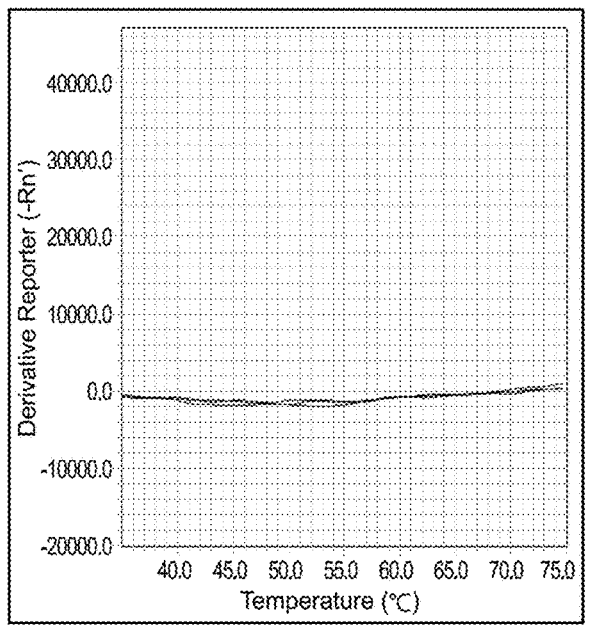
Figure 11C:
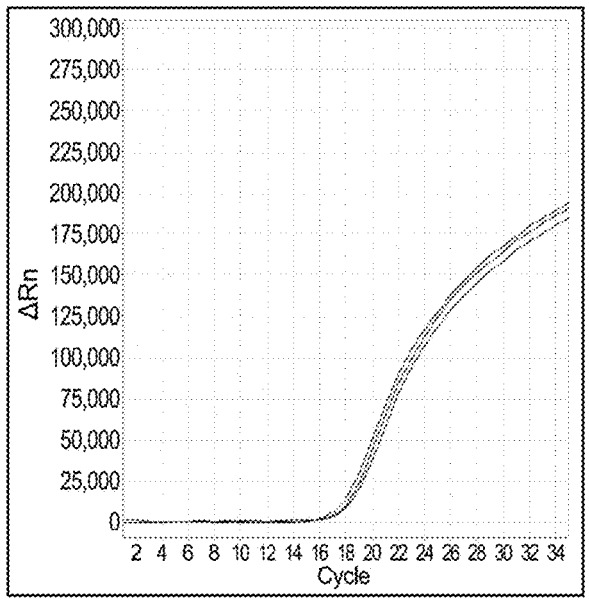
Figure 11C:
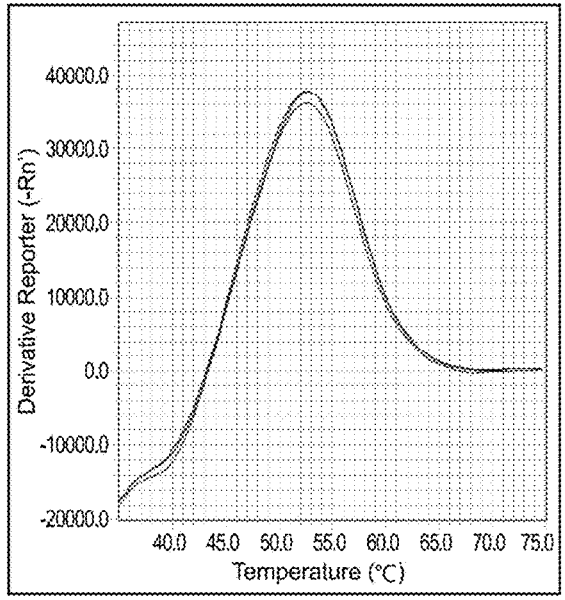
Figure 11D:
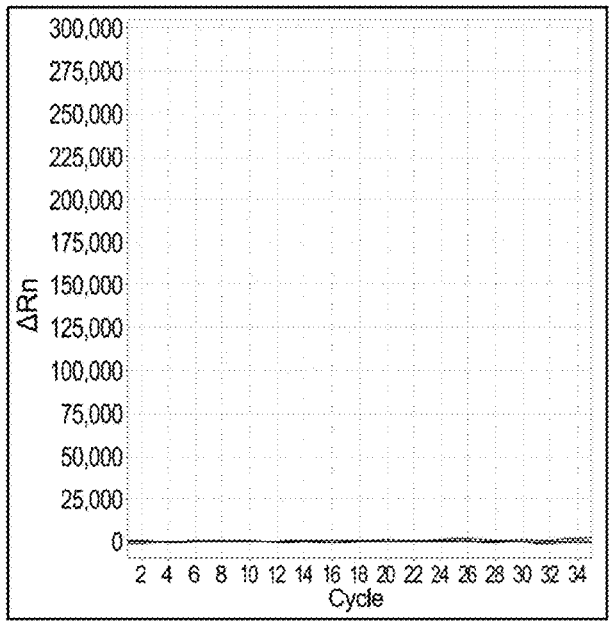
Figure 11D:
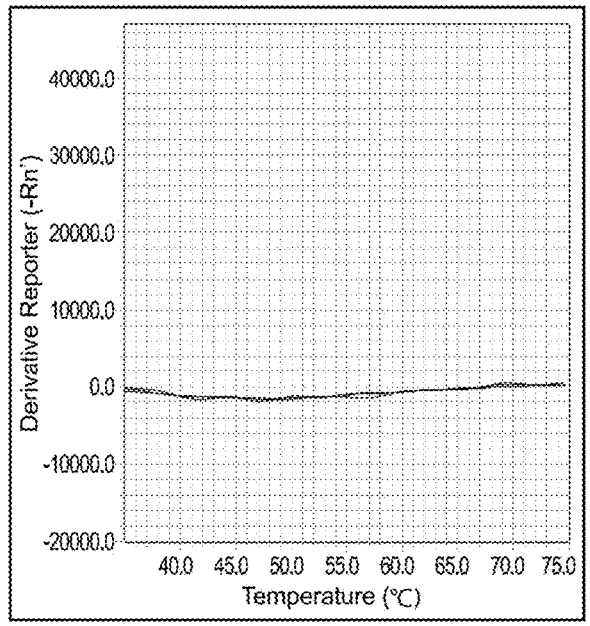
Figure 11E:
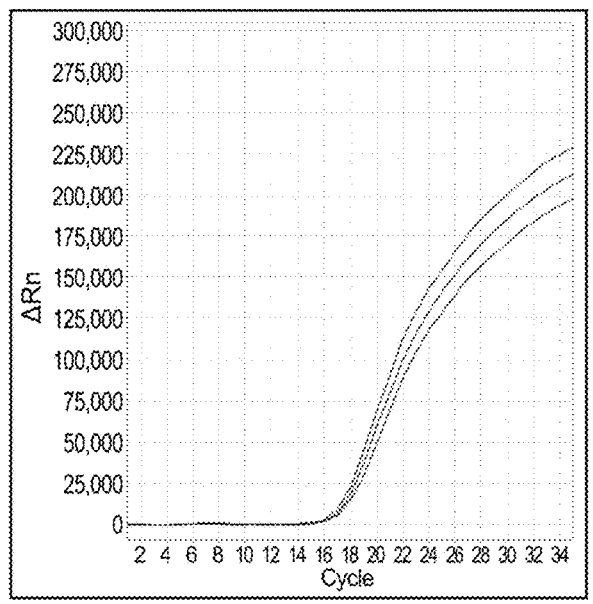
Figure 11E:
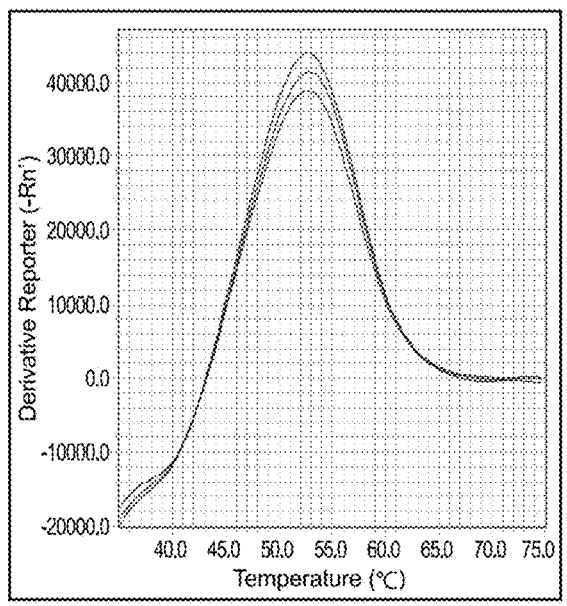
Figure 11F:
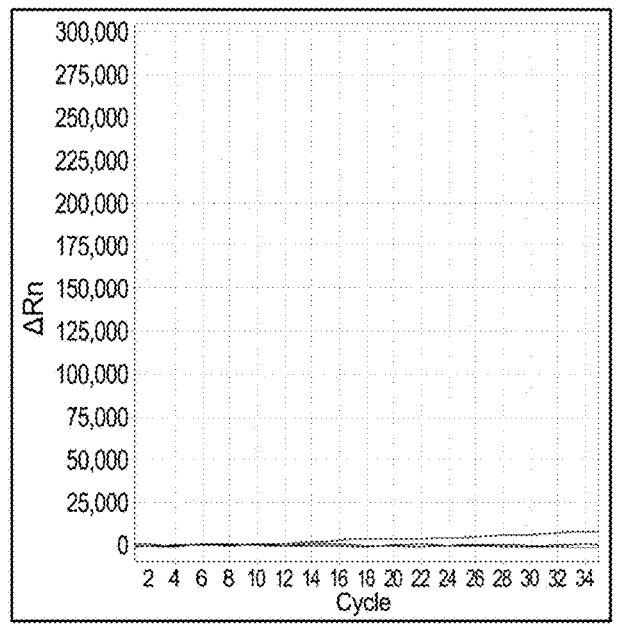
Figure 11F:
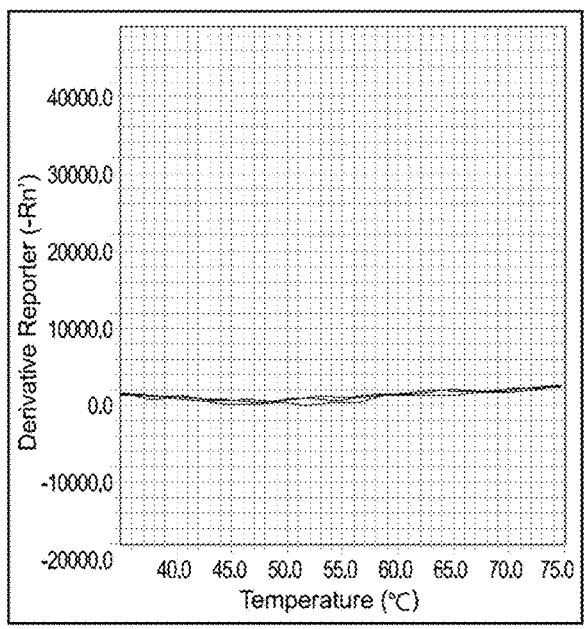
Figure 11G:
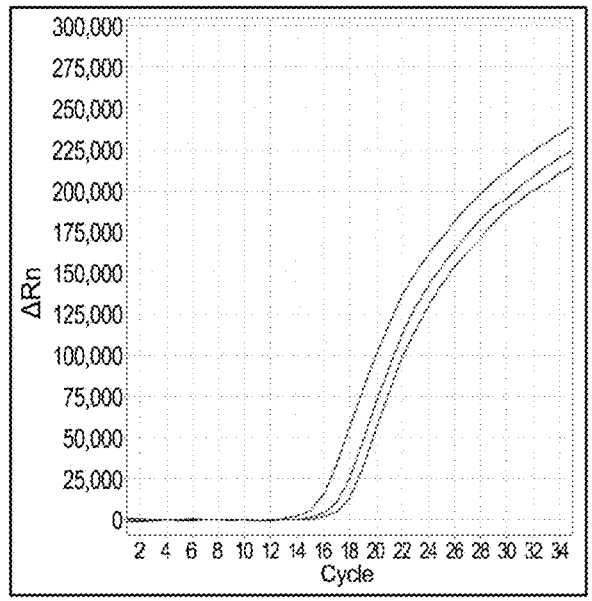
Figure 11G:
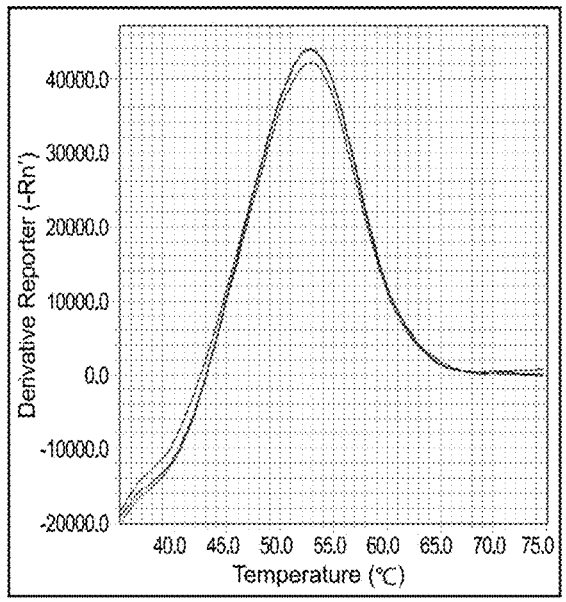
Figure 11H:
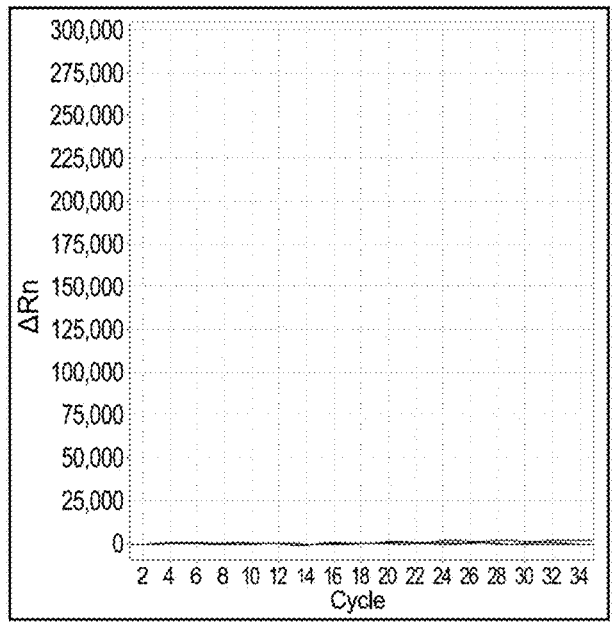
Figure 11H:
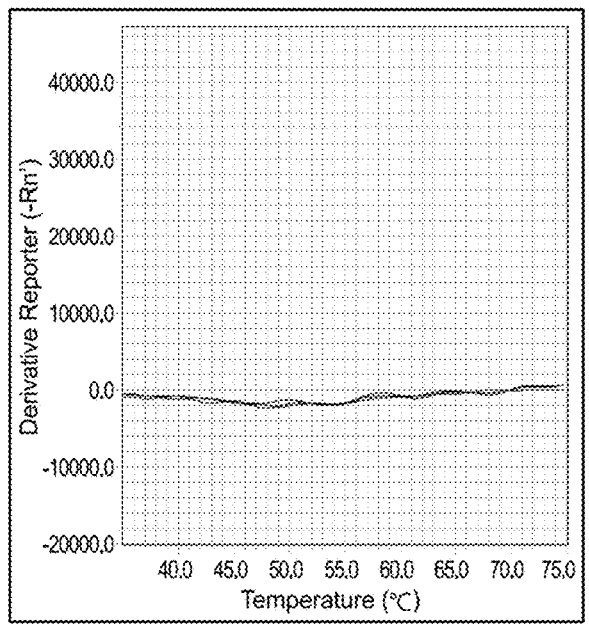

As a result, it could be confirmed that a fusion amplicon between the region around codon 790 of exon 20 of the human EGFR gene and the surrogate target was normally formed, and thus the fusion amplicon was detected by a detection probe (FIG. 9A and FIG. 9B). In addition, an assistant primer capable of binding to the antisense strand of the target nucleic acid was additionally added, and as a result, it was confirmed that the sensitivity of detection of the human EGFR gene was about 10 copies per reaction, suggesting that the gene could be detected with very high sensitivity (FIG. 10A-FIG. 10E).

In another Example of the present invention, for the region around codons 12 and 13 of exon 2 of the human HRAS gene, which is difficult to amplify by a conventional polymerase chain reaction because the average guanine/cytosine (G/C) content is high, a polymerase chain reaction was performed by adding a target-specific primer capable of binding to the sense strand of the target nucleic acid, a surrogate target comprising a sequence complementary to the antisense strand of the target nucleic acid sequence, which corresponds to the downstream region of the target-specific primer, and an arbitrary sequence, an amplification primer having the same sequence as a portion of the arbitrary sequence of the surrogate target, and an assistant primer capable of binding to the antisense strand of the target nucleic acid.

As a result, the region of codons 12 and 13 of exon 2 of the HRAS gene could be detected with a higher amplification efficiency and accuracy than a conventional method in which the surrogate target and the amplification primer are not added (FIG. 13A-FIG. 13F).

In addition, in the present invention, it was examined whether effects on the amplification efficiency of the target nucleic acid can be minimized when the detection sensitivity of the target nucleic acid is arbitrarily adjusted.

That is, in an Example of the present invention, for the region around codon 790 of exon 20 of the EGFR gene, a polymerase chain reaction was performed by adding a target-specific primer capable of binding to the sense strand of the target nucleic acid, various amounts (0.01 fmole, 0.1 fmole, 1 fmole, and 10 fmole) of a surrogate target comprising a sequence complementary to the target nucleic acid sequence, which corresponds to the downstream region of the target-specific primer, and an arbitrary sequence, an amplification primer capable of binding to the arbitrary sequence of the surrogate target, and an assistant primer capable of binding to the antisense strand of the target nucleic acid.

Figure 14A:
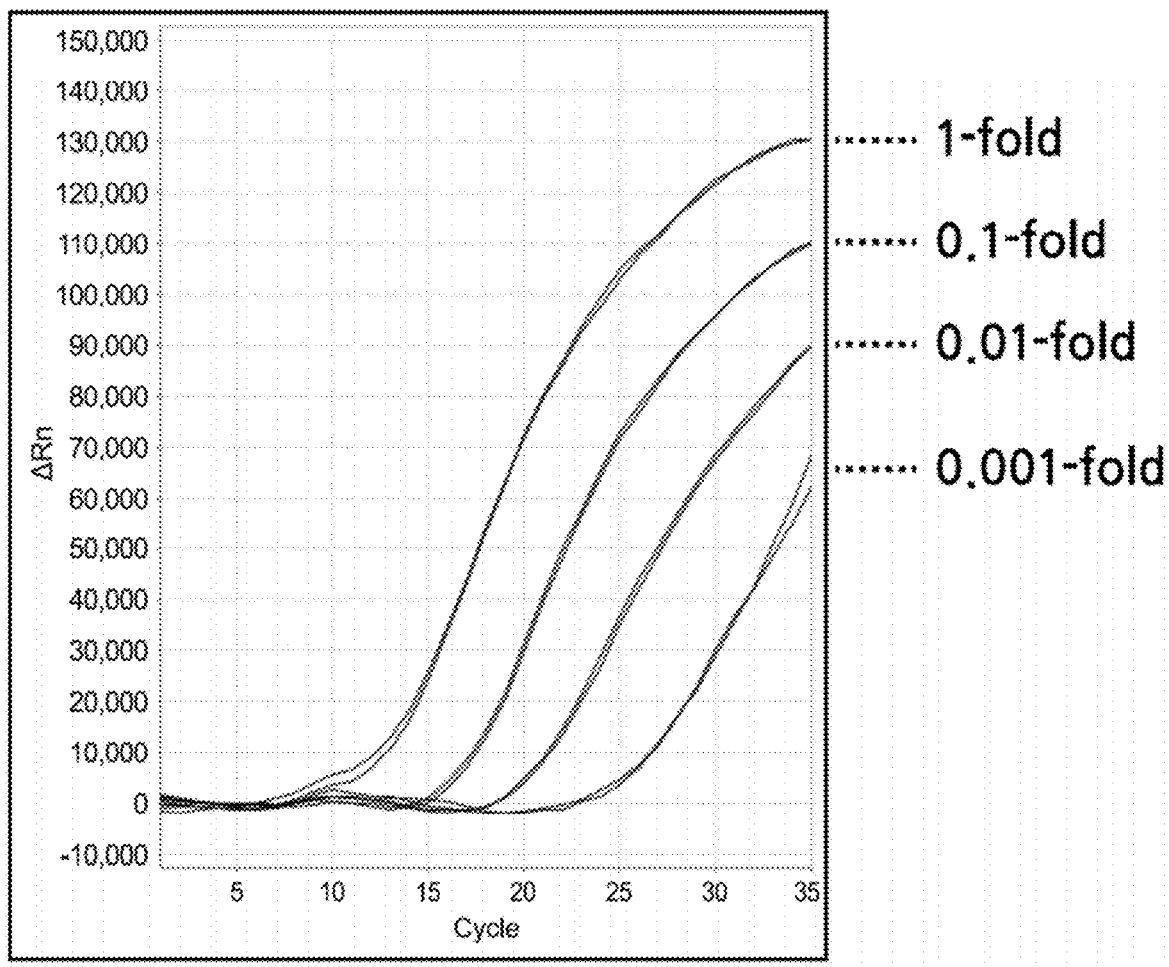
FIG. 14A and FIG. 14B show the results of adjusting the sensitivity of detection of the epidermal growth factor receptor (EGFR) gene in the human genome in an Example of the present invention, and compares a sensitivity adjustment method of the present invention (FIG. 14A) with a conventional sensitivity adjustment method (FIG. 14B).
Figure 14B:
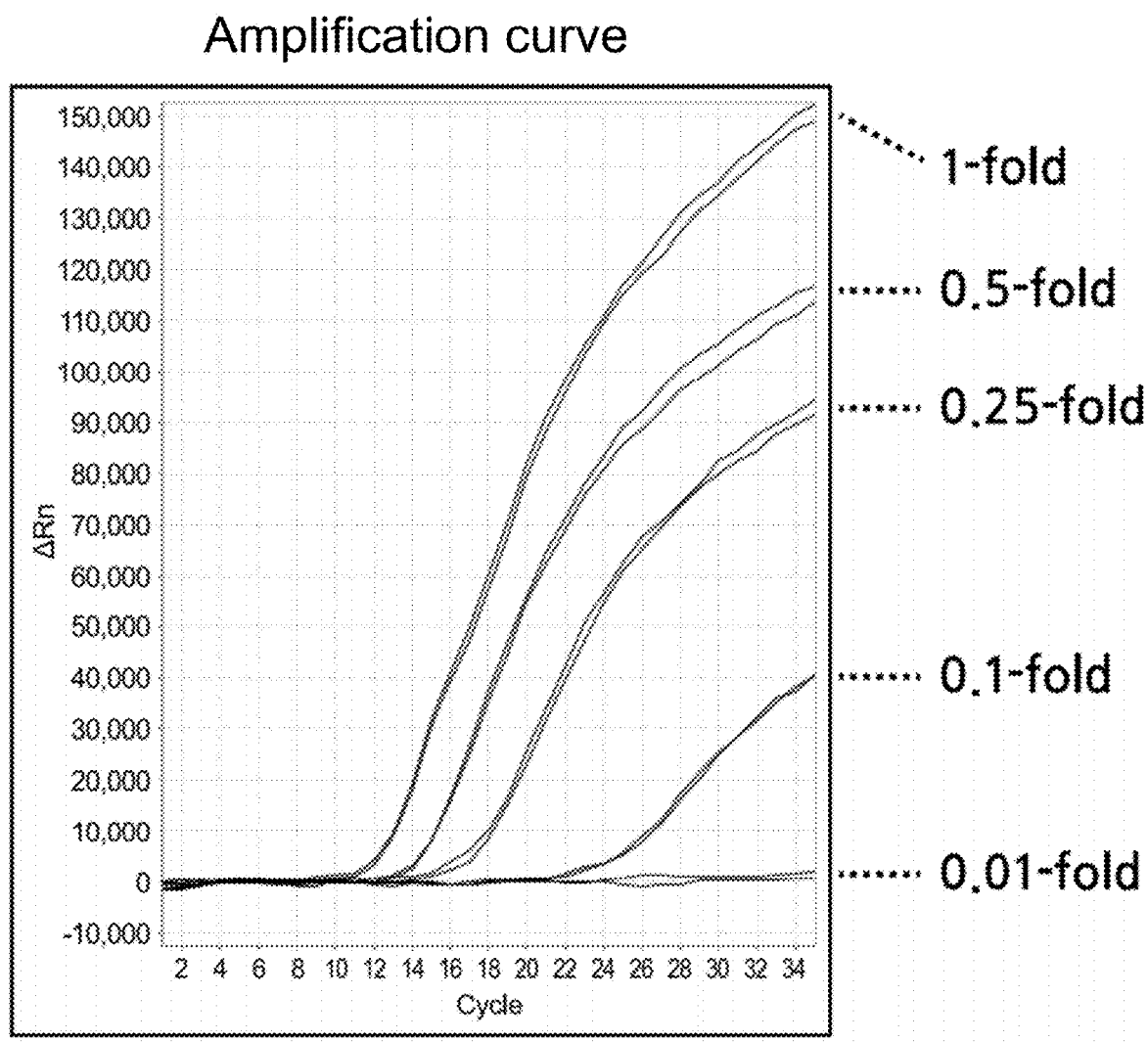
Figure 15A:
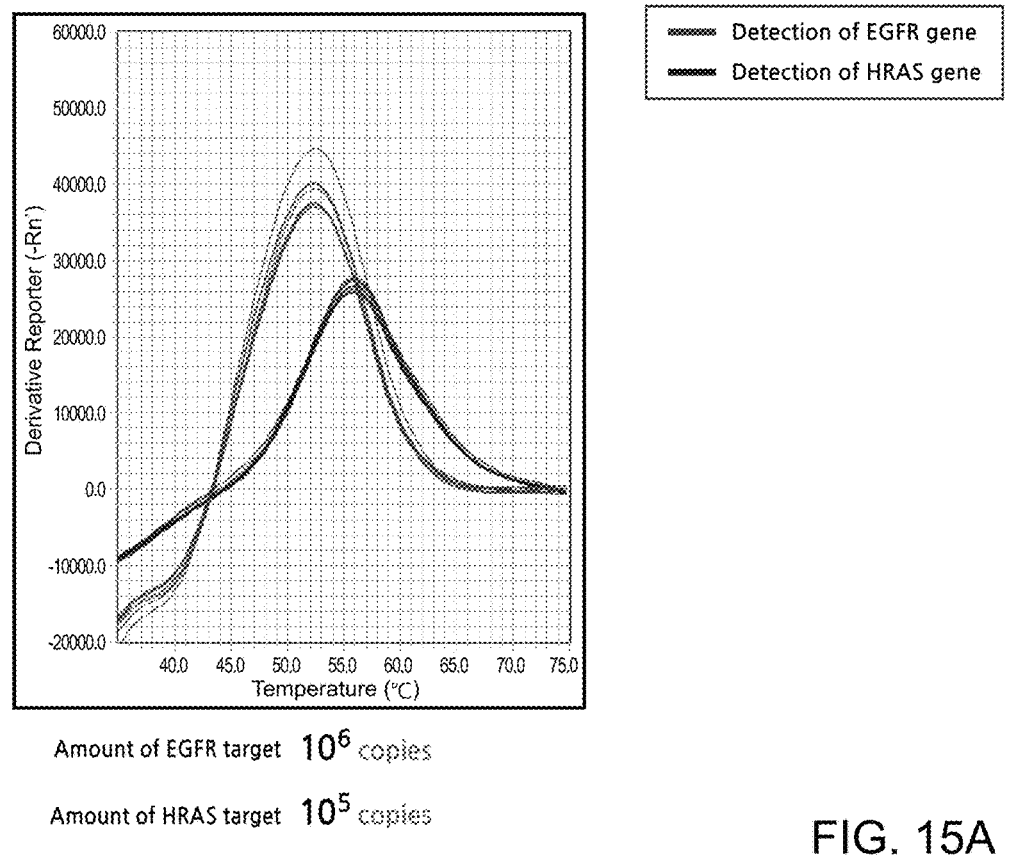
Figure 15A:
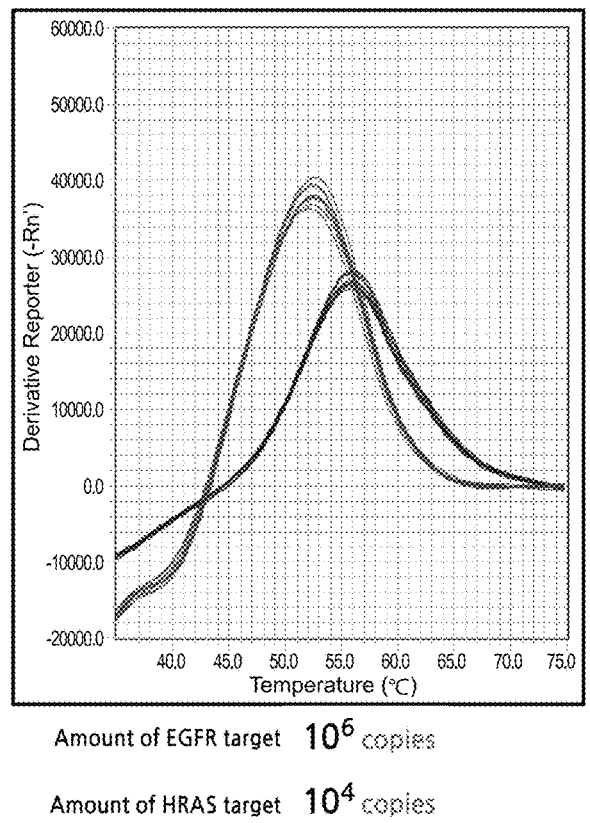

As a result, it could be confirmed that, in contrast to a conventional method in which, when the detection sensitivity of the target nucleic acid is adjusted by increasing or decreasing the concentration of the primer, the amplification efficiency of the nucleic acid is also changed, the amplification efficiency of the nucleic acid was maintained constant when the detection sensitivity of the target nucleic acid was adjusted by controlling the amount of surrogate target added (FIG. 14A and FIG. 14B).

Therefore, in one aspect, the present invention provides a method for amplifying a target nucleic acid, the method comprising steps of: (a) isolating a nucleic acid from a sample; (b) performing polymerase chain reaction (PCR) by adding i) at least one target-specific primer capable of hybridizing with the target nucleic acid, ii) at least one surrogate target comprising a sequence that binds to a target nucleic acid region to which the target-specific primer does not bind and an arbitrary sequence that does not bind to the target nucleic acid, and iii) at least one amplification primer capable of amplifying the surrogate targets; and (c) determining the presence or absence of a fusion amplicon.

As used herein, the term "target nucleic acid" refers to all types of nucleic acids to be detected, and includes gene sequences derived from different species, subspecies, or variants, or gene mutations in the same species. The term may include all types of DNA, including genomic DNA, mitochondrial DNA, and viral DNA, or all types of RNA, including mRNA, ribosomal RNA, non-coding RNA, tRNA, and viral RNA, but is not limited thereto. The target nucleic acid hybridizes with the target-specific primer, the assistant primer and the surrogate target under conditions for polymerase chain reaction, and the probe may also hybridize to part or all of the target nucleic acid.

As used herein, the term "hybridization" means that a double-stranded nucleic acid is formed by hydrogen bonding between single-stranded nucleic acids having complementary base sequences, and is used in a sense similar to annealing. However, in a slightly broader sense, hybridization includes not only the case where the nucleotide sequences of two single strands perfectly match, but also an exceptional case in which some nucleotide sequences mismatch.

As used herein, the term "target-specific primer" refers to a primer capable of hybridizing with the target nucleic acid and forming and amplifying the fusion amplicon through polymerase chain reaction.

As used herein, the term "amplification primer" refers to a primer that may hybridize with a portion of the arbitrary sequence of the surrogate target when the surrogate target hybridizes with the same target nucleic acid strand with which the target-specific primer hybridizes, and may form and amplify the fusion amplicon. Also, the term "amplification primer" refers to a primer of the same sequence as a portion of the arbitrary sequence of the surrogate target when the surrogate target hybridizes with a strand opposite the target nucleic acid strand with which the target-specific primer hybridizes, and may form and amplify the fusion amplicon.

In the present invention, the amplification primer may function as a universal primer. That is, if there are several types of target nucleic acids to be amplified, several types of targets can be simultaneously amplified with one amplification primer. That is, in conventional multiplex PCR, the same number of forward and reverse primer pairs as the number of targets to be detected should be prepared and used at the same time, whereas, in the method of the present invention, the same number of forward primers (target-specific primers) as the number of targets to be detected are used in a real-time PCR process for simultaneously detecting multiple target DNAs, and only one reverse primer (amplification primer) may be used as a universal primer, and thus only a small number of primers may be used to detect multiple targets, so that PCR complexity and variations in PCR efficiency are reduced.

As used herein, the term "fusion amplicon" refers to a product which is formed and amplified by the target-specific primer, the surrogate target and the amplification primer and consists of a fusion of a portion of the target nucleic acid and a portion or all of the surrogate target. In a preferred embodiment, formation of the fusion amplicon may be induced by the 5'-3' exonuclease activity or flap endonuclease activity of polymerase, but is not limited thereto.

In the present invention, a target nucleic acid region to which the target-specific primer does not bind may be present downstream of the target-specific primer, and the downstream direction of the target-specific primer may be a direction in which the target-specific primer is extended by PCR after binding to the target nucleic acid.

In the present invention, the surrogate target is preferably paired with the target-specific primer, but is not limited thereto.

In the present invention, any method may be used in order for the surrogate target not to function as a primer if necessary. Preferably, the arbitrary sequence that does not bind to the target nucleic acid may be located at the 3' end or 5' end of the surrogate target, or a functional group or an oligonucleotide for inhibiting nucleic acid polymerization may additionally be included at the 3' end of the surrogate target.

In the present invention, the functional group or the oligonucleotide for inhibiting nucleic acid polymerization may be one or more selected from the group consisting of an amine group, a phosphate group, an alkyl group, alkane-diol, phosphorothioate, biotin, a non-nucleotide linker, a C3-18 spacer, di-deoxynucleotide triphosphate (ddNTP), inverted deoxynucleotide triphosphate (inverted dNTP), and inverted di-deoxynucleotide triphosphate (inverted ddNTP), but is not limited thereto.

In the present invention, each of the target-specific primer, the surrogate target and the amplification primer may be composed of any one or a mixture of two or more of an oligonucleotide, LNA (locked nucleic acid), and PNA (peptide nucleic acid).

In the present invention, the surrogate target may be used without limitation as long as it is a nucleic acid that induces formation of a fusion amplicon by the target-specific primer and the amplification primer while being capable of hybridizing with the target nucleic acid. Preferably, the surrogate target may be an oligonucleotide prepared to have a length of 10 to 500 nucleotides. More preferably, the surrogate target may be a single-stranded oligonucleotide prepared to have a length of 20 to 150 nucleotides.

In the present invention, the ratio of a portion of the surrogate target, which binds to the target nucleic acid, to the arbitrary sequence of the surrogate target, may be 6:4 to 2:8, but is not limited thereto.

In the present invention, the portion of the surrogate target, which binds to the target nucleic acid, may comprise a 10- to 50-nucleotide sequence having a melting temperature (Tm) of 40 to 80° C., but is not limited thereto.

In the present invention, the arbitrary sequence of the surrogate target may be a 10- to 100-nucleotide sequence, and may be arbitrarily determined so as not to be complementary to the target nucleic acid or may be determined from genomic nucleotide sequences derived from species different from the species of the target nucleic acid, but is not limited thereto.

In the present invention, the surrogate target may further comprise a spacer which is a single-stranded oligonucleotide. The spacer may be a 1- to 100-nucleotide sequence, more preferably a 2- to 20-nucleotide sequence.

In the present invention, the GC content of the spacer may be 30% or less, more preferably 5 to 30%, most preferably 1 to 10%.

In the present invention, the term "spacer" refers to a sequence except a sequence with which the amplification primer hybridizes or which is included in the amplification primer in the arbitrary sequence included in surrogate target. The spacer functions to prevent sequence regions of the surrogate target, with which the target nucleic acid and the amplification primer hybridizes, or which is included in the amplification primer from being excessively close to each other or from overlapping each other. The spacer functions to control GC contents of the fusion amplicon. In addition, even when, if necessary, by using a probe capable of binding to the spacer, same probe may detect different target nucleic acids.

In one Example of the present invention, it was confirmed that, when a surrogate target having no spacer was used, the efficiency of amplification decreased.

In the present invention, the surrogate target may hybridize with a strand of the target nucleic acid, which is the same as or opposite the strand with which the target-specific primer hybridizes.

In the present invention, the fusion amplicon may be 50 bp to 1 kbp in length and may have a GC content of 35 to 65%, more preferably 40 to 60%.

In the present invention, the target-specific primer may not be complementary to the surrogate target, and may not hybridize with the surrogate target, or even when it partially hybridizes with the surrogate target, synthetic elongation of the nucleic acid may not occur. The amplification primer may not be complementary to the target nucleic acid, and may not hybridize with the target nucleic acid, and even when it partially hybridizes with the target nucleic acid, synthetic elongation of the nucleic acid may not occur.

In the present invention, step (c) of determining the presence or absence of the fusion amplicon may be performed using a nucleic acid-binding dye or probe capable of binding to the fusion amplicon.

In the present invention, the nucleic acid-binding dye may be used without limitation as long as it is an intercalating agent or a DNA minor groove-binding agent. Preferably, the nucleic acid-binding dye may be selected from the group consisting of ethidium bromide, SYBR® Green I, SYBR® Gold, EvaGreen, YO-PRO-1, SYTO, BEBO, and BEXTO.

In the present invention, the probe capable of binding to the fusion amplicon may be selected from the group consisting of an oligonucleotide, LNA, PNA, and mixtures thereof.

PNA (peptide nucleic acid) is a DNA analogue containing nucleic acid bases linked by a peptide backbone rather than by a sugar-phosphate backbone, and was first synthesized by Nielsen et al in 1991. PNA is artificially synthesized as one of gene recognition agents, like LNA (locked nucleic acid) or MNA (morpholino nucleic acid), and has a basic backbone composed of polyamide.

PNA has excellent affinity and selectivity, and is highly stable to nucleases, and thus is not degraded by existing restriction enzymes. In addition, it has an advantage in that it has excellent physical properties and is thermally/chemically highly stable, and thus is easy to store for a long period of time.

PNA forms a double strand through a hybridization with a natural nucleic acid having a complementary nucleotide sequence. When the length is the same, the PNA/DNA double strand is more stable than a DNA/DNA double strand, and a PNA/RNA double strand is more stable than a DNA/RNA double strand. In addition, PNA has a better ability to detect SNP (single nucleotide polymorphism) than a natural nucleic acid, because double strand instability thereof due to single base mismatch is greater.

That is, PNA-DNA affinity is much higher than DNA-DNA affinity, and despite having one nucleotide mismatch, PNA-DNA generally has a melting temperature (Tm) difference of about 15 to 20° C. Using this difference in binding affinity, it is possible to detect nucleotide sequence changes such as a single-nucleotide polymorphism (SNP) and an insertion/deletion (In/Del).

In the present invention, the probe capable of binding to the fusion amplicon may have a nucleotide sequence that is partially or wholly complementary to any nucleotide sequence in the fusion amplicon including arbitrary nucleotide sequence and the target nucleic acid sequence. Preferably, a reporter and a quencher may be linked to both ends of the probe.

In the present invention, when the distance between the reporter and the quencher in the probe is short, generation of a signal from the probe is inhibited, and as the distance between the reporter and the quencher becomes longer, the intensity of the signal increases. In general, when the probe hybridizes with a complementary nucleotide sequence, the distance between the reporter and the quencher becomes the longest, and thus a specific nucleotide sequence can be detected through an increase in signal generation or an increase in signal intensity.

In the present invention, the reporter may be one or more fluorescent substances selected from the group consisting of fluorescein, fluorescein chlorotriazinyl, rhodamine green, rhodamine red, tetramethylrhodamine, FITC, Oregon green, Alexa Fluor, FAM, JOE, ROX, HEX, Texas Red, TET, TRITC, TAMRA, cyanine-based dyes, and thiadicarbocyanine dyes.

In the present invention, the quencher may be one or more selected from the group consisting of Dabcyl, TAMRA, Eclipse, DDQ, QSY, Blackberry Quencher, Black Hole Quencher, Qxl, Iowa black FQ, Iowa black RQ, and IRDye QC-1.

In a preferred embodiment of the present invention, detection of the fusion amplicon is performed by real-time PCR. Specifically, detection of the fusion amplicon may be performed by measuring a Ct (cycle threshold) value from an amplification curve obtained through amplification of the fusion amplicon, or measuring the melting peak of the probe from a melting curve obtained after polymerase chain reaction, or comprehensively considering the two results from the obtained amplification curve and melting curve, but is not limited thereto.

As the fusion amplicon is amplified earlier due to the presence of the target nucleic acid in the sample, the amount of a signal generated by the detection probe increases earlier, and thus the number of cycles reaching the threshold decreases and a low Ct value is measured. Based on this Ct value, the presence or absence of the target nucleic acid may be determined. Also, melting curve analysis is generally performed after nucleic acid amplification in real-time polymerase chain reaction. Specifically, a signal pattern is measured while the temperature of the sample is decreased to a low temperature (about 25 to 55° C.), and then increased to a high temperature (about 75 to 95° C.) at a rate of 0.3 to 1° C. per 1 to 10 seconds, or while the temperature of the sample is increased to a high temperature, and then decreased to a low temperature at a rate of 0.3 to 1° C. per 1 to 10 seconds. If the fusion amplicon has been amplified, a change in the signal pattern appears at around the melting temperature (Tm) of the probe bound to the fusion amplicon through melting curve analysis, and the fusion amplicon may be identified by analyzing this change as a melting peak.

In the present invention, step (b) may further comprise adding an assistant primer that hybridizes with a strain opposite the target nucleic acid strand with which the target-specific primer hybridizes. That is, if the target-specific primer hybridizes with the sense strand of the target nucleic acid, the assistant primer hybridizes with the antisense strand of the target nucleic acid.

In the present invention, the assistant primer has the effect of increasing the amount of a certain target nucleic acid region by pairing with the target-specific primer. The assistant primer may not be complementary to the surrogate target and may not hybridize with the surrogate target, or even when it partially hybridizes with the surrogate target, synthetic elongation of the nucleic acid may not occur. In the present invention, the main role of the assistant primer is to increase the production rate of the fusion amplicon by increasing the amount (number of copies) of the target nucleic acid under conditions in which the target nucleic acid is present in a very small amount.

If the assistant primer is used in the present invention, the polymerase chain reaction (PCR) may be performed in two steps as follows:

1) a "target nucleic acid amplification step" in which the target-specific primer and the assistant primer are paired with each other to induce a main synthetic reaction; and 2) a "fusion amplicon amplification step" in which the target-specific primer, the surrogate target and the amplification primer act to induce the fusion amplicon to be mainly amplified.

In the present invention, the subdivision of the step is mainly implemented by specifically adjusting the temperature of an annealing step of inducing hybridization between elements during stepwise and repetitive thermal cycling for polymerase chain reaction (PCR). Preferably, in the target nucleic acid amplification step, the temperature of the annealing step may be set high and the melting temperature (Tm) of the target-specific primer and the assistant primer may also be set high so that amplification of the target nucleic acid by the target-specific primer and the assistant primer may occur preferentially. In the fusion amplicon amplification step, the temperature of the annealing step may be lowered and the melting temperature of the amplification primer and target nucleic acid binding site of the surrogate target may be set low, thereby inducing amplification of the fusion amplicon. At this time, if the amount of the assistant primer is limited, the assistant primer is mostly exhausted in the target nucleic acid amplification step, and consequently, it is possible to complete a two-step polymerase chain reaction in which only elements necessary for each step participate in the reaction.

In another aspect, the present invention is directed to a polymerase chain reaction (PCR) composition for amplifying a target nucleic acid, the composition comprising: i) at least one target-specific primer capable of hybridizing with the target nucleic acid; ii) at least one surrogate target comprising a sequence that binds to a target nucleic acid region to which the target-specific primer does not bind and an arbitrary sequence that does not bind to the target nucleic acid; and iii) at least one amplification primer capable of amplifying the surrogate targets.

In the present invention, the composition may further comprise an assistant primer that hybridizes with a strand opposite to a target nucleic acid strand with which the target-specific primer hybridizes. That is, if the target-specific primer hybridizes with the sense strand of the target nucleic acid, the assistant primer may hybridize with the antisense strand of the target nucleic acid.

As used herein, the term "sample" includes various samples. Preferably, biological samples are analyzed using the method of the present invention. More preferably, the samples may be samples containing virus species, or samples from virus-infected individuals (e.g., humans, mammals and fish, etc.), and biological samples of plant, animal, human, fungal, bacterial and viral origins may be analyzed. When a sample of mammalian or human origin is analyzed, the sample may be derived from specific tissue or a specific organ. Typical examples of the tissue include connective tissue, skin tissue, muscle tissue or nerve tissue. Typical examples of the organ include eye, brain, lung, liver, spleen, bone marrow, thymus, heart, lymph, blood, bone, cartilage, pancreas, kidney, gallbladder, stomach, small intestine, testicle, ovary, uterus, rectum, nervous system, gland, and internal blood vessels. The biological samples to be analyzed include any cell, tissue, or fluid from a biological source, or any other medium that can advantageously be analyzed by the present invention, including a sample drawn from a human patient, a sample drawn from an animal, or a sample drawn from food designed for human or animal consumption. In addition, the biological samples to be analyzed include body fluid samples, including, but not limited to, blood, serum, plasma, lymph, breast milk, urine, feces, ocular fluid, saliva, semen, brain extracts (e.g., brain homogenates), spinal fluid, appendix, spleen and tonsil tissue extracts.

In still another aspect, the present invention is directed to a kit for detecting a nucleic acid, the kit comprising the composition.

In the present invention, the kit may optionally comprise reagents required for performing target nucleic acid amplification reaction (e.g., PCR), such as buffer, DNA polymerase, a DNA polymerase cofactor, and deoxyribonucleotide-5-triphosphate (dNTP). Alternatively, the kit of the present invention may also comprise various oligonucleotide molecules, a reverse transcriptase, various buffers and reagents, and an antibody that inhibits the activity of a DNA polymerase. In addition, the optimal amount of the reagent used in a specific reaction in the kit may be easily determined by those skilled in the art who have implemented the disclosure set forth herein. Typically, the kit of the present invention may be manufactured as a separate package or compartment containing the above-mentioned ingredients.

In one embodiment, the kit may comprise a compartmentalized carrier means containing the sample, a container containing a reagent, a container containing the surrogate target and the primers, and a container containing a probe for detecting the amplicon.

The carrier means is proper to be compartmentalized into one or more containers, such as vials, tubes and the like, each of the container(s) comprising the separate elements to be used in the method of the present invention. In the specification of the present invention, those skilled in the art can easily dispense necessary agents in the container(s).

Hereinafter, the present invention will be described in more detail with reference to examples. It will be obvious to skilled in the art that these examples are merely to illustrate the present invention, and the scope of the present invention is not limited by these examples.

Example 1. Amplification and Detection of Epidermal Growth Factor Receptor (EGFR) Gene 1.1 Preparation of Primers, Surrogate Target, and Probe It is known that the human EGFR gene encodes a membrane protein and a receptor protein that function in the body's signaling system, and cancer can be caused if a mutation of the EGFR gene occurs (Zhang, H. et al., J. Clin. Invest. 2007. 117:2051-2058).

In order to effectively amplify and detect the above-described human EGFR gene by the novel target nucleic acid amplification method of the present invention, target-specific primer 1 and surrogate target 1 capable of hybridizing specifically with the region around codon 790 of exon 20 of the EGFR gene were designed, and amplification primer 1 capable of hybridizing with surrogate target 1 was designed and prepared (Integrated DNA Technologies, Inc., USA). In addition, probe 1 was designed and prepared so that it could detect a fusion amplicon produced and amplified by the designed primers and surrogate target (PANAGENE Inc., South Korea). The nucleotide sequences of each primer, the surrogate target and the probe are shown in Tables 1 and 2.

TABLE 1

Sequences of primers and surrogate target

| Name | SEQ ID NO | Nucleotide sequence (5' end --> 3' end) |
|---|---|---|
| Target-specific primer 1 | SEQ ID NO: 1 | GCCGCCTG CTGGGCATC |
| Amplification primer 1 | SEQ ID NO: 6 | CATCAGGAGC AGTTACGAAG |
| Surrogate target 1 | SEQ ID NO: 9 | TTTTTTCTGGAC TATGTCCGGGAA CACAGGCTTCGT AACTGCTCCTGA TGAAAAAA |

TABLE 2

Sequence of detection probe

| Name | SEQ ID NO | Nucleotide sequence {N terminus --> C terminus) |
|---|---|---|
| Probe 1 | SEQ ID NO 18 | [Dabcyl]-CACAGG CTTC-[O linker]-[K]-[ROX] |

Surrogate target 1 was prepared as a single-stranded oligonucleotide having a length of 56 nucleotides, and an oligonucleotide consisting of six thymine (T) bases and an oligonucleotide of six adenine (A) bases were present at the 5' end and 3' end of surrogate target 1, respectively, in order to prevent the surrogate target from functioning directly as a primer. In the nucleotide sequence of surrogate target 1, the underlined nucleotide sequence is complementary to the target nucleotide sequence of the human EGFR gene, and the italicized nucleotide sequence is complementary to the nucleotide sequence of amplification primer 1.

Probe 1 was prepared as a 10-nucleotide PNA, and the quencher [Dabcyl] and the reporter [ROX] were attached at the N-terminus and C-terminus of the PNA, respectively. The PNA and the [ROX] were linked to each other by [O linker] and [K (lysine)]. When probe 1 hybridizes with a fusion amplicon having a complementary nucleotide sequence, the quencher and the reporter are separated by the longest distance, and at this time, the signal (fluorescence) value from the reporter reaches maximum, and thus the fusion amplicon can be detected by measuring the signal.

Probe 1 has the same nucleotide sequence as a portion of surrogate target 1, through which probe 1 does not hybridize directly with the surrogate target 1, but may hybridize with the nucleic acid polymerization product generated by hybridization of amplification primer 1 with surrogate target 1. However, since the amount of surrogate target 1 added in polymerase chain reaction (PCR) is very small, a detectable signal on an amplification curve is not emitted merely by hybridization of probe 1 to the nucleic acid polymerization product generated by simple hybridization of amplification primer 1 with surrogate target 1. In order for a detectable signal on an amplification curve to be emitted by probe 1, production of the fusion amplicon comprising a portion of the nucleotide sequence of surrogate target 1 should occur, and the amount of a nucleic acid polymerization product with which probe 1 hybridizes should be greatly increased by hybridization of target-specific primer 1 and amplification primer 1 with the fusion amplicon and amplification of the fusion amplicon.

1.2 Production and Identification of Fusion Amplicon

In order to form the intended fusion amplicon under a condition in which about 10,000 copies of the target nucleic acid are present, a polymerase chain reaction (PCR) composition comprising 1.5 pmole of target-specific primer 1, 30 pmole of amplification primer 1, 10 fmole of surrogate target 1 and 2 pmole of probe 1 was prepared. The polymerase chain reaction composition contained a DNA polymerase, which is commonly used in polymerase chain reaction, as well as components such as buffer, deoxynucleotide-5-triphosphate (dNTP), potassium chloride (KCl), magnesium chloride ($MgCl_2$) and a detergent.

Temperature control for the polymerase chain reaction was performed by a thermal cycler, and the polymerase chain reaction was performed under the following conditions: initial denaturation [at 95° C. for 15 min], and then 45 cycles, each consisting of denaturation [at 95° C. for 10 sec]–annealing [at 60° C. for 20 sec]–extension [at 72° C. for 20 sec]. For each cycle, an amplification curve was obtained by measuring the fluorescence value of the ROX channel.

After the polymerase chain reaction, in order to obtain a melting curve of the reaction product, the reaction product was subjected to denaturation [at 95° C. for 5 min]–annealing [at 35° C. for 5 min]–melting [35° C.→75° C. at 0.5° C. interval], and the fluorescence value measured in the melting step was analyzed to obtain the melting peak results.

As a result, under a condition in which about 10,000 copies of the target nucleic acid were present, a rise in the fluorescence signal on the amplification curve was observed, and under a condition in which the target nucleic acid was not present, no rise in the fluorescence signal appeared. Thus, the two conditions were clearly distinguishable from each other. In addition, under the condition in which the target nucleic acid was present, a very high melting peak appeared at around 56° C., whereas, under the condition in which the target nucleic acid was not present, a melting peak was observed at around 56° C., but the height thereof was significantly low. Thus, the two conditions could also be distinguished through the difference in the height of the melting peak on the melting curve (FIG. 9A and FIG. 9B).

Example 2. Amplification and Detection of Epidermal Growth Factor Receptor Using Composition Comprising Assistant Primer 2.1 Synthesis of Assistant Primer In order to detect the above-described human EGFR gene with high sensitivity using the target nucleic acid amplification method of the present invention, target-specific primer 1, surrogate target 1, amplification primer 1, probe 1, and assistant primer 1 capable of hybridizing specifically with the EGFR gene were designed and prepared (Integrated DNA Technologies, Inc., USA). The nucleotide sequences of each primer, the surrogate target and the probe are shown in Tables 3 and 4.

TABLE 3

Sequences of primers and surrogate target

| Name | SEQ ID NO | Nucleotide sequence (5' end --> 3' end) |
|---|---|---|
| Target-specific primer 1 | SEQ ID NO: 1 | GCCGCCTGCTGGGCATC |
| Amplification primer 1 | SEQ ID NO: 6 | CATCAGGAGCAGTTACGAAG |
| Surrogate target 1 | SEQ ID NO: 9 | TTTTTTCTGGACTATGTCCGG GAACACAGGCTTCGTAACTGC TCCTGATGAAAAAA |
| Assistant primer 1 | SEQ ID NO: 18 | GCTATCCCAGGAGCGCAGACC |

TABLE 4

Sequence of detection probe

| Name | SEQ ID NO | Nucleotide sequence (N terminus --> C terminus) |
|---|---|---|
| Probe 1 | SEQ ID NO: 20 | [Dabcyl]-CACAGGCTTC- [O linker]-[K]-[ROX] |

2.2 Production and Identification of Fusion Amplicon Comprising Assistant Primer In order to form the intended fusion amplicon under a condition in which about 10 to 10,000 copies of the target nucleic acid are present, a polymerase chain reaction (PCR) composition comprising 1.5 pmole of target-specific primer 1, 30 pmole of amplification primer 1, 0.5 pmole of assistant primer 1, 10 fmole of surrogate target 1, and 2 pmole of probe 1 was prepared. The polymerase chain reaction composition contained a DNA polymerase, which is commonly used in polymerase chain reaction, as well as components such as buffer, deoxynucleotide-5-triphosphate (dNTP), potassium chloride (KCl), magnesium chloride ($MgCl_2$) and a detergent.

Temperature control for the polymerase chain reaction was performed using a general thermal cycler, and the polymerase chain reaction was performed under the following conditions: initial denaturation [at 95° C. for 15 min], and then 15 cycles, each consisting of denaturation [at 95° C. for 10 sec]–annealing [at 64° C. for 20 sec]–extension [at 72° C. for 20 sec], which is a first cycling step, followed by 30 cycles, each consisting of denaturation [at 95° C. for 10 sec]–annealing [at 60° C. for 20 sec]–extension [at 72° C. for 20 sec], which is a second cycling step. For each cycle in the second cycling step, an amplification curve was obtained by measuring the fluorescence value of the ROX channel.

After the polymerase chain reaction, in order to obtain a melting curve of the reaction product, the reaction product was subjected to denaturation [at 95° C. for 5 min]-annealing [at 35° C. for 5 min]-melting [35° C.→75° C. at 0.5° C. interval], and the fluorescence value measured in the melting step was analyzed to obtain the melting peak results.

As a result, under all the condition in which about 10 to 10,000 copies of the target nucleic acid were present, a rise in the fluorescence signal on the amplification curve was observed, and under a condition in which the target nucleic acid was not present, no rise in the fluorescence signal appeared. Thus, the two conditions were clearly distinguishable from each other. In addition, under the condition in which the target nucleic acid was present, a very high melting peak appeared at around 56° C., whereas, under the condition in which the target nucleic acid was not present, the height thereof was significantly low even though a melting peak was observed at around 56° C. Thus, the two conditions could also be distinguished through the difference in the height of the melting peak on the melting curve (FIG. 10A-FIG. 10E).

Example 3. Amplification and Detection of Epidermal Growth Factor Receptor Using Various Types of Surrogate Targets 3.1 Preparation of Primers, Surrogate Targets, and Probe In order to amplify and detect the above-described human EGFR gene using various types of surrogate targets, target-specific primer 2, surrogate target 1, surrogate target 2, surrogate target 3 and assistant primer 1, which are capable of hybridizing specifically with the region around codon 790 of exon 20 of the EGFR gene, were designed, and amplification primer 1, which is capable of hybridizing with surrogate target 1 or 2 and has the same nucleotide sequence as a portion of the nucleotide sequence of surrogate target 3, was designed and prepared (Integrated DNA Technologies, Inc., USA). In addition, probe 2 was designed and prepared so that it could detect a fusion amplicon produced and amplified by the designed primers and surrogate target (PANAGENE Inc., South Korea). The nucleotide sequences of each primer, each surrogate target and the probe are shown in Tables 5 and 6.

TABLE 5

Sequences of primers and surrogate targets

| Name | SEQ ID NO | Nucleotide sequence (5' end --> 3' end) |
|---|---|---|
| Target-specific primer 2 | SEQ ID NO: 2 | ACCTCCACCGTGCAGCTCA |
| Amplification primer 1 | SEQ ID NO: 6 | CATCAGGAGCAGTTACGAAG |
| Surrogate target 1 | SEQ ID NO: 9 | TTTTTTCTGGACTATGTCCG GGAACACAGGCTTCGTAACT GCTCCTGATGAAAAAA |
| Surrogate target 2 | SEQ ID NO: 10 | CTGGACTATGTCCGGGAACAC AGGCTTCGTAACTGCTCCTGA TGAAAAAA |
| Surrogate target 3 | SEQ ID NO: 11 | CATCAGGAGCAGTTACGAAGCC TGTGTTCCCGGACATAGTCCAG |
| Assistant primer 1 | SEQ ID NO: 18 | GCTATCCCAGGAGCGCAGACC |

TABLE 6

Sequence of detection probe

| Name | SEQ ID NO | Nucleotide sequence (N terminus --> C terminus) |
|---|---|---|
| Probe 2 | SEQ ID NO: 21 | [Dabcyl]-CTCATCA TGCAG-[K]-[FAM] |

Surrogate target 2 was prepared as a single-stranded oligonucleotide having a length of 50 nucleotides, and a sequence consisting of six adenine (A) bases was present at the 3' end of surrogate target 2 in order to prevent the surrogate target from functioning directly as a primer. In the nucleotide sequence of surrogate target 2, the underlined nucleotide sequence is complementary to the target nucleotide sequence of the human EGFR gene, and the italicized nucleotide sequence is complementary to the nucleotide sequence of amplification primer 1.

Surrogate target 3 was prepared as a single-stranded oligonucleotide having a length of 44 nucleotides. The underlined nucleotide sequence of surrogate target 3 is complementary to the target nucleotide sequence of the human EGFR gene, and the italicized nucleotide sequence is identical to the nucleotide sequence of amplification primer 1.

Probe 2 was prepared as a 12-nucleoide PNA, and the quencher [Dabcyl] and the reporter [FAM] were attached at the N-terminus and C-terminus of the PNA, respectively. The PNA and the [FAM] were linked by [K]. When probe 2 hybridizes with a fusion amplicon having a complementary nucleotide sequence, the quencher and the reporter are separated by the longest distance, and at this time, the signal (fluorescence) value from the reporter reaches maximum, and thus the fusion amplicon can be detected by measuring the signal.

3.2 Production and Identification of Fusion Amplicon

In order to form the intended fusion amplicon under a condition in which about 100 copies of the target nucleic acid are present, a polymerase chain reaction (PCR) composition comprising 1.5 pmole of target-specific primer 2, 30 pmole of amplification primer 1 and 4 pmole of probe 2 was prepared. Additionally, 10 fmole of one selected from among surrogate target 1, surrogate target 2 and surrogate target 3 was added, or 10 fmole of surrogate target 2 and 10 fmole of surrogate target 3 were added together. The polymerase chain reaction composition contained a DNA polymerase, which is commonly used in polymerase chain reactions, as well as components such as buffer, deoxynucleotide-5-triphosphate (dNTP), potassium chloride (KCl), magnesium chloride ($MgCl_2$) and a detergent.

Figure 1:
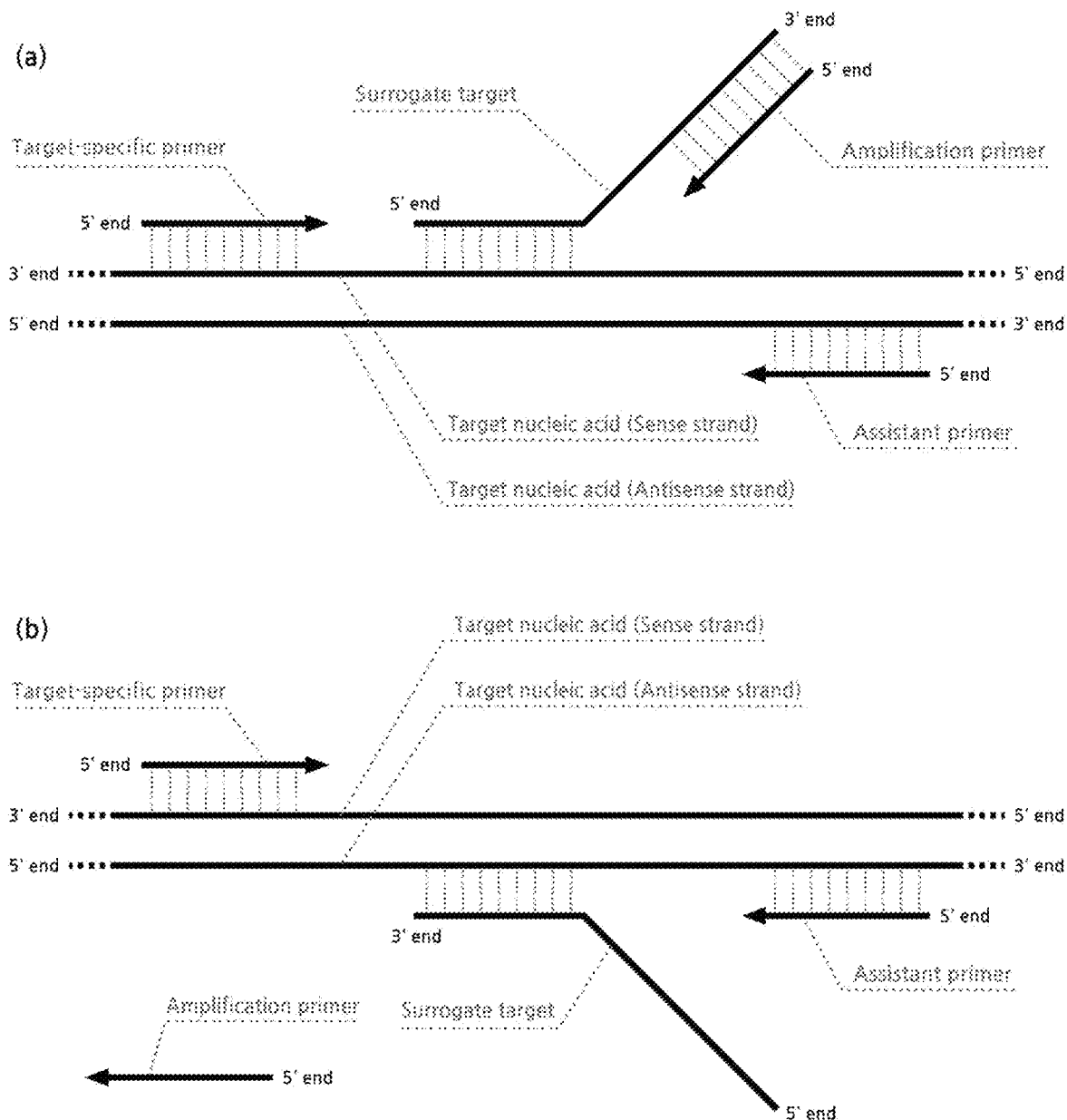
FIG. 1 shows elements necessary for implementation of the present invention and the hybridizing relationship between the elements. Specifically.
Figure 2:
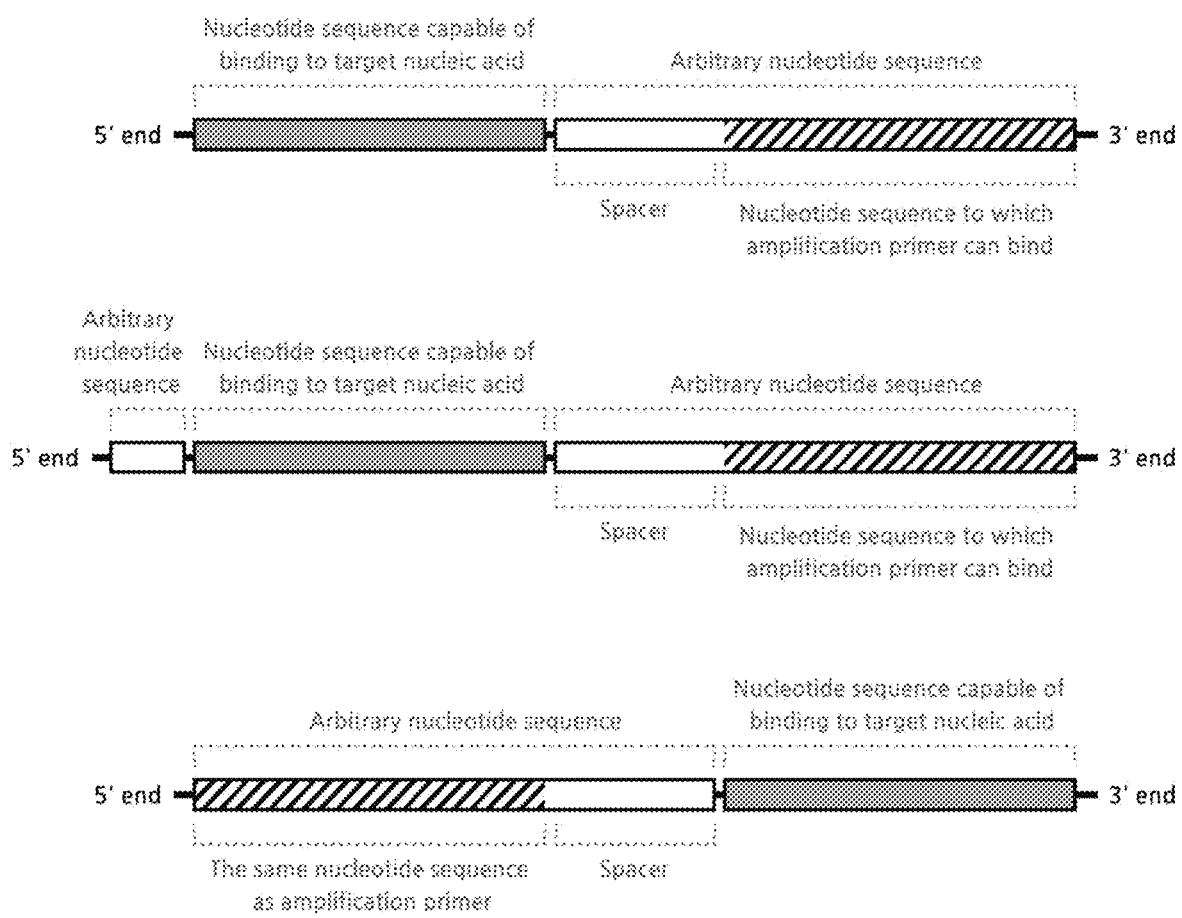
FIG. 2 shows the structures of surrogate targets that may be used in implementations of the present invention.
Figure 3:
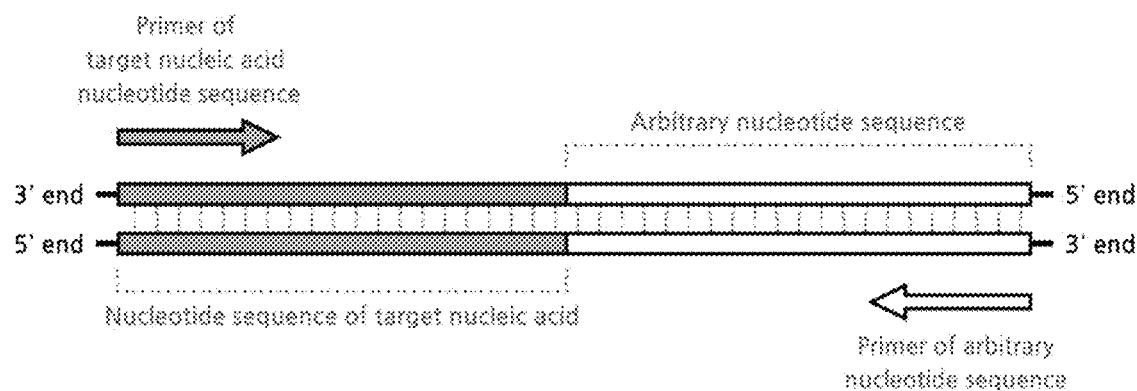
FIG. 3 shows a comparison between a fusion amplicon obtained in an embodiment of the present invention (FIG. 3(a)) and an amplicon obtained in a conventional polymerase chain reaction (FIG. 3(b)).
Figure 3:
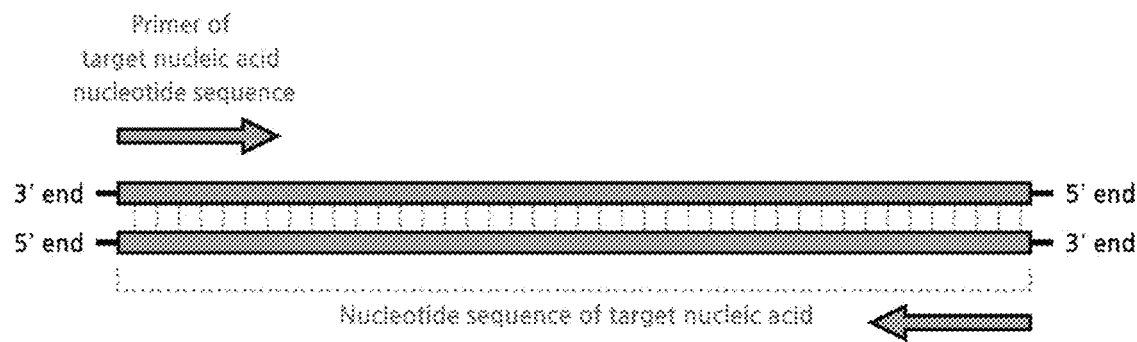
Figure 4:
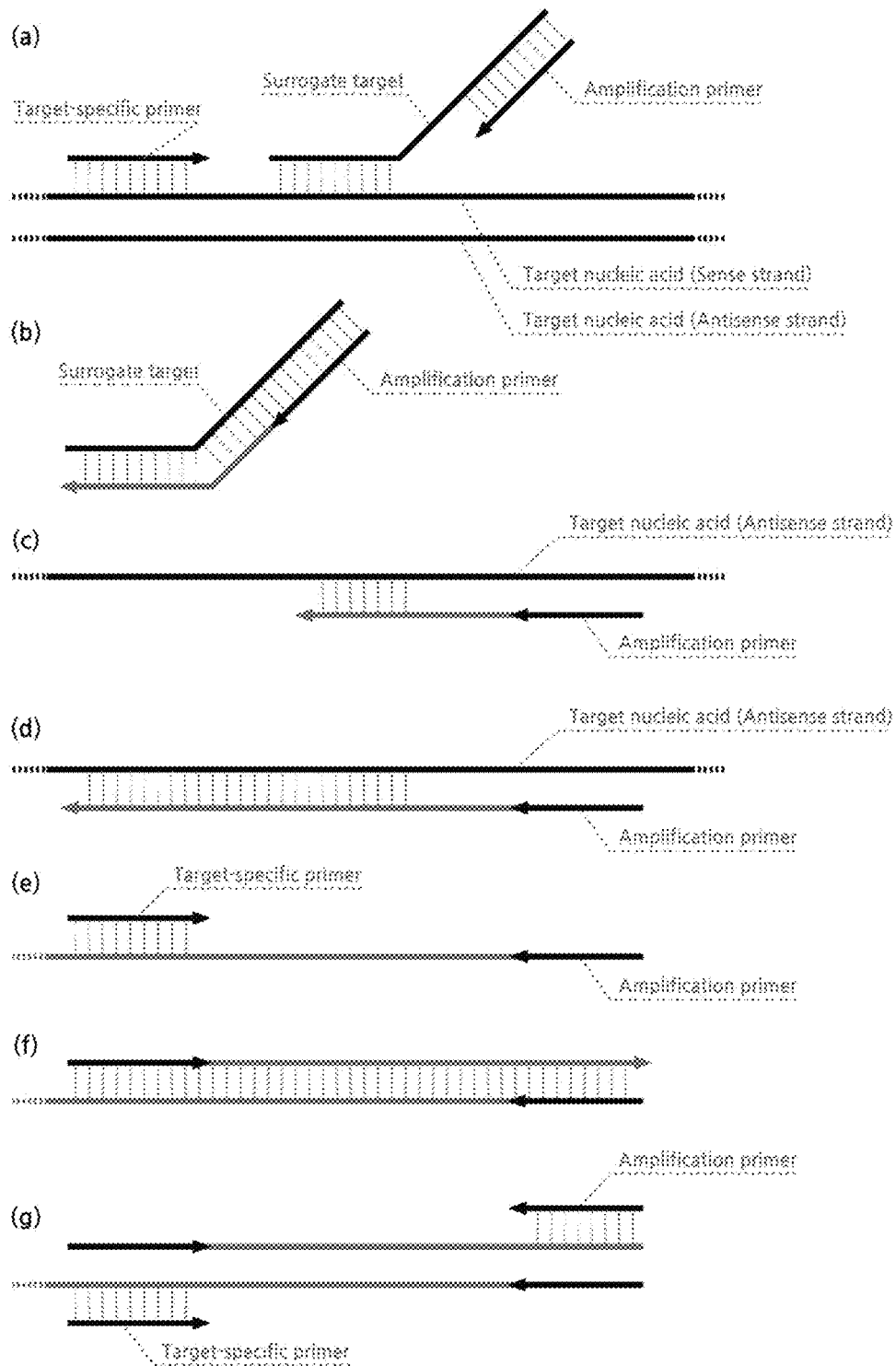
FIG. 4 shows one of possible mechanisms for forming a fusion amplicon in an embodiment of the present invention. Specifically.
Figure 5:
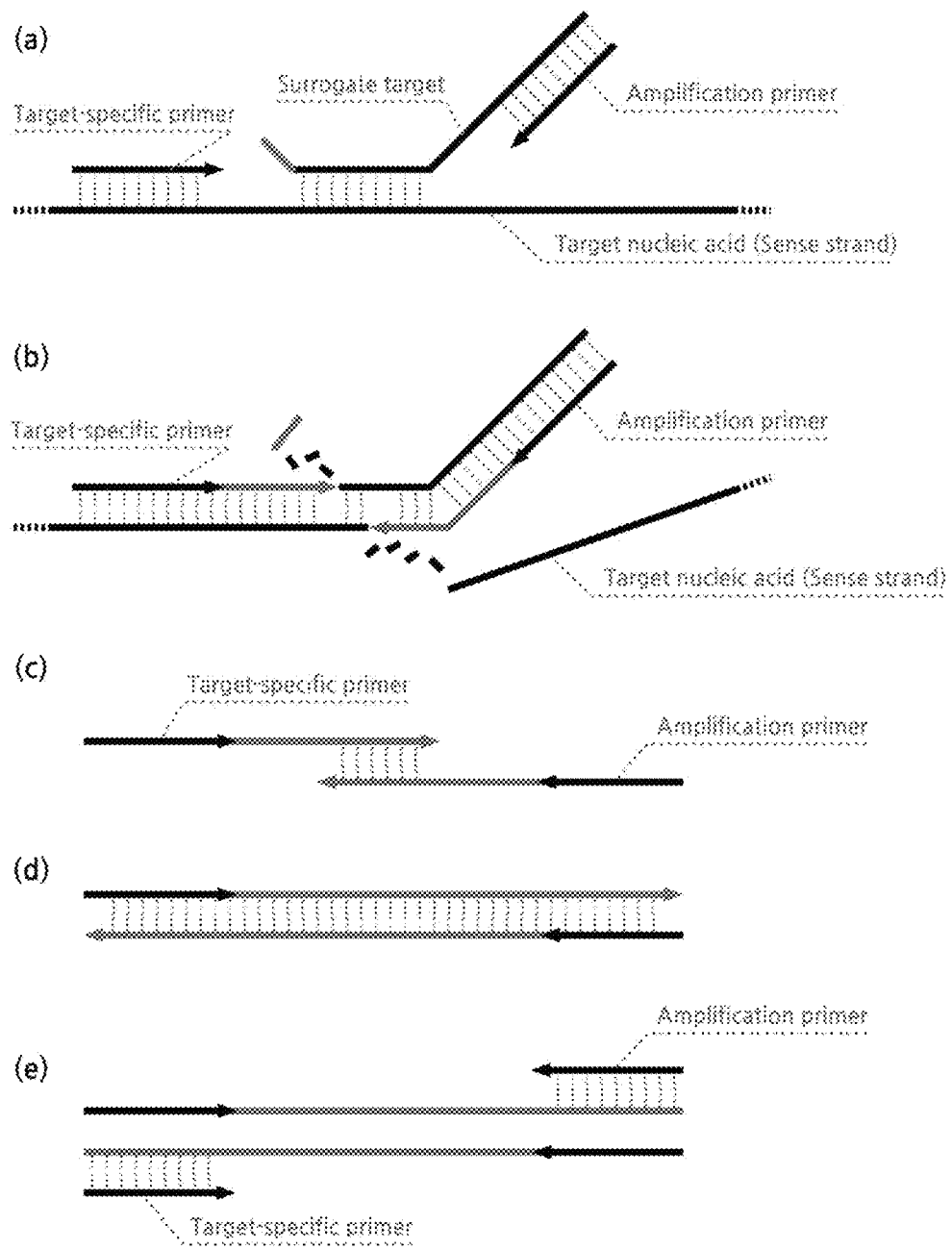
FIG. 5 shows one of possible mechanisms for forming a fusion amplicon in an embodiment of the present invention. Specifically.
Figure 6:
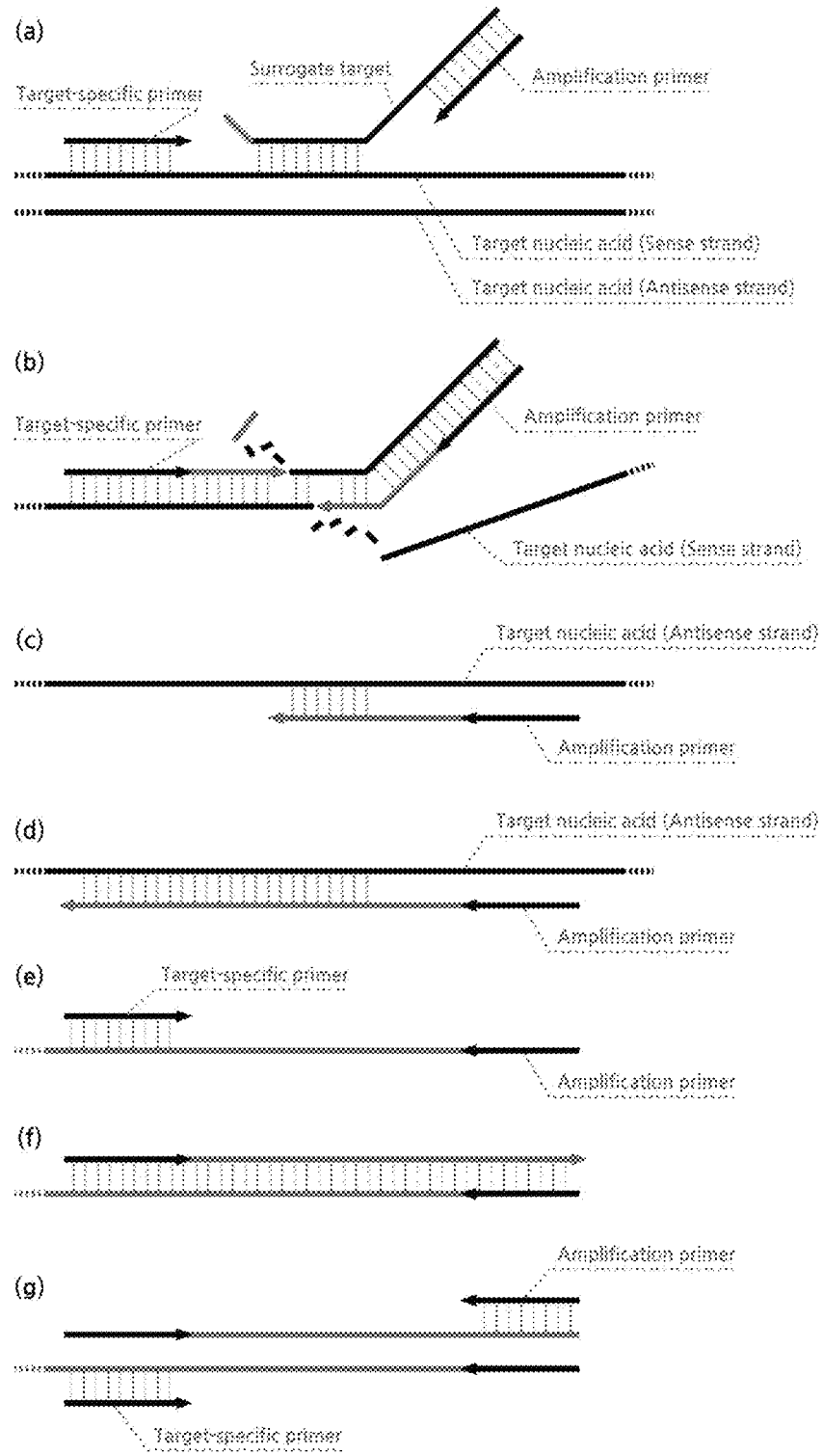
FIG. 6 shows one of possible mechanisms for forming a fusion amplicon in an embodiment of the present invention. Specifically.
Figure 7:
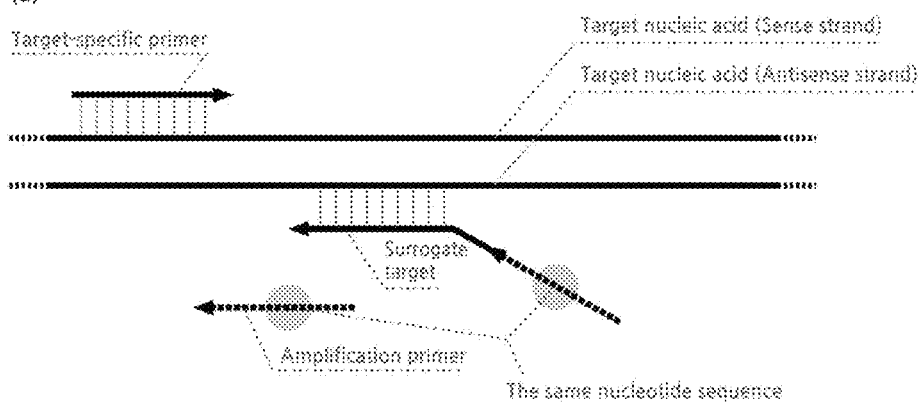
FIG. 7 shows one of possible mechanisms for forming a fusion amplicon in an embodiment of the present invention. Specifically.
Figure 7:
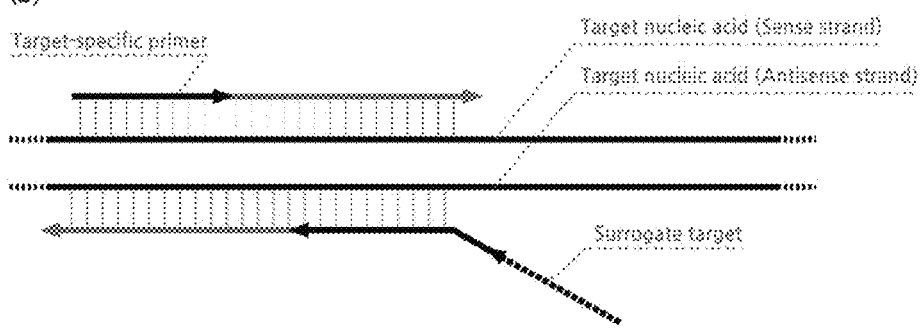
Figure 7:
Figure 7:
Figure 7:
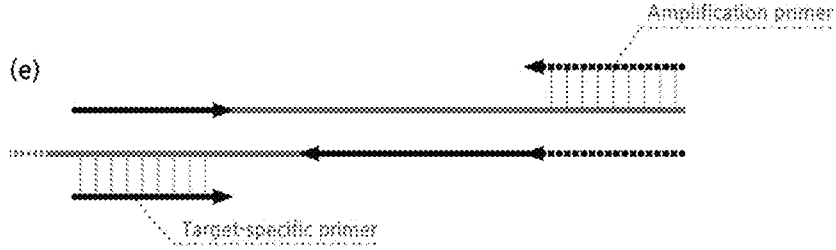
Figure 8:
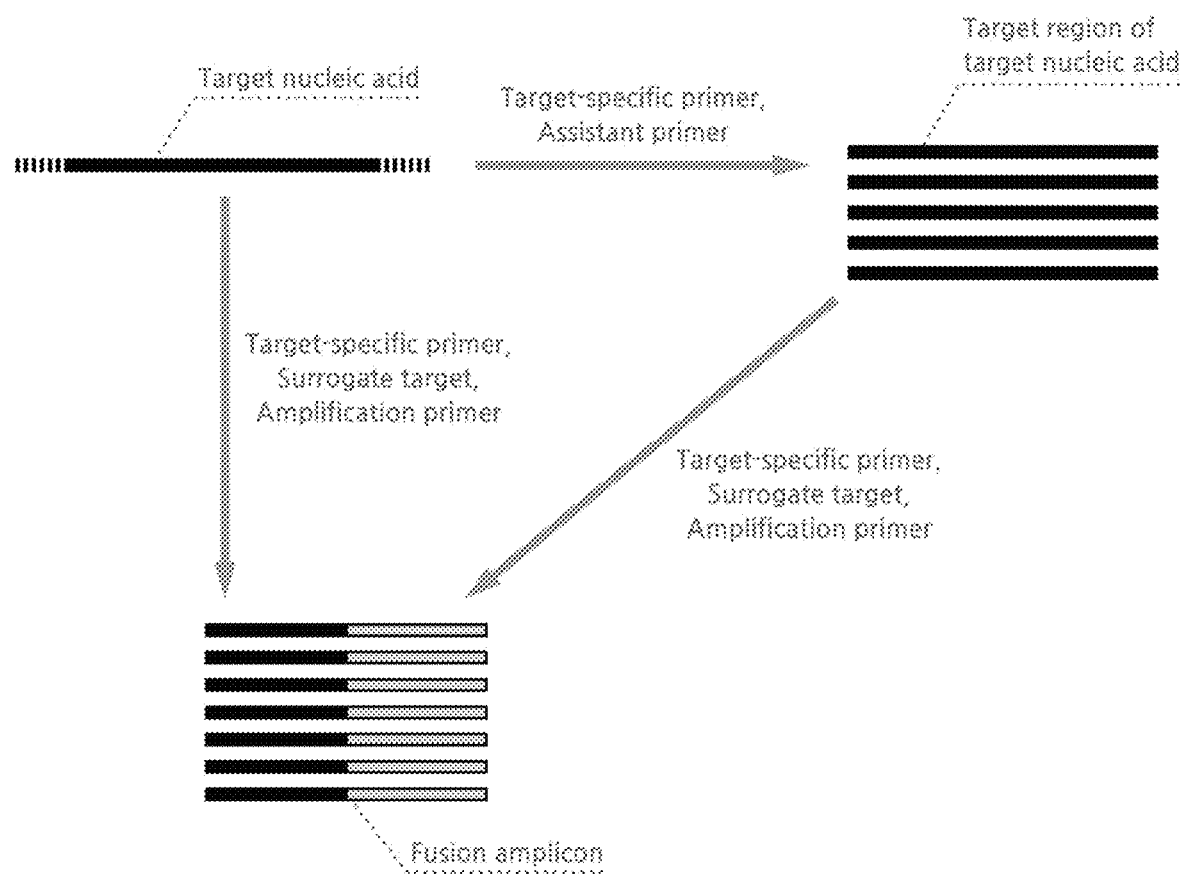
FIG. 8 shows the role of an assistant primer that may be used in implementations of the present invention. The assistant primer may be paired with the target-specific primer to increase the amount of the target region of the target nucleic acid, thereby promoting fusion amplicon production under a condition in which a trace amount of the target nucleic acid is present.

In the case of surrogate target 1, a fusion amplicon may be formed by processes including the mechanisms shown in FIGS. 5 and 6, and in the case of surrogate target 2, a fusion amplicon may be formed by processes including the mechanism shown in FIG. 4, and in the case of surrogate target 3, a fusion amplicon may be produced by processes including the mechanism shown in FIG. 7.

Temperature control for the polymerase chain reaction may be performed by a general thermal cycler, and the polymerase chain reaction was performed under the following conditions: initial denaturation [at 95° C. for 15 min], and then 15 cycles, each consisting of denaturation [at 95° C. for 10 sec]–annealing [at 64° C. for 30 sec]–extension [at 72° C. for 20 sec], which is a first cycling step, followed by 35 cycles, each consisting of denaturation [at 95° C. for 10 sec]–annealing [at 60° C. for 20 sec]–extension [at 72° C. for 20 sec], which is a second cycling step. For each cycle in the second cycling step, an amplification curve was obtained by measuring the fluorescence value of the FAM channel.

After the polymerase chain reaction, in order to obtain a melting curve of the reaction product, the reaction product was subjected to denaturation [at 95° C. for 5 min]–annealing [at 35° C. for 5 min]–melting [35° C.→75° C. with 0.5° C. interval], and the fluorescence value measured in the melting step was analyzed to obtain the melting peak results.

As a result, under all the amplification condition in which about 100 copies of the target nucleic acid were present, a rise in the fluorescence signal on the amplification curve was observed, and under a condition in which the target nucleic acid was not present, no rise in the fluorescence signal appeared. Thus, the two conditions were clearly distinguishable from each other. In addition, under the condition in which the target nucleic acid was present, a very high melting peak appeared at around 52° C., whereas, under the condition in which the target nucleic acid was not present, no melting peak was observed at around 52° C. Thus, the two conditions could also be distinguished through this difference (FIG. 11A-FIG. 11H).

Example 4. Amplification of High GC-Content Region in Human HRAS Gene 4.1 Preparation of Primers, Surrogate Target, and Probe It is known that the human HRAS gene encodes a protein which is involved in the intracellular signaling system, and a mutation in a region corresponding to codons 12, 13 and 61 of the HRAS gene is associated with the development of various cancers (Rajasekharan, S. K. and Raman, T. *Cent. Eur. J. Biol.* 2013. 8:609-624).

The region corresponding to codons 12 and 13 of exon 2 of the above-described human HRAS gene has a high average G/C content approaching 70%, and hence may be difficult to amplify with high efficiency by a conventional polymerase chain reaction (PCR) method. Thus, in order to effectively amplify and detect this region by the novel target nucleic acid amplification method of the present invention, target-specific primer 3, surrogate target 4 and assistant primer 2, which are capable of hybridizing specifically to the HRAS gene, were designed, and amplification primer 2 capable of hybridizing with surrogate target 4 was designed and prepared (Integrated DNA Technologies, Inc., USA). In addition, probe 3 was designed and prepared so that it could detect a fusion amplicon produced and amplified by the designed primers and surrogate target (PANAGENE Inc., South Korea). The nucleotide sequences of each primer, the surrogate target and the probe are shown in Tables 7 and 8.

TABLE 7

Sequences of primers and surrogate target

| Name | SEQ ID NO | Nucleotide sequence (5' end --> 3' end) |
|---|---|---|
| Target-specific primer 3 | SEQ ID NO: 3 | AGCGCACTCTTGCCCAC |
| Amplification primer 2 | SEQ ID NO: 7 | AACCTTAGCACGAATAGCG |
| Surrogate target 4 | SEQ ID NO: 12 | TTTTTT<u>ATATTCCGTCATCG CTCCTCAGGA</u>*CCGCTATTCG TGCTAAGGTT*AAAAAA |
| Assistant primer 2 | SEQ ID NO: 19 | TGTGGGTTTGCCCTTCAGATGG |

TABLE 8

Sequence of detection probe

| Name | SEQ ID NO | Nucleotide sequence (N terminus --> C terminus) |
|---|---|---|
| Probe 3 | SEQ ID NO: 22 | [Dabcyl]-[K]-[Dabcyl]-CAC^CG^CTGG-[O linker]-[K]-[ROX] |

Surrogate target 4 was prepared as a single-stranded oligonucleotide having a length of 56 nucleotides, and an oligonucleotide consisting of six thymine (T) bases and an oligonucleotide of six adenine (A) bases were present at the 5' end and 3' end of surrogate target 4, respectively, in order to prevent the surrogate target from functioning directly as a primer. In the nucleotide sequence of surrogate target 4, the underlined nucleotide sequence is complementary to the target nucleotide sequence of the human HRAS gene, and the italicized nucleotide sequence is complementary to the nucleotide sequence of amplification primer 2.

Probe 3 was prepared as a 9-nucleoide PNA, and two quenchers [Dabcyl] linked to each other by [K (lysine)] were attached at the N-terminus of the PNA, and the reporter [ROX] was attached at the C-terminus of the PNA. The PNA and the [ROX] were linked to each other by [O linker] and [K (lysine)]. In addition, at the portions indicated by [^] in the nucleotide sequence of probe 3, a positively charged functional group (glutamate) was connected to the PNA backbone, thereby introducing the charge into the PNA backbone that was not originally charged. When probe 3 hybridizes with the fusion amplicon having a complementary nucleotide sequence, the quencher and the reporter are separated by the longest distance, and at this time, the signal (fluorescence) value from the reporter reaches maximum, and thus the fusion amplicon can be detected by measuring the signal.

The nucleotide sequence of probe 3 is characterized in that it is not complementary to any of target-specific primer 3, amplification primer 2, surrogate target 4 and assistant primer 2, but is complementary to a target nucleic acid amplicon caused by assistant primer 2 and an amplicon strand caused by amplification primer 2 in the fusion amplicon comprising a portion of the nucleotide sequence of surrogate target 4. However, since the amount of assistant primer 2 added is very small and target-specific primer 3, which is paired with the assistant primer, is added in a relatively large amount, a detectable signal cannot be emitted merely by hybridization of probe 3 with the target nucleic acid amplicon strand caused by assistant primer 2. On the other hand, amplification primer 2, which amplifies the fusion amplicon, is added in a very large amount and target-specific primer 3, which is paired, is added in a relatively small amount, and hence when probe 3 hybridizes with the amplicon strand caused by amplification primer 2 in the fusion amplicon, a signal can be effectively emitted, whereby only the fusion amplicon can be selectively detected.

4.2 Production and Identification of Fusion Amplicon

In order to form the intended fusion amplicon under a condition in which about 25 ng of extracted human genomic DNA is present, a polymerase chain reaction composition comprising 1.5 pmole of target-specific primer 3, 30 pmole of amplification primer 2, 0.5 pmole of assistant primer 2, 10 fmole of surrogate target 4 and 4 pmole of probe 3 was prepared. The polymerase chain reaction composition contained a DNA polymerase, which is commonly used in polymerase chain reaction, as well as components such as buffer, deoxynucleotide-5-triphosphate (dNTP), potassium chloride (KCl), magnesium chloride ($MgCl_2$) and a detergent.

Temperature control for the polymerase chain reaction was performed using a general thermal cycler, and the polymerase chain reaction was performed under the following conditions: initial denaturation [at 95° C. for 15 min], and then 15 cycles, each consisting of denaturation [at 95° C. for 10 sec]–annealing [at 64° C. for 20 sec]–extension [at 72° C. for 20 sec], which is a first cycling step, followed by 35 cycles, each consisting of denaturation [at 95° C. for 10 sec]–annealing [at 60° C. for 20 sec]–extension [at 72° C. for 20], which is a second cycling step. For each cycle in the second cycling step, an amplification curve was obtained by measuring the fluorescence value of the ROX channel.

In addition, for comparison with the performance of the target nucleic acid amplification method of the present invention for detection of the region corresponding to codons 12 and 13 of exon 2 of the HRAS gene, detection of the same region using a conventional polymerase chain reaction as a control was also performed, and a composition for control polymerase chain reaction was prepared by excluding surrogate target 4 and amplification primer 2 from the polymerase chain reaction composition and increasing the amount of assistant primer 2 added to 30 pmole.

Temperature control for the control polymerase chain reaction was performed using a general thermal cycler, and the control polymerase chain reaction was performed under the following conditions: initial denaturation [at 95° C. for 15 min], and then 50 cycles, each consisting of denaturation [at 95° C. for 10 sec]–annealing [at 60° C. for 20 sec]–extension [at 72° C. for 20 sec]. For each cycle, an amplification curve was obtained by measuring the fluorescence value of the ROX channel.

Figure 12A:
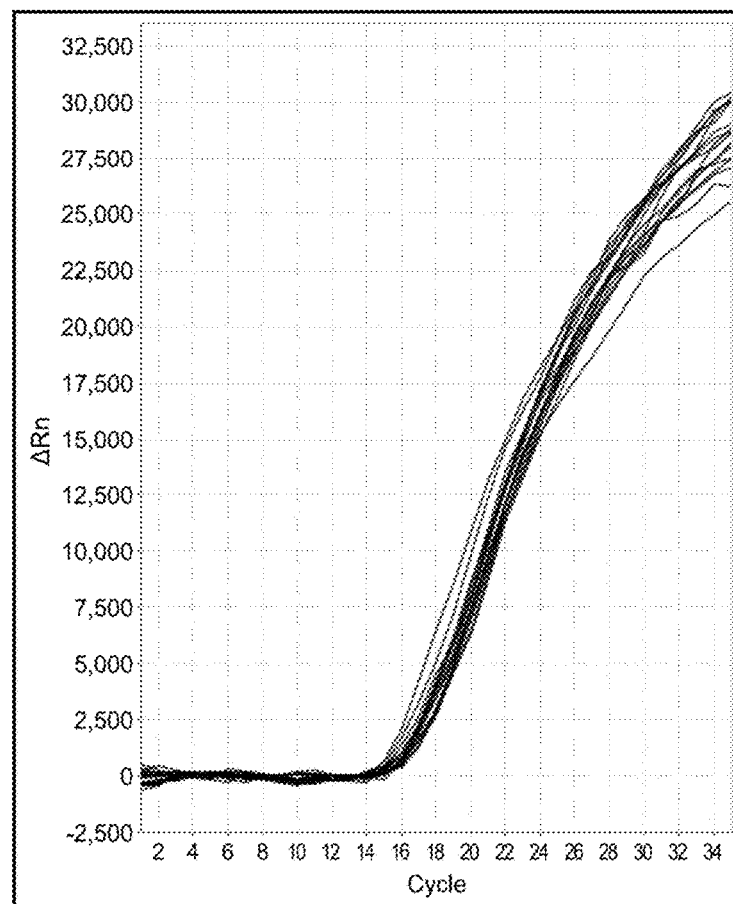
FIG. 12A and FIG. 12B show the results of amplifying the HRAS gene having a relatively high guanine/cytosine content in the human genome in an Example of the present invention, and compares a target nucleic acid amplification method of the present invention (FIG. 12A) with a conventional target nucleic acid amplification method (FIG. 12B).
Figure 12B:
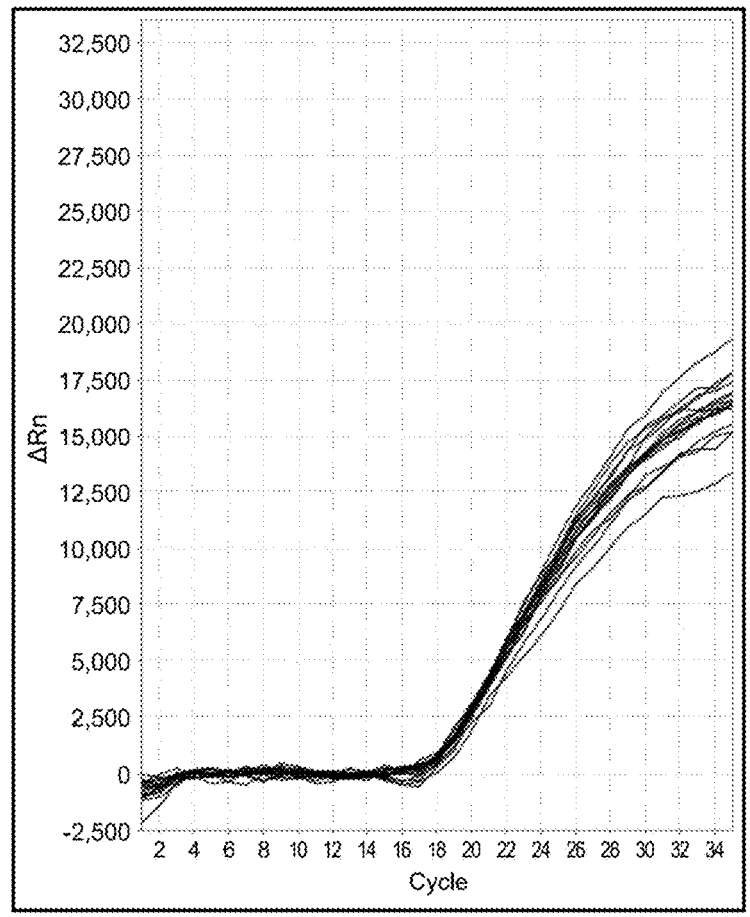
Figure 13A:
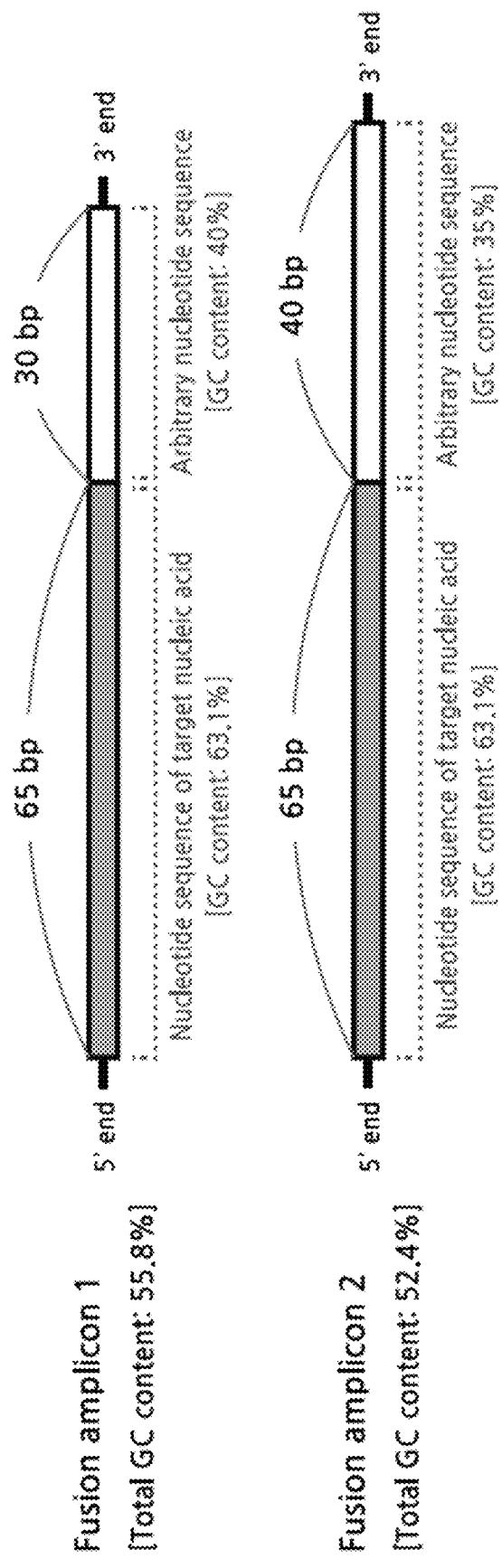
FIG. 13A-FIG. 13F show the results of amplifying and detecting the HRAS gene having a relatively high guanine/cytosine content in the human genome in an Example of the present invention, and compares a target nucleic acid amplification method of the present invention (FIG. 13A and FIG. 13B) with a conventional target nucleic acid amplification method (FIG. 13C-FIG. 13F).
Figure 13B:
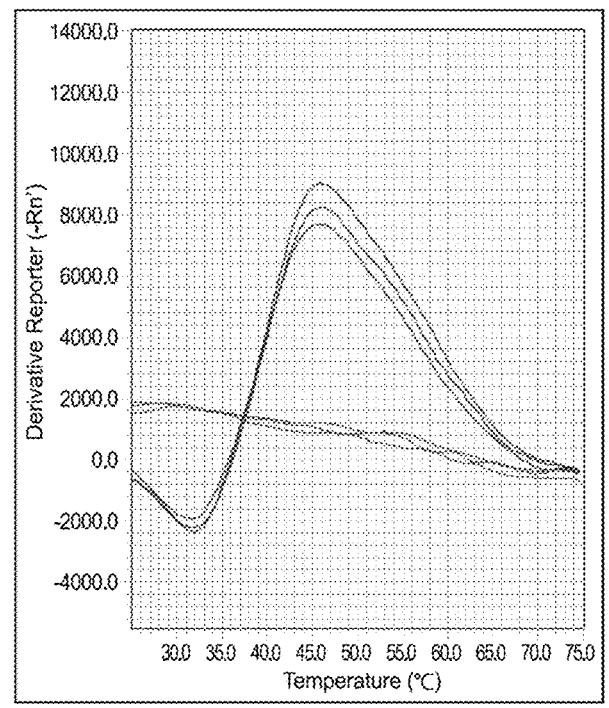
Figure 13B:
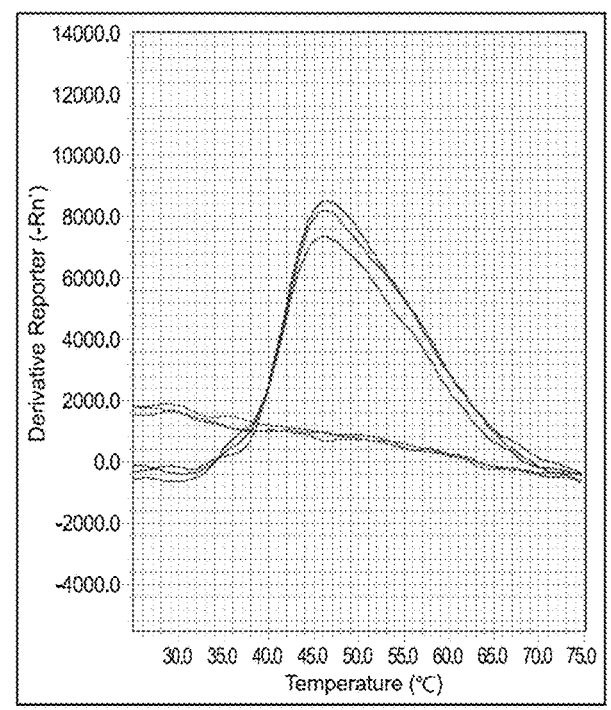
Figure 13C:
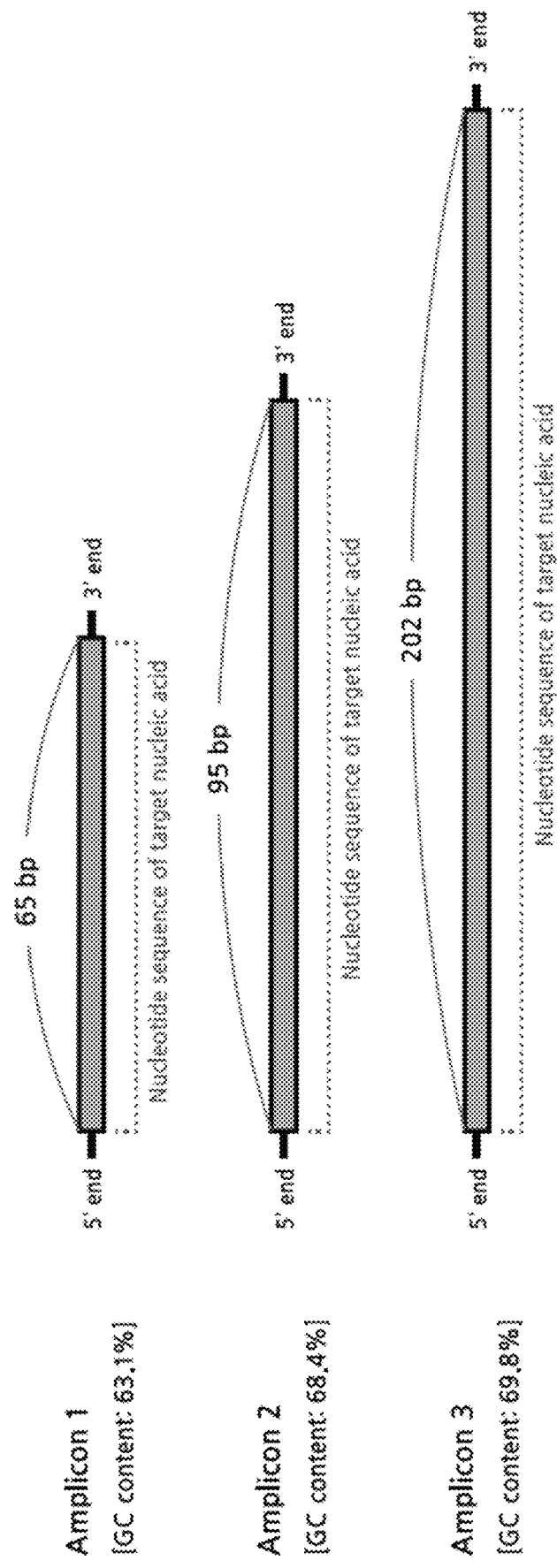
Figure 13D:
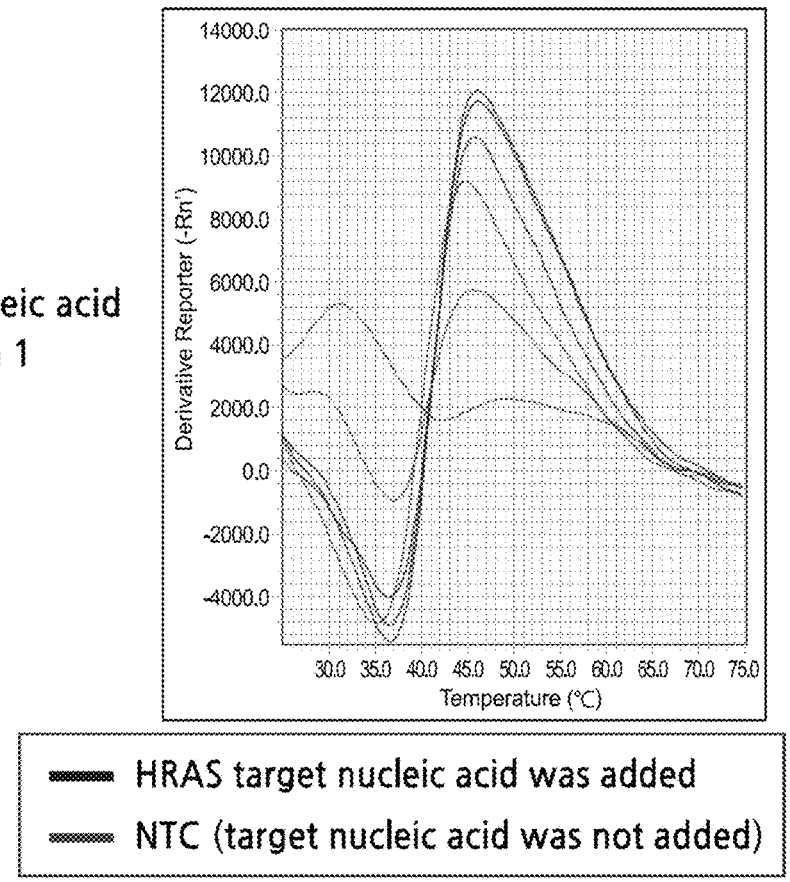
Figure 13E:
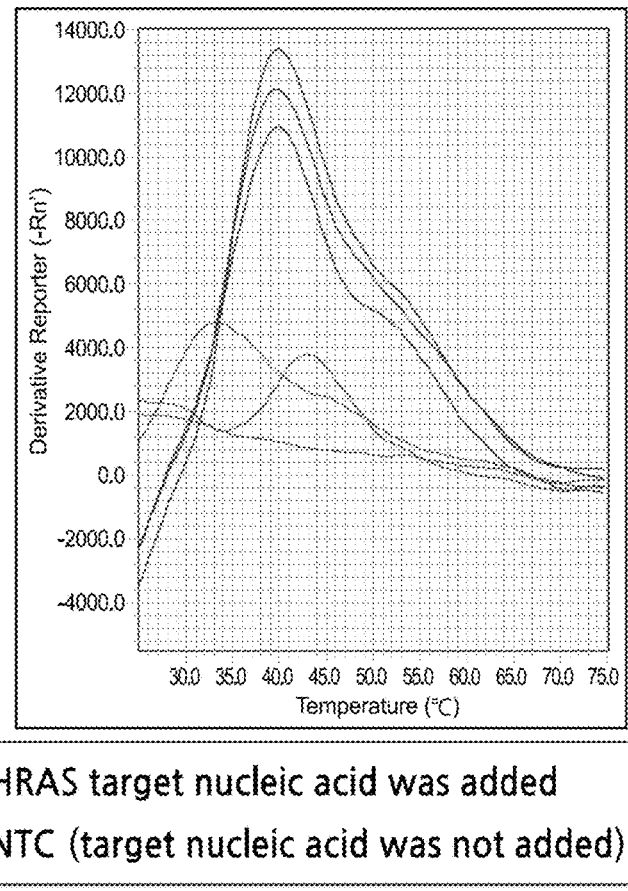
Figure 13F:
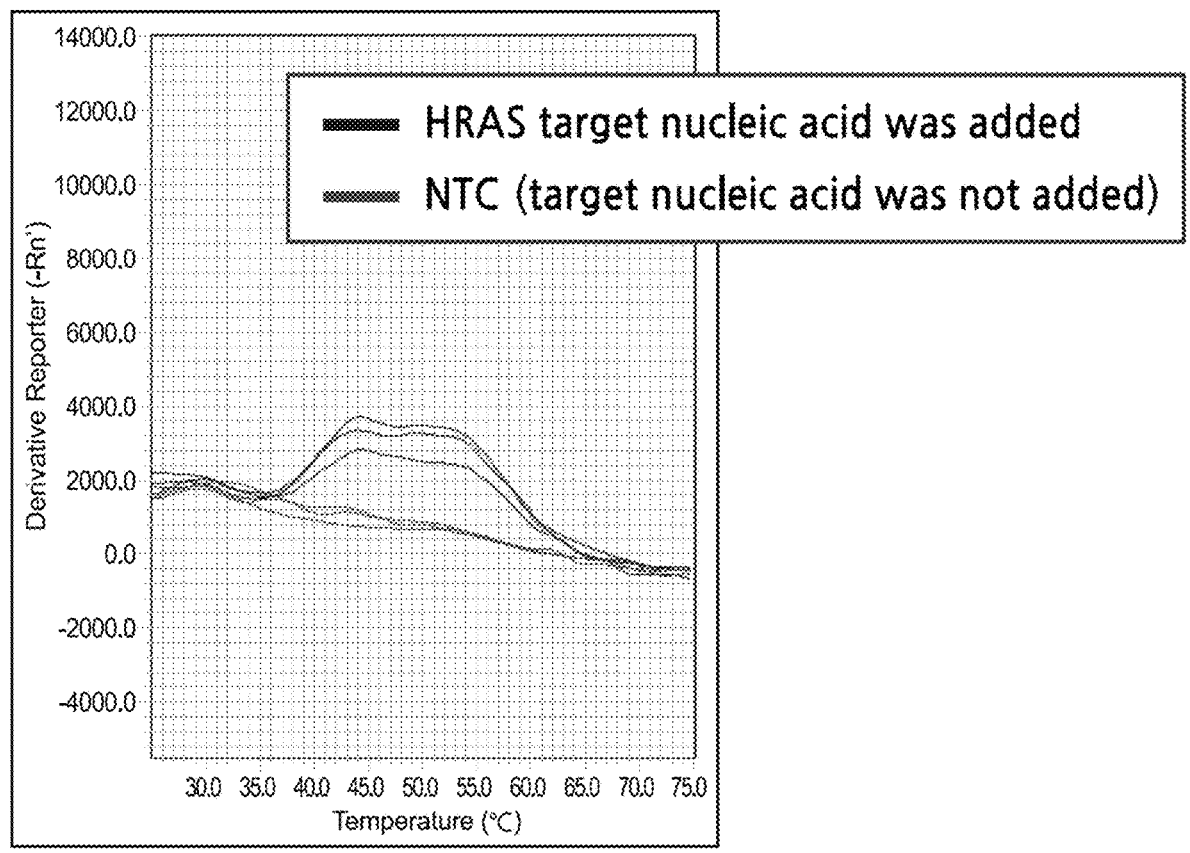

As a result, it was confirmed that, under the condition in which about 25 ng of the extracted human genomic DNA was present, the amplification efficiency of the region corresponding to codons 12 and 13 of exon 2 of HRAS, which has a high G/C content, was significantly higher when the target nucleic acid amplification method of the present invention was used. That is, it was shown that the method of detecting the target nucleic acid by forming the fusion amplicon using the composition comprising surrogate target 4 and amplification primer 2 showed a steep increase in amplification curve slope of 1.5-fold in detection of the nucleic acid having a high G/C content and also showed a higher amplification curve height, compared to the conventional method of detecting the target nucleic acid by direct amplification (FIG. 12A and FIG. 12B). The slope of the amplification curve was calculated through the difference between two Ct values caused by two different fluorescence thresholds, and the results are shown in Table 9 below.

TABLE 9

Comparison of amplification curve slope between the target nucleic acid amplification method of the present invention and the conventional method

| Methods | Mean Ct value 1 (threshold 1: 2,500) | Mean Ct value 2 (threshold 2: 7,500) | Slope ((threshold 2 - threshold 1) / (mean Ct value 2 - mean Ct value 1)) |
|---|---|---|---|
| Target nucleic acid amplification method of the present invention | 17.12 | 19.69 | 1,950.0 |
| Conventional target nucleic acid amplification method | 19.82 | 23.61 | 1,321.0 |

Example 5. Amplification and Detection of High-GC-Content Region in Human HRAS Gene 5.1 Preparation of Primers, Surrogate Targets, and Probe In order to effectively amplify and detect the region corresponding to codons 12 and 13 of exon 2 of the human HRAS gene, which is difficult to amplify and detect by a conventional polymerase chain reaction (PCR) method due to the high-G/C-content thereof, through the novel target nucleic acid amplification method of the present invention, target-specific primer 3, surrogate target 5, surrogate target 6 and assistant primer 2, which are capable of hybridizing specifically with the HRAS gene, were designed, and amplification primer 1 capable of hybridizing with surrogate target 5 and surrogate target 6 was designed and prepared (Integrated DNA Technologies, Inc., USA). In addition, probe 3 was designed and prepared such that it could detect a fusion amplicon produced and amplified by the designed primers and surrogate targets (PANAGENE Inc., South Korea). The nucleotide sequences of each primer, each surrogate target and the probe are shown in Tables 10 and 11 below.

TABLE 10

Sequences of primers and surrogate targets

| Name | SEQ ID NO | Nucleotide sequence (5' end --> 3' end) |
|---|---|---|
| Target-specific primer 3 | SEQ ID NO: 3 | AGCGCACTCTTGCCCAC |
| Amplification primer 1 | SEQ ID NO: 6 | CATCAGGAGCAGTTACGAAG |

TABLE 10-continued

Sequences of primers and surrogate targets

| Name | SEQ ID NO | Nucleotide sequence (5' end --> 3' end) |
|---|---|---|
| Surrogate target 5 | SEQ ID NO: 13 | CATCAGGAGCAGTTACGAAG AATAATGATGT<u>GAGGAGCGA TGACGGAATA</u> |
| Surrogate target 6 | SEQ ID NO: 14 | CATCAGGAGCAGTTACGAAG AATAATGATGAATAATGATG <u>TGAGGAGCGATGACGGAATA</u> |
| Assistant primer 2 | SEQ ID NO: 19 | TGTGGGTTTGCCCT TCAGATGG |

TABLE 11

Sequence of detection probe

| Name | SEQ ID NO | Nucleotide sequence (N terminus --> C terminus) |
|---|---|---|
| Probe 3 | SEQ ID NO: 22 | [Dabcyl]-[K]-[Dabcyl]-CACCGCTGG-[O linker]-[K]-[ROX] |

Surrogate target 5 was prepared as a single-stranded oligonucleotide having a length of 50 nucleotides. In the nucleotide sequence of surrogate target 5, the underlined nucleotide sequence is complementary to the target nucleotide sequence of the human HRAS gene, and the italicized nucleotide sequence is the same as the nucleotide sequence of amplification primer 1.

Surrogate target 6 was prepared as a single-stranded oligonucleotide having a length of 60 nucleotides. In the nucleotide sequence of surrogate target 6, the underlined nucleotide sequence is complementary to the target nucleotide sequence of the human HRAS gene, and the italicized nucleotide sequence is same as the nucleotide sequence of amplification primer 1.

Probe 3 was prepared as a 9-nucleoide PNA, and two quenchers [Dabcyl] linked to each other by [K (lysine)] were attached at the N-terminus of the PNA, and the reporter [ROX] was attached at the C-terminus of the PNA. The PNA and the [ROX] were linked to each other by [O linker] and [K (lysine)]. In addition, at the portions indicated by [ˆ] in the nucleotide sequence of probe 3, a positively charged functional group (glutamate) was connected to the PNA backbone, thereby introducing the charge into the PNA backbone that was not originally charged. When probe 3 hybridizes with the fusion amplicon having a complementary nucleotide sequence, the quencher and the reporter are separated by the longest distance, and at this time, the signal (fluorescence) value from the reporter reaches maximum, and thus the fusion amplicon can be detected by measuring the signal.

The nucleotide sequence of probe 3 is characterized in that it is not complementary to any of target-specific primer 3, amplification primer 1, surrogate target 5, surrogate target 6 and assistant primer 2, but is complementary to a target nucleic acid amplicon strand caused by assistant primer 2 and an amplicon strand caused by amplification primer 1 in the fusion amplicon comprising a portion of the nucleotide sequence of surrogate target 5 or surrogate target 6. However, since the amount of assistant primer 2 added is very small and target-specific primer 3, which is paired with the assistant primer, is added in a relatively large amount, a detectable signal cannot be emitted merely by hybridization of probe 3 with the target nucleic acid amplicon strand caused by assistant primer 2. On the other hand, amplification primer 1 that amplifies the fusion amplicon is added in a very large amount, and target-specific primer 3, which is paired, is added in a relatively small amount, and hence when probe 3 hybridizes with the amplicon strand caused by amplification primer 1 in the fusion amplicon, a signal can be effectively emitted, whereby only the fusion amplicon can be selectively detected.

5.2 Production and Identification of Fusion Amplicon

In order to form the intended fusion amplicon under a condition in which about 25 ng of extracted human genomic DNA is present, a polymerase chain reaction composition comprising 1.5 pmole of target-specific primer 3, 30 pmole of amplification primer 1, 0.5 pmole of assistant primer 2, 50 fmole of surrogate target 5 or surrogate target 6, and 4 pmole of probe 3 was prepared. The polymerase chain reaction composition contained a DNA polymerase, which is commonly used in polymerase chain reactions, as well as components such as buffer, deoxynucleotide-5-triphosphate (dNTP), potassium chloride (KCl), magnesium chloride ($MgCl_2$) and a detergent.

Temperature control for the polymerase chain reaction was performed by a general thermal cycler, and the polymerase chain reaction was performed under the following conditions: initial denaturation [at 95° C. for 5 min], and then 15 cycles, each consisting of denaturation [at 95° C. for 20 sec]–annealing [at 64° C. for 20 sec]–extension [at 72° C. for 20 sec], which is a first cycling step, followed by 35 cycles, each consisting of denaturation [at 95° C. for 20 sec]–annealing [at 60° C. for 20 sec]–extension [at 72° C. for 20 sec], which is a second cycling step.

After the polymerase chain reaction, in order to obtain a melting curve of the reaction product, the reaction product was subjected to denaturation [at 95° C. for 5 min]–annealing [at 25° C. for 5 min]–melting [25→75° C. with 0.5° C. interval], and the fluorescence value of the ROX channel, measured in the melting step, was analyzed to obtain the melting peak results.

In addition, for comparison with the performance of the target nucleic acid amplification method of the present invention for detection of the region corresponding to codons 12 and 13 of exon 2 of the HRAS gene, detection of the same region using a conventional polymerase chain reaction as a control was also performed, and a composition for the control polymerase chain reaction was prepared by excluding surrogate target 5, surrogate target 6 and amplification primer 1 from the polymerase chain reaction composition and increasing the added amount of control primers, comprising assistant primer 2, to 30 pmole. The nucleotide sequences of the control primers used are shown in Table 12 below.

TABLE 12

Sequences of control primers

| Name | SEQ ID NO | Nucleotide sequence (N terminus --> Cterminus) |
|---|---|---|
| Control primer 1 (same as assistant primer 2) | SEQ ID NO: 19 | TGTGGGTTTGCCCTTCAGATGG |

TABLE 12 -continued

Sequences of control primers

| Name | SEQ ID NO | Nucleotide sequence (N terminus --> Cterminus) |
|---|---|---|
| Control primer 2 | SEQ ID NO: 23 | TGAGGAGCGATGACGGAATA |
| Control prime 3 | SEQ ID NO: 24 | CCTGTAGGAGGACCCCGG |

Temperature control for the control polymerase chain reaction was performed using a general thermal cycler, and the polymerase chain reaction was performed under the following conditions: initial denaturation [at 95° C. for 5 min], and then 15 cycles, each consisting of denaturation [at 95° C. for 20 sec]–annealing [at 64° C. for 20 sec]-extension [at 72° C. for 20 sec], which is a first cycling step, followed by 35 cycles, each consisting of denaturation [at 95° C. for 20 sec]–annealing [at 60° C. for 20 sec]–extension [at 72° C. for 20 sec], which is a second cycling step.

After the polymerase chain reaction, in order to obtain a melting curve of the reaction product, the reaction product was subjected to denaturation [at 95° C. for 5 min]-annealing [at 25° C. for 5 min]–melting [25→75° C. with 0.5° C. interval], and the fluorescence value of the ROX channel, measured in the melting step, was analyzed to obtain the melting peak results.

In addition, in order to examine whether detection of codons 12 and 13 of exon 2 of HRAS by the target nucleic acid amplification method of the present invention and the control polymerase chain reaction could be false-positive, a test was performed under a condition in which about 25 ng of extracted human genomic DNA was present and under a condition in which no target nucleic acid was added (no template control (NTC)).

As a result, it was confirmed that, when the target nucleic acid amplification method of the present invention was used, under the condition in which the human genomic DNA was added, amplification and detection of the region of codons 12 and 13 of exon 2 of HRAS, which has a high G/C content, was normally achieved, and under the condition in which the target nucleic acid was not added, a melting peak on the melting curve was not formed, suggesting that there were no false-positives.

At this time, it was confirmed that the G/C content of the target nucleic acid region in the fusion amplicon was as high as 63.1%, but the G/C contents of the fusion amplicons obtained using any nucleotide sequences of surrogate target 5 and surrogate target 6 were lowered to 55.8% and 52.4%, respectively. On the other hand, when the conventional polymerase chain reaction as the control was used, it was attempted to detect the target nucleic acid by producing three types of amplicons showing G/C contents of 63.1%, 68.4% and 69.8%, respectively, but a lot of false positives appeared, making it difficult to trust the detection results (when detecting the target nucleic acid through amplicon 1 and amplicon 2). In addition, in this case, the melting temperature shown by the melting peak was outside the normal range (when detecting the target nucleic acid through amplicon 2), or the melting peak was abnormally formed (when detecting the target nucleic acid through amplicon 3), and consequently, it was difficult to amplify and detect the target nucleic acid (FIG. 13A-FIG. 13F).

Example 6. Adjustment of Sensitivity of Human Epidermal Growth Factor Receptor Gene Detection 6.1 Preparation of Primers, Surrogate Target, and Probe In order to arbitrarily adjust the sensitivity of detection while minimizing effects on amplification efficiency when detecting the above-described human EGFR gene by the target nucleic acid amplification method of the present invention, target-specific primer 4, surrogate target 7 and assistant primer 1, which are capable of hybridizing specifically with the EGFR gene, were designed and prepared, and amplification primer 3 capable of hybridizing specifically with surrogate target 7, and probe 2 capable of hybridizing specifically with a produced fusion amplicon comprising a portion of surrogate target 7 were also designed and prepared (the primers and the surrogate target were manufactured by Integrated DNA Technologies, Inc., USA, and the probe was manufactured by PANAGENE Inc., South Korea). The nucleotide sequences of each primer, the surrogate target and the probe are shown in Tables 13 and 14 below.

TABLE 13

Sequences of primers and surrogate

| Name | SEQ ID NO | Nucleotide sequence (5' end --> 3' end) |
| --- | --- | --- |
| Target-specific primer 4 | SEQ ID NO: 4 | GCCGCCTGCTGGGCATC |
| Amplification primer 3 | SEQ ID NO: 8 | GCTGTTGCTTCCGCTATTC |
| Surrogate target 7 | SEQ ID NO: 15 | TTTTTT*CAGCTCATGCCCTT CGGCTAGGAATAGCGGAAGC AACAGC*AAAAAA |
| Assistant primer 1 | SEQ ID NO: 18 | GCTATCCCAGGAGCGC AGACC |

TABLE 14

Sequence of detection probe

| Name | SEQ ID NO | Nucleotide sequence (N terminus --> C terminus) |
| --- | --- | --- |
| Probe 2 | SEQ ID NO: 21 | [Dabcyl]-CTCATCATGCAG-[K]-[FAM] |

Surrogate target 7 was prepared as a single-stranded oligonucleotide having a length of 52 nucleotides, and an oligonucleotide consisting of six thymine (T) bases and an oligonucleotide of six adenine (A) bases were present at the 5' end and 3' end of surrogate target 7, respectively, in order to prevent the surrogate target from functioning directly as a primer. In the nucleotide sequence of surrogate target 7, the underlined nucleotide sequence is complementary to the target nucleotide sequence of the human EGFR gene, and the italicized nucleotide sequence is complementary to the nucleotide sequence of amplification primer 3.

6.2 Production and Amplification Confirmation of Fusion Amplicon with Adjustment of Amount of Surrogate Target Added In order to adjust the target nucleic acid detection sensitivity represented by a Ct value while forming the intended fusion amplicon under about 1,000,000 copies of the target nucleic acid were present, different amounts (0.01 to 10 fmole) of surrogate target 7 were added to a polymerization chain reaction composition comprising 1.5 pmole of target-specific primer 4, 30 pmole of amplification primer 3, 0.5 pmole of assistant primer 1, and 4 pmole of probe 2. That is, surrogate target 7 which has been originally added in an amount of 10 fmole was diluted 1-fold, 0.1-fold, 0.01-fold and 0.001-fold so as to be added in amounts of 10 fmole, 1 fmole, 0.1 fmole, and 0.01 fmole, respectively. The polymerase chain reaction composition contained a DNA polymerase, which is commonly used in polymerase chain reaction, as well as components such as buffer, deoxynucleotide-5-triphosphate (dNTP), potassium chloride (KCl), magnesium chloride ($MgCl_2$) and a detergent.

Temperature control for the polymerase chain reaction was performed by a general thermal cycler, and the polymerase chain reaction was performed under the following conditions: initial denaturation [at 95° C. for 15 min], and then 15 cycles, each consisting of denaturation [at 95° C. for 10 sec]–annealing [at 64° C. for 20 sec]–extension [at 72° C. for 20 sec], which is a first cycling step, followed by 35 cycles, each consisting of denaturation [at 95° C. for 10 sec]–annealing [at 58° C. for 20 sec]–extension [at 72° C. for 20 sec], which is a second cycling step. For each cycle in the second cycling step, an amplification curve was obtained by measuring the fluorescence value of the FAM channel.

In addition, for comparison with the performance of the target nucleic acid amplification method of the present invention for adjustment of the detection sensitivity of the EGFR gene, detection and sensitivity adjustment of the same region using a conventional polymerase chain reaction as a control was also performed, and compositions for the control polymerase chain reaction were prepared by excluding surrogate target 7 and amplification primer 3 from the polymerase chain reaction composition, diluting 1.5 pmole of the target-specific primer and 30 pmole of the assistant primer 1-fold, 0.5-fold, 0.25-fold, 0.1-fold and 0.01-fold, and then adding the dilutions.

Temperature control for the control polymerase chain reaction was performed using a general thermal cycler, and the control polymerase chain reaction was performed under the following conditions: initial denaturation [at 95° C. for 15 min], and then 50 cycles, each consisting of denaturation [at 95° C. for 10 sec]–annealing [at 58° C. for 20 sec]–extension [at 72° C. for 20 sec]. For each cycle, an amplification curve was obtained by measuring the fluorescence value of the FAM channel.

As a result, it was observed that, when the target nucleic acid amplification method of the present invention was used, as the amount of surrogate target 7 added decreased, the rise of the amplification curve was constantly delayed, and thus the sensitivity was adjusted by a gradual increase in the Ct value.

In addition, in this case, it was confirmed that even though the rise of the amplification curve was delayed, the slope of the amplification curve was maintained almost constant, and thus the effect on amplification efficiency was minimized. On the other hand, in the control conventional method in which the amounts of target-specific primer and assistant primer added were adjusted, it was observed that the phenomenon in which the rise of the amplification curve was delayed similarly appeared, but the slope of the amplification curve was significantly lowered as the rise of the amplification curve was delayed. Thereby, it was confirmed that, in the conventional method, adjustment of the sensitivity had a great effect on amplification efficiency, and when the amounts of primers added were significantly decreased, no target nucleic acid amplification could occur (FIG. 14A and FIG. 14B).

Example 7. Multiplex Amplification and Detection of Human Epidermal Growth Factor Receptor Gene and HRAS Gene

7.1 Preparation of Primers, Surrogate Targets, and Probe

In order to effectively amplify and detect the above-described human EGFR gene and HRAS gene at the same time, target-specific primer 2, surrogate target 2, surrogate target 3 and assistant primer 1, which are capable of hybridizing specifically with the region around codon 790 of exon 20 of the EGFR gene, were designed, and amplification primer 1, which is capable of hybridizing with surrogate target 2 and has the same sequence as a portion of the nucleotide sequence of surrogate target 3, was designed and prepared (Integrated DNA Technologies, Inc., USA). In addition, probe 2 was designed and prepared so that it could detect a fusion amplicon produced and amplified by the designed primers and surrogate targets (PANAGENE Inc., South Korea). Furthermore, target-specific primer 5, surrogate target 8, surrogate target 9 and assistant primer 2, which are capable of hybridizing specifically with the region corresponding to codons 12 and 13 of exon 2 of the HRAS gene, were designed, and amplification primer 1, which is capable of hybridizing with surrogate target 8 and has the same sequence as a portion of the nucleotide sequence of surrogate target 9, was designed and prepared (Integrated DNA Technologies, Inc., USA). In addition, probe 3 was designed and prepared so that it could detect a fusion amplicon produced and amplified by the designed primers and surrogate targets (PANAGENE Inc., South Korea). The nucleotide sequences of each primer, each surrogate target and each probe are shown in Tables 15 and 16 below.

TABLE 15

Sequences of primers and surrogate targets

| Name | SEQ ID NO | Nucleotide sequence (5' end --> 3' end) |
|---|---|---|
| Target-specific primer 2 | SEQ ID NO: 2 | ACCTCCACCGTGCAGCTCA |
| Target-specific primer 5 | SEQ ID NO: 5 | GGTCAGCGCACTCTTGCC |
| Amplification primer 1 | SEQ ID NO: 6 | CATCAGGAGCAGTTACGAAG |
| Surrogate target 2 | SEQ ID NO: 10 | CTGGACTATGTCCGGGAACA CAGGCTTCGTAACTGCTCCT GATGAAAAAA |
| Surrogate target 3 | SEQ ID NO: 11 | CATCAGGAGCAGTTACGAAG CCTGTGTTCCCGGACATAGT CCAG |
| Surrogate target 8 | SEQ ID NO: 16 | ATATTCCGTCATCGCTCCTC GGCTTCGTAACTGCTCCTGA TGAAAAAA |
| Surrogate target 9 | SEQ ID NO: 17 | CATCAGGAGCAGTTACGAAG CCGAGGAGCGATGACGGAATAT |
| Assistant primer 1 | SEQ ID NO: 18 | GCTATCCCAGGAGCGCAGACC |

TABLE 15-continued

Sequences of primers and surrogate targets

| Name | SEQ ID NO | Nucleotide sequence (5' end --> 3' end) |
|---|---|---|
| Assistant primer 2 | SEQ ID NO: 19 | TGTGGGTTTGCCCTTCAGATGG |

TABLE 16

Sequences of detection probes

| Name | SEQ ID NO | Nucleotide sequence (N terminus --> C terminus) |
|---|---|---|
| Probe 2 | SEQ ID NO: 21 | [Dabcyl]-CTCATCATGCAG-[K]-[FAM] |
| Probe 3 | SEQ ID NO: 22 | [Dabcyl]-[K]-[Dabcyl]-CACCGCTGG-[O linker]-[K]-[ROX] |

Surrogate target 8 was prepared as a single-stranded oligonucleotide having a length of 48 nucleotides, and an oligonucleotide consisting of six adenine (A) bases was present at the 3' end of surrogate target 8 in order to prevent the surrogate target from functioning directly as a primer. In the nucleotide sequence of surrogate target 8, the underlined nucleotide sequence is complementary to the target nucleotide sequence of the human HRAS gene, and the italicized nucleotide sequence is complementary to the nucleotide sequence of amplification primer 1.

Surrogate target 9 was prepared as a single-stranded oligonucleotide having a length of 42 nucleotides. In the nucleotide sequence of surrogate target 9, the underlined nucleotide sequence is complementary to the target nucleotide sequence of the human HRAS gene, and the italicized nucleotide sequence is identical to the nucleotide sequence of amplification primer 1.

7.2 Multiplex Detection by Production of Fusion Amplicon

In order to simultaneously detect a human EGFR gene target and a human HRAS gene target by formation of the intended fusion amplicon under a condition in which about 1,000,000 copies of the human EGFR gene target were mixed with 10, 100, 1,000, 10,000 or 100,000 copies of the human HRAS gene target or under a condition in which about 1,000,000 copies of the human HRAS gene target were mixed with 10, 100, 1,000, 10,000 or 100,000 copies of the human EGFR gene target, a polymerase chain reaction composition was prepared comprising 1.5 pmole of target-specific primer 2, 1.5 pmole of target-specific primer 5, 30 pmole of amplification primer 1, 0.5 pmole of assistant primer 1, 0.5 pmole of assistant primer 2, 10 fmole of surrogate target 2, 10 fmole of surrogate target 3, 10 fmole of surrogate target 8, 10 fmole of surrogate target 9, 4 pmole of probe 2, and 4 pmole of probe 3. The polymerase chain reaction composition contained a DNA polymerase, which is commonly used in polymerase chain reaction, as well as components such as buffer, deoxynucleotide-5-triphosphate (dNTP), potassium chloride (KCl), magnesium chloride (MgCl$_2$) and a detergent.

Temperature control for the polymerase chain reaction was performed using a general thermal cycler, and the polymerase chain reaction was performed under the following conditions: initial denaturation [at 95° C. for 15 min], and then 15 cycles, each consisting of denaturation [at 95° C. for 10 sec]–annealing [at 64° C. for 30 sec]–extension [at 72° C. for 20 sec], which is a first cycling step, followed by 35 cycles, each consisting of denaturation [at 95° C. for 10 sec]–annealing [at 60° C. for 20 sec]–extension [at 72° C. for 20 sec], which is a second cycling step.

After the polymerase chain reaction, in order to obtain a melting curve of the reaction product, the reaction product was subjected to denaturation [at 95° C. for 5 min]–annealing [at 35° C. for 5 min]–melting [35→75° C. with 0.5° C. interval], and the fluorescence values of the FAM channel and the ROX channel, measured in the melting step, were analyzed to obtain the melting peak results.

As a result, it was observed that, when the target nucleic acid amplification method of the present invention was used, the two targets were completely detected simultaneously even under the condition in which the plurality of target nucleic acids were mixed unevenly, that is, under the condition in which the amount of the HRAS gene target was very smaller than the amount of the EGFR gene target (that is, $1/10$, $1/100$, $1/1,000$ or $1/10,000$) or under the condition in which the amount of the EGFR gene target is much smaller than the amount of the HRAS gene target (that is, $1/10$, $1/100$, $1/1,000$ or $1/10,000$). On the other hand, in the conventional method as the control, it was observed that detection of the gene target added in a relatively large amount was easy, but simultaneous detection of a relatively small amount of the gene target mixed with the gene target added in a relatively large amount was unstable (FIG. 15A-FIG. 15L).

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

INDUSTRIAL APPLICABILITY

According to the target nucleic acid amplification method of the present invention, a portion of the nucleotide sequence of the polymerase chain reaction (PCR) product may be arbitrarily adjusted, and consequently, dependence on the nucleotide sequence of the target nucleic acid may be minimized. Thus, even if amplification of the region of interest of the target nucleic acid is difficult due to the excessively high G/C content of the region, amplification thereof can be effectively performed. In addition, since an arbitrary nucleotide sequence may be inserted between the target nucleic acid-complementary nucleotide sequence portion and the amplification primer-complementary nucleotide sequence of the surrogate target, a universal probe that hybridizes with this arbitrary nucleotide sequence may be prepared. Thus, even though the nucleotide sequence of the target nucleic acid is changed, the universal probe can advantageously be used continuously, and thus is useful for molecular diagnosis, prenatal diagnosis, early diagnosis, cancer diagnosis, genetic related diagnosis, genetic trait diagnosis, diagnosis of infectious bacteria, identification of drug-resistant bacteria, forensic medicine, species identification of organisms, and the like.

In addition, according to the target nucleic acid amplification method of the present invention, the sensitivity of target nucleic acid amplification can be easily adjusted by controlling the amount of surrogate target added, and at the same time, the effect of this adjustment on the efficiency of amplification can be minimized, and thus an optimization process during the development of diagnostic products can be performed more efficiently.

The invention claimed is:

1. A method for amplifying a target nucleic acid, the method comprising steps of:
   (a) isolating a nucleic acid from a sample;
   (b) performing a polymerase chain reaction (PCR) by adding
      i) at least one target-specific primer capable of hybridizing with the target nucleic acid,
      ii) at least one surrogate target comprising a sequence that binds to a target nucleic acid region to which the target-specific primer does not bind, and an arbitrary sequence that does not bind to the target nucleic acid, and
      iii) at least one amplification primer capable of amplifying the surrogate target; and
   (c) determining the presence or absence of a fusion amplicon.

2. The method of claim 1, wherein the target nucleic acid region to which the target-specific primer does not bind is present downstream of the target-specific primer, and the downstream of the target-specific primer is a direction in which the target-specific primer is extended by PCR after binding to the target nucleic acid.

3. The method of claim 1, wherein the surrogate target further comprises, at the 3' end thereof, a functional group or an oligonucleotide sequence for inhibiting nucleic acid polymerization.

4. The method of claim 3, wherein the functional group or the oligonucleotide sequence for inhibiting nucleic acid polymerization is one or more selected from the group consisting of an amine group, a phosphate group, an alkyl group, alkane-diol, phosphorothioate, biotin, a non-nucleotide linker, a C3-18 spacer, a dideoxynucleotide triphosphate (ddNTP), an inverted deoxynucleotide triphosphate (inverted dNTP), and an inverted dideoxynucleotide triphosphate (inverted ddNTP).

5. The method of claim 1, wherein each of the target-specific primer, the surrogate target and the amplification primer is composed of any one or a mixture of two or more of an oligonucleotide, LNA (locked nucleic acid), and PNA (peptide nucleic acid).

6. The method of claim 5, wherein the surrogate target is an oligonucleotide prepared to have a length of 10 to 500 nucleotides.

7. The method of claim 6, wherein the surrogate target is a single-stranded oligonucleotide prepared to have a length of 20 to 150 nucleotides.

8. The method of claim 6, wherein the surrogate target further comprises a spacer which is a single-stranded oligonucleotide prepared to have a length of 1 to 100 nucleotides.

9. The method of claim 8, wherein the spacer has a GC content of 30% or less.

10. The method of claim 6, wherein the surrogate target further comprises a spacer which is a single-stranded oligonucleotide prepared to have a length of 2 to 20 nucleotides.

11. The method of claim 1, wherein the surrogate target hybridizes with a strand which is the same as or opposite to the target nucleic acid strand with which the target-specific primer hybridizes.

12. The method of claim 1, wherein the amplification primer is the same as the arbitrary sequence of the surrogate target or is complementary to the arbitrary sequence of the surrogate target.

13. The method of claim 1, wherein the fusion amplicon has a length of 50 bp to 1 kbp and a GC content of 35 to 65%.

14. The method of claim 1, wherein the step (c) of determining the presence or absence of the fusion amplicon is performed using a nucleic acid-binding dye or a probe capable of binding to the fusion amplicon.

15. The method of claim 14, wherein the nucleic acid-binding dye is selected from the group consisting of ethidium bromide, BEBO, and BEXTO.

16. The method of claim 14, wherein the probe capable of binding to the fusion amplicon is selected from the group consisting of an oligonucleotide, LNA, PNA, and mixtures thereof.

17. The method of claim 16, wherein the probe capable of binding to the fusion amplicon binds to the arbitrary sequence of the surrogate target.

18. The method of claim 16, wherein a reporter and a quencher are linked to both ends of the probe capable of binding to the fusion amplicon.

19. The method of claim 18, wherein the reporter is one or more fluorescent substances selected from the group consisting of fluorescein, fluorescein chlorotriazinyl, tetramethylrhodamine, FITC, TRITC, and thiadicarbocyanine dyes.

20. The method of claim 18, wherein the quencher is Dabcyl.

21. The method of claim 1, wherein the target nucleic acid is double-stranded, and wherein step (b) further comprises adding an assistant primer that hybridizes with the opposite strand of the target nucleic acid, with which the target-specific primer hybridizes.

* * * * *